US009296797B2

(12) United States Patent
Ulijasz et al.

(10) Patent No.: US 9,296,797 B2
(45) Date of Patent: Mar. 29, 2016

(54) PHYTOCHROME-BASED FLUOROPHORES

(75) Inventors: Andrew T. Ulijasz, Madison, WI (US);
Junrui Zhang, Madison, WI (US);
Katrina T. Forest, Madison, WI (US);
David Anstrom, Middleton, WI (US);
Jeremiah R. Wagner, Madison, WI
(US); Richard D. Vierstra, Madison, WI
(US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 481 days.

(21) Appl. No.: 12/167,222

(22) Filed: Jul. 2, 2008

(65) Prior Publication Data
US 2009/0061444 A1    Mar. 5, 2009

Related U.S. Application Data

(60) Provisional application No. 60/958,261, filed on Jul. 3, 2007.

(51) Int. Cl.
| C07H 21/04 | (2006.01) |
| C12N 15/11 | (2006.01) |
| C12N 1/19 | (2006.01) |
| C07K 14/00 | (2006.01) |
| C07K 14/415 | (2006.01) |
| C07K 14/195 | (2006.01) |
| G01N 33/533 | (2006.01) |
| G01N 33/58 | (2006.01) |
| C12N 5/04 | (2006.01) |
| C12Q 1/68 | (2006.01) |

(52) U.S. Cl.
CPC ............. *C07K 14/415* (2013.01); *C07K 14/195* (2013.01); *G01N 33/533* (2013.01); *G01N 33/582* (2013.01); *C12Q 1/6897* (2013.01)

(58) Field of Classification Search
USPC ....................... 435/6.17, 69.7, 366, 325, 419; 536/23.7; 530/350
See application file for complete search history.

(56) References Cited

U.S. PATENT DOCUMENTS

| 5,491,084 A | 2/1996 | Chalfie et al. | |
| 6,046,014 A | 4/2000 | Lagarias et al. | |
| 2003/0134787 A1* | 7/2003 | Rothman et al. | 514/12 |
| 2010/0303729 A1 | 12/2010 | Ulijasz et al. | |
| 2015/0056646 A1 | 2/2015 | Ulijasz et al. | |

FOREIGN PATENT DOCUMENTS

WO    2010/138727    12/2010

OTHER PUBLICATIONS

Wellems et al. (Homologous genes encode two distinct histidine-rich proteins in a cloned isolate of Plasmodium falciparum, 1986, PNAS, vol. 83, pp. 6065-6069).*
Davis et al. (Bacteriophytochromes: phytochrome-like photoreceptors from nonphotosynthetic eubacteria, 1999, Science, vol. 286, pp. 2517-2520).*
Wurm (Production of recombinant protein therapeutics in cultivated mammalian cells, Nature Biotechnology, 2004, vol. 22, pp. 1393-1398).*
von Stetten et al. (Highly conserved residues D197 and H250 in Agp1 phytochrome control the proton affinity of the chromophore and Pfr formation, 2007, J. Biol. Chem., vol. 282, pp. 2116-2123, published online Nov. 22, 2006).*
Allewalt et al., "Effect of Temperature and Light on Growth of and Photosynthesis by *Synechococcus* Isolates Typical of Those Predominating in the Octopus Spring Microbial Mat Community of Yellowstone National Park," *Appl. Environ. Microbiol.*, 72(1):544-550 (2006).
Altschul et al., "Gapped BLAST and PSI-BLAST: A New Generation of Protein Database Search Programs," *Nucl. Acids Res.*, 25(17):3389-3402 (1997).
Ausubel et al., "Current Protocols in Molecular Biology," *John Wiley & Sons, Inc.*, vols. 1-5, Table of Contents, 14 pages.
Becke, "Density-Functional Thermochemistry. III. The Role of Exact Exchange," *J. Chem. Phys.*, 98(7):5648-5652 (1993).
Bhaya et al., "Population Level Functional Diversity in a Microbial Community Revealed by Comparative Genomic and Metagenomic Analyses," *ISME J.*, 1:703-713 (2007).
Bhoo et al., "Phytochrome Photochromism Probed by Site-Directed Mutations and Chromophore Esterification," *J. Amer. Chem. Soc.*, 119:11717-11718 (1997).
Bhoo et al., "Bacteriophytochromes are Photochromic Histidine Kinases Using a Biliverdin Chromophore," *Nature*, 414:776-779 (2001).
Borucki et al., "Light-Induced Proton Release of Phytochrome is Coupled to the Transient Deprotonation of the Tetrapyrrole Chromophore," *J. Biol. Chem.*, 280(40):34358-34364 (2005).
Collins et al., "A Preliminary Solubility Screen Used to Improve Crystallization Trials: Crystallization and Preliminary X-ray Structure Determination of *Aeropyrum Pernix* Flap Endonuclease-1," *Acta. Crystallogr. D. Biol. Crystallogr.* 60:1674-1678 (2004).
Delaglio et al., "NMRPipe: A Multidimensional Spectral Processing System Based on UNIX Pipes," *J. Biomol. NMR*, 6:277-293 (1995).
Esteban et al., "Light-Induced Conformational Changes of Cyanobacterial Phytochrome Cph1 Probed by limited Proteolysis and Autophosphorylation," *Biochemistry* 44:450-461 (2005).
Fischer and Lagarias, "Harnessing Phytochrome's Glowing Potential," *Proc. Natl. Acad. Sci. USA*, 101(50):17334-17339 (2004).
Fischer et al., "Multiple Roles of a Conserved GAF Domain Tyrosine Residue in Cyanobacterial and Plant Phytochromes," *Biochemistry*, 44:15203-15215 (2005).
Gambetta and Lagarias, "Genetic Engineering of Phytochrome Biosynthesis in Bacteria," *Proc. Natl. Acad. Sci. USA*, 98(19):10566-10571 (2001).

(Continued)

*Primary Examiner* — Sharmila G. Landau
*Assistant Examiner* — Shannon Janssen
(74) *Attorney, Agent, or Firm* — Michael Best & Friedrich LLP

(57) ABSTRACT

Genetically-engineered fluorophore molecules with increased fluorescence are provided. These fluorophores are derived from the domains of phytochromes, and in particular bacterial phytochromes. Methods for generating these fluorophores and various applications of these fluorophores are also provided.

17 Claims, 27 Drawing Sheets

(56) References Cited

OTHER PUBLICATIONS

Hahn et al., "Probing Protein-Chromophore Interactions in Cph1 Phytochrome by Mutagenesis," *FEBS J.*, 273:1415-1429 (2006).

Karlin and Altschul, "Methods for Assessing the Statistical Significance of Molecular Sequence Features by Using General Scoring Schemes," *Proc. Natl. Acad. Sci. USA*, 87:2264-2268 (1990).

Karniol et al., "Phylogenetic Analysis of the Phytochrome Superfamily Reveals Distinct Microbial Subfamilies of Photoreceptors," *Biochem. J.*, 392:103-116 (2005).

Karniol and Vierstra, "The Pair of Bacteriophytochromes from *Agrobacterium tumefaciens* are Histidine Kinases with Opposing Photobiological Properties," *Proc. Natl. Acad. Sci. USA*, 100(5):2807-2812 (2003).

Karniol and Vierstra, "Structure, Function, and Evolution of Microbial Phytochromes," *Photomorphogenesis in Plants and Bacteria*, 3$^{rd}$ ed., 65-98 (2006).

Keppler et al., "Labeling of Fusion Proteins with Synthetic Fluorophores in Live Cells," *Proc. Natl. Acad. Sci. USA*, 101(27):9955-9959 (2004).

Kneip et al., "Protonation State and Structural Changes of the Tetrapyrrole Chromophore During the $P_r \to P_{fr}$ Phototransformation of Phytochrome: A Resonance Raman Spectroscopic Study," *Biochemistry*, 38:15185-15192 (1999).

Kriegler, "Gene Transfer and Expression: A Laboratory Manual," M. Stockton Press, (1990), 6 pages, TOC.

Magdo et al., "Calculation of Vibrational Spectra of Linear Tetrapyrroles. I. Global Sets of Scaling Factors for Force Fields Derived by ab Initio and Density Functional Theory Methods," *J. Phys. Chem. A*, 103:289-303 (1999).

Malhotra et al., "Identification of Chromophore Binding Domains of Yeast DNA Photolyase," *J. Biol. Chem.*, 267(5):2909-2914 (1992).

Meier, "Vibrational Spectroscopy: A 'Vanishing' Discipline?," *Chem Soc. Rev.*, 34:734-752 (2005).

Miller et al., "Single-Molecule Dynamics of Phytochrome-Bound Fluorophores Probed by Fluorescence Correlation Spectroscopy," *Proc. Natl. Acad. Sci. USA*, 103(30):11136-11141 (2006).

Mroginski et al., "Calculation of the Vibrational Spectra of Linear Tetrapyrroles. 2. Resonance Raman Spectra of Hexamethylpyrromethene Monomers," *J. Phys. Chem. B*, 104:10885-10899 (2000).

Mroginski et al., "Determination of the Chromophore Structures in the Photoinduced Reaction Cycle of Phytochrome," *J. Am. Chem. Soc.*, 126:16734-16735 (2004).

Mroginski et al., "The Chromophore Structural Changes during the Photocycle of Phytochrome: A Combined Resonance Raman and Quantum Chemical Approach," *Acc. Chem. Res.*, 40(4):258-266 (2007).

Murphy and Lagarias, "The Phytofluors: A New Class of Fluorescent Protein Probes," *Current Biology*, 7:870-876 (1997).

Oka et al., "Functional Analysis of a 450-Amino Acid N-Terminal Fragment of Phytochrome B in Arabidopsis," *Plant Cell*, 16:2104-2116 (2004).

Park et al., "A Second Photochromic Bacteriophytochrome from *Synechocystis* sp. PCC 6803: Spectral Analysis and Down-Regulation by Light," *Biochemistry*, 39:10840-10847 (2000).

Pearson and Lipman, "Improved Tools for Biological Sequence comparison," *Proc. Natl. Acad. Sci. USA*, 85:2444-2448 (1988).

Quail, "An Emerging Molecular Map of the Phytochromes," *Plant Cell Environ.*, 20:657-665 (1997).

Remberg et al., "Raman Spectroscopic and Light-Induced Kinetic Characterization of a Recombinant Phytochrome of the Cyanobacterium *Synechocystis*," *Biochemistry*, 36:13389-13395 (1997).

Remberg et al., "Differential Effects of Mutations in the Chromophore Pocket of Recombinant Phytochrome on Chromoprotein Assembly and $P_r$-to-$P_{fr}$ Photoconversion," *Eur. J. Biochem.*, 266:201-208 (1999).

Rohmer et al., "$^{15}$N MAS NMR Studies of Cph1 Phytochrome: Chromophore Dynamics and Intramolecular Signal Transduction," *J. Phys. Chem. B.*, 110:20580-20585 (2006).

Sambrook et al., *Molecular Cloning, a Laboratory Manual*, 2$^{nd}$ ed., Cold Spring Harbor Laboratory Press (1989), Table of Contents, 30 pages.

Sawers et al., "Diversity of Phytochrome Chromophores," *Plant Physiology Online*, http://4eplantphys.net/article.php, pp. 1-5, 2006.

Scheer, "Model Compounds for the *Phytochrome Chromophore*," *Techniques in Photomorphogenesis*, pp. 227-256 (1984).

Shaner et al., "Improved Monomeric Red, Orange and Yellow Fluorescent Proteins Derived from *Discosoma* sp. Red Fluorescent Protein," *Nature Biotechnology*. 22(12):1567-1572 (2004).

Steunou et al., "In situ Analysis of Nitrogen Fixation and Metabolic Switching in Unicellular Thermophilic Cyanobacteria Inhabiting Hot Spring Microbial Mats," *Proc. Natl. Acad. Sci. USA*, 103(7):2398-2403 (2006).

Strauss et al., "Heteronuclear Solution—State NMR Studies of the Chromophore in Cyanobacterial Phytochrome Cph1," Biochemistry, 44:8244-8250 (2005).

Ulijasz et al., "A Vancomycin-Inducible LacZ Reporter System in *Bacillus subtilis*: Induction by Antibiotics that Inhibit Cell Wall Synthesis and by Lysozyme," *J. Bacteriol.*, 178(21):6305-6309 (1996).

Venters et al., "Uniform $^{13}$C Isotope Labeling of Proteins with Sodium Acetate for NMR Studies: Application to Human Carbonic Anhydrase II," *Biochemistry*, 30:4491-4494 (1991).

Vierstra and Karniol, "Phytochromes in Microorganisms," *Handbook of Photosensory Receptors*, pp. 171-196 (2005).

von Steffen et al., "Highly Conserved Residues Asp-197 and His-250 in Agp1 Phytochrome Control the Proton Affinity of the Chromophore and Pfr Formation," *J. Biol. Chem.*, 282(3):2116-2123 (2007).

Wagner et al., "A Light-Sensing Knot Revealed by the Structure of the Chromophore-Binding Domain of Phytochrome," *Nature*, 438:325-331 (2005).

Wagner et al., "High Resolution Structure of *Deinococcus* Bacteriophytochrome Yields New Insights into Phytochrome Architercture and Evolution," *J. Biol. Chem.*, 282(16):12298-12309 (2007).

Wagner et al., "Mutational Analysis of *Deinococcus radiodurans* Bacteriophytochrome Reveals Key Amino Acids Necessary for the Photochromicity and Proton Exchange Cycle of Phytochromes," *J. Biol. Chem.*, 283(18):12212-12226 (2008).

Wang et al., "Conditional Stability of the HemA Protein (Glutamyl-tRNA Reductase) Regulates Heme Biosynthesis in *Salmonella typhimurium*," *J. Bacteriol.*, 181(4):1211-1219 (1999).

Wang et al., "Evolution of New Nonantibody Proteins via Iterative Somatic Hypermutation," *Proc. Natl. Acad. Sci. USA*, 101(48):16745-16749 (2004).

Wu and Lagarias, "Defining the Bilin Lyase Domain: Lessons from the Extended Phytochrome Superfamily," *Biochemistry*, 39:13487-13495 (2000).

Shu et al., "Mammalian Expression of Infrared Fluorescent Proteins Engineered from a Bacterial Phytochrome," *Science*, 324:804-807 (2009).

Davis, S.J. et al., "Bacteriophytochromes: phytochrome-like photoreceptors from nonphotosynthetic eubacteria," Science (1999) 286(5449):2517-2520.

Ishizuka, T. et al., "Characterization of cyanobacteriochrome TePixJ from a thermophilic cyanobacterium thermosynechococcus elongatus strain BP-1," Plant Cell Physiol. (2006) 47(9):1251-1261.

Lin, J. et al., "Whole-genome shotgun optical mapping of deinococcus radiodurans," Science (1999) 285 (5433):1558-1562.

Ulijasz, A.T. et al., "Characterization of two thermostable cyanobacterial phytochromes reveals global movements in the chromophore-binding domain during photoconversion," J. Biol Chem. (2008) 283(30):21251-21266.

Ikeuchi, M. et al., "Cyanobacterioshromes: a new superfamily of tetrapyrrole-binding photoreceptors in cyanobacteria," Photochem. Photobiol. Sci. (2008) 7:1159-1167.

Nakamura, Y. et al., SwissProt Accession No. Q8DLC7, Oct. 31, 2006, retrieved from the internet Aug. 20, 2010, http://www.ncbi.nlm.nih.gov/protein/81743662, 1 page.

Ulijasz, A.T. et al., "The cyanochromes: blue-green photoreversible photoreceptors defined by a stable double cysteine linkage to a phycoviolobilin-type chromophore," J. Biol. Chem.

(56) References Cited

OTHER PUBLICATIONS (2009( 284:29757-29772, retrieved from the Internet: https://mywebspace.wisc.edu/gcornilescu/web/pixj_jbc.pdf, 32 pages.
International Search Report and Written Opinion for Application No. PCT/US2010/36421 dated Oct. 20, 2010 (9 pages).
GenBank Accession No. BAC08476, GI:22294647, tlr0924 [Thermosynechococcus elongatus BP-1], Dec. 2007, 2 pages.
Rockwell, N.C. et al., "A second conserved GAF domain cysteine is required for the blue/green photoreversibility of cyanobacteriochrome Tlr0924 from thermosynechococcus elongatus," Biochem. (2008) 47:7304-7316.
Schmitz, O. et al., "CikA, a bacteriophytochrome that resets the cyanobacterial circadian clock," Science (2000) 289:765-768.
Sharrock, R.A. et al., "Novel phytochrome sequences in arabidopsis thaliana: structure, evolution, and differential expression of a plant regulatory photoreceptor family," Genes & Dev. (1989) 3:1745-1757.
UnitProtKB Accession No. P74111; Apr. 2008, 2 pages.
UnitProtKB Accession No. P14712, May 2008, 4 pages.
United States Patent Office Action for U.S. Appl. No. 12/789,112 dated Jun. 2, 2011 (30 pages).
Wikipedia, "Conserved sequence" http://en.wikipedia.org/wiki/Conserved_sequence, downloaded Jan. 24, 2012 (3 pages).
United States Patent Office Action for U.S. Appl. No. 12/789,112 dated Nov. 1, 2011 (13 pages).
Rockwell et al., "Phytochome Structure and Signaling Mechanisms," 2006, Annu. Rev. Plant Biol. 57:837-858.
Yoshihara et al., "Cyanobacterial phytochrome-like PixJ1 holoprotein shows novel reversible photoconversion between blue- and green-absorbing forms," 2004, Plant Cell Physiol. 45:1729-1737.
Ishizuka et al., "Cyanobacteriochrome TePixJ of Thermosynechococcus elongatus harbors phycoviolobilin as a chromophore," 2007, Plant Cell Physiol. 48:1385-1390.
Thompson et al., "CLUSTAL W: improving the sensitivity of progressive multiple sequence alignment through sequence weighting, position-specific gap penalties and weight matrix choice," 1994, Nucleic Acids Res. 22:4673-4680.
Pollastri et al., "Improving the prediction of protein secondary structure in three and eight classes using recurrent neural networks and profiles," 2002, Proteins 47:228-235.
Rodriguez et al., "A copper cofactor for the ethylene receptor ETR1 from Arabidopsis," 1999, Science 283:996-998.
Bhaya et al., "Light regulation of type IV pilus-dependent motility by chemosensor-like elements in Synechocystis PCC6803," 2001, Proc. Natl. Acad. Sci. USA 98:7540-7545.
Terauchi et al., "RcaE is a complementary chromatic adaptation photoreceptor required for green and red light responsiveness," 2004, Mol. Microbiol., 567-77.
Yeh et al., "A Cyanobacterial Phytochrome Two-Component Light Sensory System," 1997, Science, vol. 277, No. 5331, pp. 1505-1508.
Thor et al., "Chromophore structure in the photocycle of the cyanobacterial phytochrome Cph1," 2006, Biophys. J. 91:1811-1822.
United States Patent Office Notice of Allowance for U.S. Appl. No. 12/789,112 dated Apr. 30, 2014 (13 pages).
Zheng et al., "An efficient one-step site-directed and site-saturation mutagenesis protocol," Nucleic Acids Res., 32:e115, 5 pages, 2004.
United States Patent Office Action for U.S. Appl. No. 14/464,751 dated Sep. 17, 2015 (32 pages).
Sang, H., Mechanisms of Development 121:1179-1186, 2004.
User Manual for pBAD/Myc-His A, B, and C, Dec. 2010.

* cited by examiner

PHYTOCHROME-BASED FLUOROPHORES

CROSS-REFERENCE TO RELATED APPLICATIONS

This invention claims priority to U.S. Provisional Patent Application Ser. No. 60/958,261, filed Jul. 3, 2007, which is herein incorporated by reference.

GOVERNMENT INTERESTS

This invention was made with United States government support awarded by the following agencies: DOE, grant No. DE-FG02-88ER13968; and NSF, grant No. 0519970. The United States government has certain rights in this invention.

FIELD OF THE INVENTION

This invention relates to new fluorescent molecules, and particularly to phytochrome-based fluorophores with increased fluorescence.

BACKGROUND

Phytochrome is a photoreceptor, a pigment that organisms use to detect light. The unique photochromic properties of the phytochrome (Phy) photoreceptors allow them to photoconvert between two meta-stable forms, a red light (R) absorbing Pr form, and a far-red light (Fr) absorbing Pfr form. Phytochromes (Phys) act as light-regulated switches in a number of photosensory processes in plants, bacteria, and fungi.

Biochemically, phytochrome is a protein with a bilin chromophore. Sequence alignments and 3-dimensional structural analysis of the chromophore binding domain (CBD) of the bacteriophytochrome (BphP) from the proteobacterium *Deinococcus radiodurans* (*D. radiodurans*) demonstrate that many residues close to the phytochrome's biliverdin IXα (BV) chromophore are conserved throughout the Phy superfamily. This conservation suggests that these residues have been retained through evolution because they play important roles in bilin ligation, the formation and stabilization of Pr and Pfr, and transmitting the light signal to the histidine kinase domain of the protein.

Prior mutational studies have identified a number of amino acids that are important for chromophore incorporation and Phy signaling. For example, the histidine directly preceding the cysteine responsible for covalent bilin attachment has been implicated as necessary for bilin ligation and phototransformation in plant phytochromes (Remberg et al., 1999, *Eur. J. Biochem.* 266: 201-208). A structurally conserved isoleucine (Ile35 in DrBphP, the bacteriophytochrome from *Deinococcus radiodurans*) near the N-terminus of the phytochromes has been implicated as important for protein solubility (Bhoo et al., 1997, *J. Amer. Chem. Soc.* 119: 11717-11718). To date, many phytochrome mutations have been generated via random mutagenesis screens. However, it would be advantageous to genetically engineer phytochrome mutations in a more predictable and logical manner. For instance, one or multiple directed amino acid substitutions can be useful to test the effects of size or charge at conserved sites.

Plant phytochromes can exhibit some fluorescence. Wild-type plant phytochromes, and the PAS-GAF-PHY construct from the cyanobacterial phytochrome (Cph) known as Cph1, are shown to be fluorescent with the non-natural linear tetrapyrrole phycoerythrobilin (Murphy and Lagarias, 1997, *Current Biology* 7: 870-876). For example, U.S. Pat. No. 6,046,014 describes "phytofluors", which are fluorescent adducts comprising an apoprotein and a bilin. Isolation of fluorescent Cph1 mutants recovered from a PHY domain mutant library was disclosed in Fischer and Lagarias, 2004, *Proc. Natl. Acad. Sci. USA* 101: 17334-17339.

Various methods and reporter molecules are available for monitoring gene activity and protein distribution within cells. These include the formation of fusion proteins with coding sequences for reporter molecules (markers) such as beta-galactosidase, luciferase, and green fluorescent protein. Particularly useful reporter is the Green Fluorescent Protein (GFP) from the bioluminescent jellyfish *Aequorea victoria*, which is frequently used as a fluorescent marker, and is described in U.S. Pat. No. 5,491,084. However, the known reporter molecules have a variety of limitations, including short wavelength of the fluorescence emission and small separation between excitation and emission wavelength maxima. The discovery of novel reporter molecules for monitoring gene activity, protein synthesis, and protein distribution within cells, can provide very useful tools for biotechnology applications. The present invention addresses these and related needs.

BRIEF SUMMARY

Isolated polynucleotides are provided that encode modified bacterial phytochrome domains with increased fluorescence over the corresponding wild-type bacterial phytochrome domains. The modified bacterial phytochrome domains include amino acid sequences that are at least 95% identical to SEQ ID NO:1, SEQ ID NO:2, SEQ ID NO:3, SEQ ID NO:4, SEQ ID NO:5, SEQ ID NO:6, SEQ ID NO:7, or SEQ ID NO:8. The isolated polynucleotides may encode modified bacterial phytochrome domains that include the amino acid sequence His-Ile-Pro (HIP).

Isolated polynucleotides are provided that encode modified bacterial phytochrome domains with increased fluorescence over the corresponding wild-type bacterial phytochrome domains, where the modified bacterial phytochrome domains comprise a mutation of the polypeptide sequence of bacterial phytochrome which is selected from the group consisting of: (i) mutations D207A, D207E, D207H, D207K, D207L, D207N, D207Q, D207S, and D207T from the phytochrome of *Deinococcus radiodurans*; (ii) mutations D84A, D84E, D84H, D84K, D84L, D84N, D84Q, D84S, and D84T from the phytochrome of *Synechococcus* OS A (also known as *Cyanobacterium Yellowstone* A, and also abbreviated as SyA); and (iii) mutations D86A, D86E, D86H, D86K, D86L, D86N, D86Q, D86S, and D86T from the phytochrome of *Synechococcus* OS B' (also known as *Cyanobacterium Yellowstone* B', and also abbreviated as SyB). The Dr phytochrome mutation may preferably be D207H. The SyA phytochrome mutation may preferably be D84H. The SyB phytochrome mutation may preferably be D86H.

Expression vectors are provided, which include: (a) the isolated polynucleotides described above, which encode modified bacterial phytochrome domains with increased fluorescence, and (b) regulatory sequences that are operably linked to these polynucleotides. The regulatory sequences may be promoters.

Isolated polypeptides are provided, which encode modified bacterial phytochrome domains with increased fluorescence over the corresponding wild-type bacterial phytochrome domains. The isolated polypeptides include amino acid sequences that are at least 95% identical to SEQ ID NO:1, SEQ ID NO:2, SEQ ID NO:3, SEQ ID NO:4, SEQ ID NO:5, SEQ ID NO:6, SEQ ID NO:7, or SEQ ID NO:8. The modified bacterial phytochrome domains may include the amino acid sequence His-Ile-Pro (HIP).

Isolated polypeptides are provided that encode modified bacterial phytochrome domains, which include mutations of the polypeptide sequences of bacterial phytochrome selected from the group consisting of: mutations D207A, D207E, D207H, D207K, D207L, D207N, D207Q, D207S, and D207T from the phytochrome of *D. radiodurans*; mutations D84A, D84E, D84H, D84K, D84L, D84N, D84Q, D84S, and D84T from the phytochrome of *Synechococcus* OS A; and mutations D86A, D86E, D86H, D86K, D86L, D86N, D86Q, D86S, and D86T from the phytochrome of *Synechococcus* OS B', where the modified bacterial phytochrome domains have increased fluorescence over the corresponding wild-type bacterial phytochrome domains.

Cells are provided, which include DNA molecules having regulatory elements from genes, other than genes encoding bacterial phytochromes, which regulatory elements are operably linked to DNA sequences from *D. radiodurans* or to DNA sequences from *Synechococcus* sp. OS Type A or to DNA sequences from *Synechococcus* sp. OS Type B', which DNA sequences encode modified bacterial phytochrome domains with increased fluorescence. The cells may include DNA sequences that include the isolated polynucleotides encoding modified bacterial phytochrome domains with increased fluorescence, which include the amino acid sequence His-Ile-Pro. The cells may include: (i) modified bacterial phytochrome domains that include a mutation of the polypeptide sequence of bacterial phytochrome selected from the group consisting of mutations D207A, D207E, D207H, D207K, D207L, D207N, D207Q, D207S, and D207T from the phytochrome of *D. radiodurans*; (ii) modified bacterial phytochrome domains that include mutations selected from the group consisting of mutants D84A, D84E, D84H, D84K, D84L, D84N, D84Q, D84S, and D84T from the phytochrome of *Synechococcus* sp. OS Type A; or (iii) modified bacterial phytochrome domains that include mutations selected from the group consisting of mutants D86A, D86E, D86H, D86K, D86L, D86N, D86Q, D86S, and D86T from the phytochrome of *Synechococcus* sp. OS Type B'. The cells may be selected from the group consisting of bacterial cells, yeast cells, fungal cells, plant cells, insect cells, nematode cells, animal cells, and human cells. The regulatory elements may be promoters. The cells may be *Escherichia coli* cells.

Methods for the production of modified bacterial phytochrome domains with increased fluorescence are provided. The methods include: a) culturing cells comprising DNA molecules having regulatory elements from genes, other than genes encoding bacterial phytochromes, which are operably linked to DNA sequences from *Deinococcus radiodurans* encoding modified bacterial phytochrome domains with increased fluorescence; and b) isolating and purifying the modified bacterial phytochrome domains with increased fluorescence so produced by the cells. The cells may be *Escherichia coli* cells. The methods may include adding fluorescent adducts to the cells.

Methods for selecting cells that express proteins of interest are provided. The methods include: a) introducing into the cells a first DNA molecule having a DNA sequence encoding the protein of interest and a second DNA molecule having a DNA sequence encoding a modified bacterial phytochrome domain from *Deinococcus radiodurans* or *Synechococcus* sp. OS Type A or *Synechococcus* sp. OS Type B' with increased fluorescence; b) culturing the cells resulting from step (a) under conditions permitting expression of the modified bacterial phytochrome domain with increased fluorescence and the protein of interest; and c) selecting the cultured cells which express the modified bacterial phytochrome domain with increased fluorescence, thereby selecting cells expressing the protein of interest. The first DNA molecule and the second DNA molecule may be linked. The methods may include adding fluorescent adducts to the cells. The cells may be selected from the group consisting of bacterial cells, yeast cells, fungal cells, plant cells, insect cells, nematode cells, animal cells, and human cells. The methods may include adding fluorescent adducts to the cells.

Methods for localizing proteins of interest in cells are also provided. The methods include: a) introducing into cells DNA molecules having a sequence encoding the protein of interest linked to a DNA sequence encoding a modified bacterial phytochrome domain from *Deinococcus radiodurans* or *Synechococcus* sp. OS Type A or *Synechococcus* sp. OS Type B' with increased fluorescence, such that the fusion protein produced by the cell will have the protein of interest fused to the modified bacterial phytochrome domain having increased fluorescence; b) culturing the cells under conditions permitting expression of the fused protein; and c) detecting the location of the fused protein, thereby localizing the proteins of interest in the cells. The methods may include adding fluorescent adducts to the cells. The cells may normally express the proteins of interest.

Methods for detecting expression of genes in cells are provided. The methods include: a) introducing into the cells DNA molecules having the gene sequences linked to DNA molecules encoding modified bacterial phytochrome domains from *Deinococcus radiodurans* or *Synechococcus* sp. OS Type A or *Synechococcus* sp. OS Type B' having increased fluorescence, such that regulatory elements of the genes control expression of the modified bacterial phytochrome domains with increased fluorescence; b) culturing the cells under conditions permitting expression of the genes; and c) detecting the expression of the modified bacterial phytochrome domains having increased fluorescence in the cells, thereby detecting expression of the genes in the cells. The methods may include adding fluorescent adducts to the cells.

Methods for producing fluorescent molecular weight protein markers are provided, which include: a) linking first DNA molecules encoding modified bacterial phytochrome domains from *Deinococcus radiodurans* or *Synechococcus* sp. OS Type A or *Synechococcus* sp. OS Type B' having increased fluorescence with second DNA molecules encoding known amino acid sequences that are in the same reading frame as the first DNA molecules; b) introducing the linked DNA molecules of step (a) into protein expression systems permitting the expression of fusion proteins comprising the modified bacterial phytochrome domains linked to the known amino acid sequences; c) recovering the fusion proteins expressed in step (b); and d) determining the molecular weight of the fusion proteins from step (c), thereby producing fluorescent molecular weight protein markers. The methods may include adding fluorescent adducts to the protein expression systems. The methods may further include purification of the expressed proteins.

DETAILED DESCRIPTION OF THE PRESENTLY PREFERRED EMBODIMENTS

Figure 1:
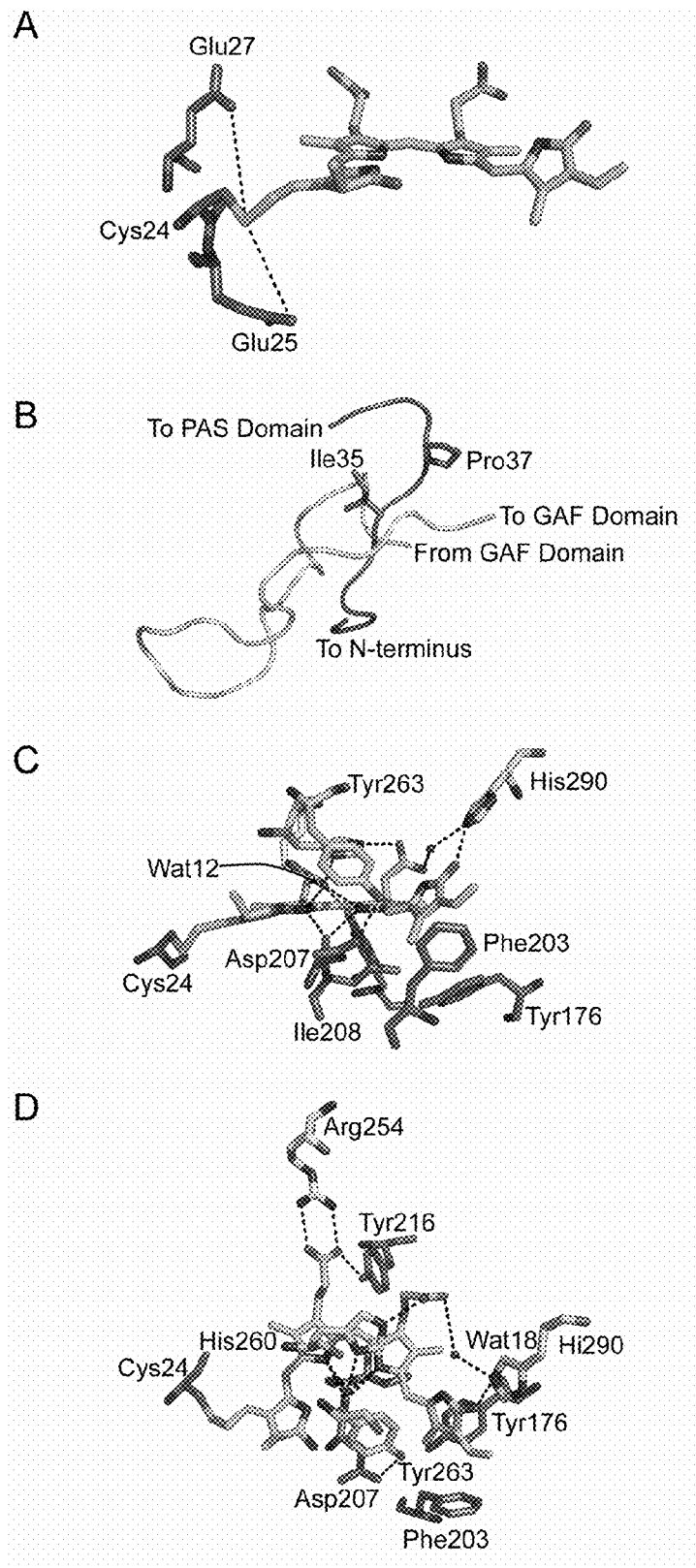
FIG. 1 shows molecular structures illustrating the locations of the DrBphP (*Deinococcus radiodurans* bacteriophytochrome) amino acid modifications (substitutions) described in the present application.

In one embodiment, the present invention provides compositions and methods that can be used as fluorescent molecules, i.e., fluorophores. Provided are modified phytochromes and modified phytochrome domains with increased fluorescence, which are suitable for use as fluorescent markers in a variety of applications. In another embodiment, the invention also provides the means to create molecules with increased fluorescence from phytochromes by targeted mutation of particular amino acid residues in certain phytochrome domains. Phytochrome domains from a variety of organisms may be used as starting points for modifications that will generate the fluorochromes of the present invention. Preferably, bacterial phytochrome domains are used as starting points for modifications that will generate the fluorochromes of the present invention. In certain preferred embodiments, the modified phytochrome domains are bacterial phytochrome domains. Modification of phytochromes and/or phytochrome domains can be performed by methods known in the art, e.g., site-directed mutations, additions, deletions, and/or substitutions of one or more amino acid residues of existing phytochromes and/or phytochrome domains. Alternatively, modified phytochromes and/or phytochrome domains can be synthesized de novo, for example by synthesis of novel genes that would encode phytochrome domains with desired modifications.

"Fluorescence" refers to luminescence that is caused by the absorption of radiation at one wavelength followed by nearly immediate reradiation usually at a different wavelength. The fluorescence typically ceases almost at once when the incident radiation stops. The compositions of the present invention typically fluoresce red when excited with ultraviolet (UV) light, although a variety of excitation wavelengths, including the visible part of the spectrum, may be used.

"Increased fluorescence" or "enhanced fluorescence" refers to an augmented change in the level or intensity of fluorescence. Specifically, the terms "increased fluorescence" or "enhanced fluorescence" refer to the difference in the level or intensity of fluorescence between a wild-type phytochrome domain and a phytochrome domain that is modified according to the present invention. Examples of such increased fluorescence include the following: (1) the fluorescence level or intensity of the proteins modified as described herein is increased above the level of that in wild-type protein; (2) the fluorescence level or intensity of the protein modified as described herein is in an organ, tissue or cell where it is not normally detected in wild-type, non-modified controls; (3) the fluorescence level or intensity of the proteins modified as described herein is present in an organ, tissue or cell for a longer period than in wild-type controls (i.e., the duration of activity of the fluorescence of the protein is increased).

The modified phytochrome domains of the present invention exhibit increased fluorescence over baseline fluorescence that may be present in wild-type phytochrome domains. For example, in the bacterial phytochrome of *Deinococcus radiodurans*, a substitution at amino acid residue 207 of a histidine (H) instead of wild-type aspartate (D) is highly fluorescent and exhibits an excitation and emission of 420 nm and 626 nm, respectively, with approximately 400,000 counts over background levels, as described below. In one example, increased fluorescence resulting from modification of a phytochrome domain refers to fluorescence intensity that is at least 50% greater than the fluorescence intensity of the corresponding wild-type phytochrome domain. In other examples, increased fluorescence resulting from modification of a phytochrome domain refers to fluorescence intensity that is at least 75%, 100%, 150%, 200%, 250%, 300%, 350%, 400%, or 450% greater than the fluorescence intensity of the corresponding wild-type phytochrome domain. In a preferred embodiment, increased fluorescence resulting from modification of a phytochrome domain refers to fluorescence intensity that is 500% greater than the fluorescence intensity of the corresponding wild-type phytochrome domain.

The term "fluorescent adduct" refers to compound formed between a fluorescent molecule (i.e., one capable of absorbing light of one wavelength and emitting light of a second wavelength) and a second molecule. For example, the peptides of the present invention may contain a chromophore binding domain that may form an adduct with a fluorescent molecule (e.g., bilins).

"Apoprotein" refers to polypeptides that have a hydrophobic pocket, referred to as chromophore binding site, capable of forming a fluorescent adduct with a bilin component. The term apoprotein encompasses both naturally occurring apoproteins and variant polypeptides derived through mutagenesis. A general discussion of apoprotein structure and function is provided in Quail et al., 1997, *Plant Cell Environ.* 20: 657-665.

"Bilin" components are linear polypyrroles (for example, di-, tri-, or tetrapyrroles) capable of fluorescing when associated with an apoprotein (such as apophytochrome). The bilins may be linear bilins that are made from heme by cleaving the ring, or cyclic bilins that are heme precursors (for example protoporphyrin IX alpha or PPIXa) and heme. In some embodiments, when PPIXa binds to BphP as in the HIP mutants of BphP, the phytochrome is fluorescent. Bilin components can be isolated from plants, algae, or cyanobacteria according to standard techniques. The bilin components can also be synthesized de novo.

"Chromophore binding domain" (CBD) refers to the apoprotein N-terminal subsequence of phytochrome. Typically, the chromophore binding domain in bacterial phytochromes includes PAS and GAF domains of phytochrome. In certain cyanobacterial phytochromes such as SyA and SyB, the chromophore binding domain typically includes a GAF domain, but does not include the PAS domain.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence. In the case of both expression of transgenes and inhibition of endogenous genes (e.g., by antisense or sense suppression) the inserted polynucleotide sequence need not be identical and may be "substantially identical" to a sequence of the gene from which it was derived.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

In the case where the inserted polynucleotide sequence is transcribed and translated to produce a functional polypeptide, because of codon degeneracy, a number of polynucleotide sequences will encode the same polypeptide. These variants are specifically covered by the term "polynucleotide sequence from" a particular gene. In addition, the term specifically includes sequences (e.g., full length sequences) that are substantially identical (determined as described below) with a gene sequence encoding a polypeptide of the present invention and that encode polypeptides or functional polypeptide fragments that retain the function of a polypeptide of the present invention, e.g., a modified bacterial phytochrome with increased fluorescence.

Optimal alignment of sequences for comparison may be conducted by methods commonly known in the art, for example by the search for similarity method described by Pearson and Lipman 1988, *Proc. Natl. Acad. Sci. USA* 85: 2444-2448, by computerized implementations of algorithms such as GAP, BESTFIT, BLAST, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST"), which is well known in the art (Karlin and Altschul, 1990, *Proc. Natl. Acad. Sci. USA* 87: 2267-2268; Altschul et al., 1997, *Nucl. Acids Res.* 25: 3389-3402), the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST programs can be used with the default parameters or with modified parameters provided by the user.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequences that encode the polypeptides of the present invention.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polypeptides or proteins of the present invention include amino acid sequences that have substantial identity to the amino acid sequences of the polypeptides of the present invention, which are modified bacterial phytochromes that exhibit increased fluorescence over the corresponding wild-type bacterial phytochromes.

The invention also relates to nucleic acids that selectively hybridize to the exemplified sequences, including hybridizing to the exact complements of these sequences. The specificity of single-stranded DNA to hybridize complementary fragments is determined by the "stringency" of the reaction conditions (Sambrook et al., 1989). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NO:1). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NO:1). One example comprises hybridization in 6×SSC, 5×Denhardt's solution, 0.5% SDS and 100 μg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency, such that a polynucleotide will hybridize to the entire, fragments, derivatives, or analogs of the target sequence (e.g., SEQ ID NO:1). A nonlimiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

A "functional homolog," "functional equivalent," or "functional fragment" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

The present invention contemplates the use of a modified phytochrome as a fluorophore. In general, any phytochrome with a DIP (Asp-Ile-Pro) motif may be used as to create a modified phytochrome with a HIP (His-Ile-Pro) motif, which can then be used as a fluorophore with improved fluorescence. For example, various bacterial phytochromes that have a DIP (Asp-Ile-Pro) motif may be used as starting points to create fluorophores with improved fluorescence. In one example, the present invention provides phytochromes with modified aspartate 207 (also called aspartic acid 207, Asp207, or D207) amino acid residue, which exhibit increased fluorescence. In one example, this aspartate 207 residue is located within the chromophore binding domain (CBD) of phytochrome of the bacterium *Deinococcus radiodurans*. Example of this is shown in the 3-D structure of the chromophore-binding domain of bacterial phytochrome of *D. radiodurans* (DrCBD), described by Wagner et al., 2005, *Nature* 438: 325-331. The amino acid sequence corresponding to the chromophore-binding domain of bacterial phytochrome isolated from *D. radiodurans* was deposited in the GenBank on May 27, 2005, under accession number 1ZTUA, and is shown as SEQ ID NO:1.

In one example, the present invention provides phytochrome D207 mutants of the bacterium *Deinococcus radiodurans*, which exhibit increased fluorescence. Non-limiting examples of phytochrome D207 mutants of *D. radiodurans* include D207A (i.e., modification of Asp to Ala), D207E (i.e., modification of Asp to Glu), D207H (i.e., modification of Asp to His), D207K (i.e., modification of Asp to Lys), D207L (i.e., modification of Asp to Leu), D207N (i.e., modification of Asp to Asn), D207Q (i.e., modification of Asp to Gln), D207S (i.e., modification of Asp to Ser), and D207T (i.e., modification of Asp to Thr). All of the above can be used as fluorophores in the practice of this invention. Particularly useful for the practice of the present invention is the modified phytochrome D207H. Functional homologs of these mutants can also be used as fluorochromes.

The present invention also provides modified phytochromes from *Cyanobacteria* as fluorophores with improved fluorescence. In one example, the modified phytochromes are from the thermophilic bacterium *Synechococcus* OS A or from *Synechococcus* OS B' (Steunou et al., 2006, *Proc. Natl. Acad. Sci. USA* 103: 2398-2403; Allewalt et al., 2006, *Appl. Environ. Microbiol.* 72: 544-550; Bhaya et al., 2007, *ISME J.* 1: 703-713). Similar to what is described above for modifications of phytochromes from *Deinococcus radiodurans*, it is possible to modify the corresponding aspartate in the DIP motifs of the *Synechococcus* OS A or *Synechococcus* OS B' chromoproteins, and thus obtain fluorophores with increased fluorescence and with similar fluorescence characteristics to those of the *D. radiodurans* mutation. Shown in SEQ ID NO:3 is the amino acid sequence of the full-length SyA-Cph1 protein of the bacterium *Synechococcus* sp. OS Type A. Shown in SEQ ID NO:5 is the amino acid sequence of the full-length SyB-Cph1 protein of the bacterium *Synechococcus* sp. OS Type B'. Not wanting to be bound by the following theory, this particular point mutation (DIP→HIP) might have a ubiquitous effect throughout the phytochrome superfamily, which contains a DIP motif.

In another example, the present invention contemplates the use of a modified GAF domain of phytochrome as a fluorophore. The GAF domain is present in phytochromes and in cGMP-specific phosphodiesterases. The present invention contemplates the use of modified GAF domains from both phytochromes and from cGMP-specific phosphodiesterases. The GAF domain of the *Deinococcus radiodurans* phytochrome described by Wagner et al., 2005, *Nature* 438: 325-331, is 165 amino acids long, consists of the phytochrome amino acid residues 166 to 330, and is shown in SEQ ID NO:2. The similar domain of the bacterium *Synechococcus* sp. OS Type A (also referred to herein as *Synechococcus* OS A, SyA, *Cyanobacterium Yellowstone* A, or CYA), encoding a CYA_2782 sensor histidine kinase, shown in SEQ ID NO:4, can be used in the practice of the present invention. In addition, the GAF domain of the bacterium *Synechococcus* sp. OS Type B prime (also referred to herein as *Synechococcus* OS B', SyB, *Cyanobacterium Yellowstone* B, or CYB), is shown in SEQ ID NO:7. In general, various phytochrome GAF domains, suitably modified according to the present invention, can be used as fluorophores with increased fluorescence. Functional homologs of various GAF domains can also be modified and used as fluorochromes.

In one embodiment, the present invention provides modified phytochrome domains from *Cyanobacteria* as fluorophores with improved fluorescence. In one example, the modified phytochrome domains are from the thermophilic bacterium *Synechococcus* OS A or from *Synechococcus* OS B' (Steunou et al., 2006, *Proc. Natl. Acad. Sci. USA* 103: 2398-2403; Allewalt et al., 2006, *App. Environ. Microbiol.* 72: 544-550; Bhaya et al., 2007, *ISME J.* 1: 703-713). Similar to what is described above for modifications of the GAF domain from *D. radiodurans* phytochrome, it is possible to modify the corresponding aspartate in the DIP motifs of the *Synechococcus* OS A or *Synechococcus* OS B' chromoproteins, and thus obtain fluorophores with similar fluorescence characteristics to those of the *D. radiodurans* mutation. Not wanting to be bound by the following theory, this particular point mutation (DIP→HIP) might have a ubiquitous effect throughout the phytochrome superfamily, which contains a DIP motif.

Various fragments of the GAF domain can be used as fluorescent molecules of the present invention. Particularly useful for practicing the present invention is the modification of the Asp-Ile-Pro (i.e., DIP) motif present in the GAF domain of the *Deinococcus radiodurans* phytochrome, shown in amino acids 207-209 of SEQ ID NO:1, i.e., amino acids 56-58 of SEQ ID NO:2, into a His-Ile-Pro (i.e., HIP) motif. It is contemplated that various modifications of this DIP motif (and its functional equivalents in other phytochromes) will result in fluorophores useful for practicing the present invention. Some examples of fluorophores useful for the practice of this invention include modifications of the DIP motif of the GAF domain, for example: Asp to Ala (i.e., D→A); Asp to Glu (i.e., D→E); Asp to His (i.e., D→H); Asp to Lys (i.e., D→K); Asp to Leu (i.e., D→L); Asp to Asn (i.e., D→N); Asp to Gln (i.e., D→Q); Asp to Ser (i.e., D→S); and Asp to Thr (i.e., D→T).

A variety of modified phytochrome domains can be used as fluorescent compositions of the present invention. In general, what is important is that the polypeptides used as fluorophores include modifications of the Asp (D) indicated above, or its equivalents in other phytochromes. In one example, preferred modifications include modifications of the DIP motif indicated above or its equivalents in other phytochromes. The amino acid chains surrounding the one or more introduced modifications can vary in length; they can be symmetrical or asymmetrical. Thus, a variety of functional homologs of these polypeptides can be used as fluorochromes in the practice of this invention. For example, SEQ ID NO:8 illustrates an attenuated GAF domain from *Synechococcus* OS B', 154 amino acids long, which can be modified (for example, by introducing a mutation in the GAF domain of D86 to H86, i.e. D86H) and used as a fluorochrome in the practice of this invention.

Examples of wild-type phytochrome domains that can be modified and used in the practice of this invention are shown in SEQ ID NO:7 (CYB GAF), which is 200 amino acids long, and in SEQ ID NO:6 (CYB GAF-PHY), which is 421 amino acids long. In addition, a variety of attenuated CYB GAF domains can be used as starting points for modifications that can generate phytochrome-based fluorochromes. An example of one such attenuated GAF domain is shown in SEQ ID NO:8, where the attenuated GAF domain is 154 amino acids long. Functional equivalents of these phytochrome domains can also be used as starting point for modifications, to generate fluorochromes according to this invention.

In another example, the present invention contemplates the use of a modified GAF phytochrome domain fused to the phytochrome domain PHY, as a fluorophore. The PHY domain is located at the C-terminal end of the photosensory domain (Oka et al., 2004, *Plant Cell* 16: 2104-2116). The addition of the PHY domain to the modified GAF phytochrome domain can stabilize the fluorescence of the compositions of the present invention. In examples where the GAF construct may lose the intensity of fluorescence with UV exposure, the addition of PHY can stabilize the intensity of fluorescence. If desired, additional modifications of the phytochrome domains can be performed; for example, additional amino acid residues may be added to the modified constructs, to improve the stability of the compositions of the present invention, and/or their fluorescence intensity, to minimize photobleaching, etc. As well, additional protein domains can be fused to the modified phytochrome domains.

Since phytochromes with the Asp207>H is mutation or the parallel equivalent need a fluorescent adduct to emit fluorescence, a phytofluor or an equivalent fluorescent adduct is typically provided. Fluorescent adducts such as phytofluors are known in the art (Murphy and Lagarias, 1997, *Current Biology* 7: 870-876). The fluorescent adducts are not necessarily limited to the native bilin, i.e., phycocyanobilin (PCB) for cyanobacteria Cphs and Biliverdin for Bphs, but may be any adduct which emits fluorescence as a result of binding the apoprotein (covalently or non-covalently). The fluorescent adducts are not necessarily limited to linear bilins (i.e., PCB) and can use cyclic bilins such as PPIXa. These fluorescent adducts may also be linked covalently by crosslinking techniques known in the art. The present invention contemplates fluorescent adducts consisting in some embodiments of naturally occurring or engineered apoproteins with bilins derived from different organisms, or with non-naturally occurring synthetic pyrroles.

The fluorescent adduct can be provided in a variety of ways, for example as a co-expressed entity within the system being used (e.g., co-expression of heme oxygenase with a bacterial phytochrome or BphP to make the native biliverdin chromophore), or added exogenously to the apoprotein (for example making bacterial agar plates with biliverdin in the medium to be taken into bacterial cells expressing the Asp207>His apoprotein for fluorescent bacterial colony recognition). To enable fluorescence, one or more types of fluorescent adducts may be also be added to cell culture, tissue slices, or even given to a live animal to enable the fluorescent adduct to be formed. The manner in which the fluorescent adduct is provided is irrelevant to the present invention. Alternatively, the cell or the living organism may natively provide the fluorescent adduct.

It is also important to note that the fluorescence emission wavelength may also be subject to alteration based on either further engineering the apoprotein, the use of a different fluorophore, or a combination of both. U.S. Pat. No. 6,046, 014, incorporated herein by reference, also gives several useful examples of this system, including protein-protein interactions with yeast 2-hybrid using a Phy apoprotein fusion as "bait" for a GFP-fusion as prey. The phytofluor would be added to the system to generate fluorescence energy transfer from the now fluorescent Phy to GFP to enable the detection of the interaction.

Another powerful example of how this technology can be used includes making Asp207>His apoprotein antibody conjugation, followed by detection by the addition of any number of phytofluors. This can also be useful in tracing protein expression in vitro, in situ, in cells, or even in a living organism. Such conjugates may be used in a number of ways to screen for interactions using a high-throughput microtiter plate assay, where the D207>His apoprotein-target fusion is simply detected by addition of the fluorescent adduct (phytofluor).

The fluorophores may also be provided by injection (for example injection into oocytes to monitor expression of a D207>His apoprotein fusion protein).

The invention is particularly useful because the modified phytochromes and phytochrome domains exhibit relatively long wavelength of the fluorescence emission. In general, the novel fluorophores of this invention exhibit fluorescence in the red part of the visible light spectrum. Some of the modified phytochrome domains described herein have emission wavelengths far into the red part of the visible light spectrum, for example as far to the red part of the spectrum as 720 nm. These values exceed the examples of other fluorescent molecules with long wavelength of emission, for example mPlum, with emission max at 649 nm (Wang et al., 2004, Proc. Natl. Acad. Sci. USA 101: 16745-16749; and Shaner et al., 2004, Nature Biotechnology 22: 1567-1572). In addition, the modified phytochrome domains exhibit large separation between the excitation and emission wavelength maxima, which makes them particularly useful.

This invention contemplates the use of phytochrome fluorophores as components of fusion proteins. A "fusion protein" is a protein created through genetic engineering from two or more proteins or peptides. This is typically achieved by creating a fusion gene: removing the stop codon from the DNA sequence of the first protein, then appending the DNA sequence of the second protein in frame. The entire DNA sequence (encoding the first and the second protein) will then be expressed by a cell as a single protein (i.e., fusion protein). Optionally, one or more amino acids in the form of a linker (or "spacer") can also be added between the fused proteins or peptides.

In some embodiments, this invention contemplates the use of a single amino acid modification for improvement of fluorescent properties of the compositions described herein. For example, a composition of the present invention may include a phytochrome domain with just a DrBphP D207 mutation as described herein. Alternatively, this invention contemplates the use of multiple amino acid modifications for improvement of fluorescent properties of the compositions described herein. For example, a composition of the present invention may include a phytochrome domain with a D207 mutation and one or more other amino acid mutations as described herein. Two or more modified phytochrome domains may be combined, for example fused into a fusion protein.

The modified phytochromes of the present invention have the potential to be expressed as apoproteins and can be detected by exogenous addition of native or synthetic fluorophores (e.g., PCB or Cy5 derivatives). Labeling of fusion proteins with synthetic fluorophores is known in the art (Keppler et al., 2004, Proc. Natl. Acad. Sci. USA 101: 9955-9959). Alternatively, such mutated phytochromes can be co-expressed with bilin derivatives in vivo.

Methods for detecting expression of genes in living organisms are provided. The methods include: a) introducing into cells of the living organisms DNA molecules having the gene sequences linked to DNA molecules encoding modified bacterial phytochrome domains from *Deinococcus radiodurans* or *Synechococcus* sp. OS Type A or *Synechococcus* sp. OS Type B' having increased fluorescence over the corresponding wild-type bacterial phytochrome domains, such that regulatory elements of the genes control expression of the modified bacterial phytochrome domains with increased fluorescence; b) culturing the cells under conditions permitting expression of the genes; and c) detecting the expression of the modified phytochrome domains with increased fluorescence in the cells, thereby detecting expression of the genes in the living organisms. The methods may include adding fluorescent adducts to the cells of the living organisms.

Methods for determining the tissue-specificity of transcription of DNA sequences in living organisms are provided. The methods include: a) introducing into cells of the living organisms first DNA molecules that include the DNA sequences that are linked to other DNA sequences encoding modified bacterial phytochrome domains; having increased fluorescence from *Deinococcus radiodurans* or *Synechococcus* sp. OS Type A or *Synechococcus* sp. OS Type B', such that the first DNA sequences control expression of the modified bacterial phytochrome domains having increased fluorescence in the living organisms; and b) detecting expression of the modified bacterial phytochrome domains with increased fluorescence in different tissues of the living organisms, thereby determining the tissue-specificity of the transcription of the first DNA sequences in the living organisms. The methods may include adding fluorescent adducts to the tissues.

The photocycle properties of some phytochrome domains have been studied. For example, even though GAF can undergo photocycle, when this fragment is expressed alone, it cannot incorporate chromophore (Esteban et al., 2005, Biochemistry 44: 450-461). As well, there have been mutations made at Asp207 or its equivalent DIP position to interrogate the role of that residue in photoconversion. For example, these are described by Hahn et al., 2006, FEBS J. 273: 1415-1429 2006, where the modified residues were D207A and D207N/E196G; and by von Stetten et al., 2007, J. Biol. Chem. 282: 2116-2123, where the modified residues were Asp-197 (D197A) and His-250. Neither of these publications has any fluorescence mention. In addition, photocycle properties of phytochromes are not the focus of the present invention. The present invention provides compositions and methods that relate to modified phytochromes with increased fluorescence.

In contrast to other widely used fluorescent reporters (for example, Green Fluorescent Protein), which typically allow only for C-terminal protein fusions, the compositions of the present invention allow for making both C-terminal protein fusions and N-terminal protein fusions. For example, the SyB-Cph1 phytochrome (from thermostable *Cyanobacterium Yellowstone* B'; also known as SyB) lacks the N-terminal PAS domain which has been shown to prevent N-terminal fusions. Therefore, modified phytochromes according to this invention lend itself well to the creation of both C-terminal protein fusions and N-terminal fusion proteins with improved fluorescence. The SyB-Cph1 and SyB-Cph2 chromopeptides are very small and may be more desirable than larger fusions when used in genetic engineering applications. In addition, in contrast to GFP, the fluorophores of the present invention do not require oxygen, which makes them particularly useful for anaerobic applications. Thus, the invention provides greater flexibility for genetically engineering protein fusions that include fluorescent reporter molecules.

The present invention contemplates the use of the fluorophore compositions and the methods for a variety of applications, including but not limited to: tracking molecule movements in living cells by microscopy; high-throughput detection of molecules in plate-based or chip assays; detection of protein-protein interactions (e.g., FRET—Fluorescence Resonance Energy Transfer); and nanotechnology applications such as single-molecule measurements of biomolecular motion. The invention is particularly useful because in some embodiments of the invention the modified phytochromes and phytochrome domains may be thermotolerant, withstanding temperatures exceeding 70° C., and thus may find utility in applications where other fluorescent reporter molecules are less useful.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Example 1

Phytochrome-Based Fluorophores from *Deinococcus radiodurans*

Site-Directed Mutagenesis and Protein Purification.

The full-length DrBphP gene from *Deinococcus radiodurans* (encoding 755 amino acids) was PCR-amplified from genomic DNA using primers designed to introduce BamHI and XhoI sites before and after the designated length of coding region, respectively. The BamHI-XhoI-digested PCR products were cloned into pET21a(+) (Novagen, San Diego, Calif.), which was similarly digested, resulting in the addition of codons for a T7 tag N-terminal to the protein and codons for a His6 tag before the stop codon. All site-directed mutations were introduced by the PCR-based QuikChange method (Stratagene, La Jolla, Calif.). Each coding region was sequenced completely by the dideoxy method to confirm introduction of the appropriate mutation.

The DrBphP plasmids were transformed into *E. coli* strain Rosetta (DE3) (Novagen) containing the Synechocystis Heme Oxygenase (HO) gene in pET 24a(+) (Novagen) (Bhoo et al., 2001, *Nature* 414: 776-779). For protein expression, 1 L cultures of the transformed *E. coli* were grown in a shaking incubator set to 37° C. and 225 rpm. When the cultures reached an OD600 of ~0.5, protein expression was induced with 1 mM isopropyl-beta-D-thiogalactopyranoside (IPTG) for 4 h at room temperature in a shaking incubator set to 100 rpm. The cells were then harvested by centrifugation at 8000×g for 10 min.

After pelleting the cells, all further steps were carried out in a darkroom under green safe lights. Cells were lysed via sonication and cleared with a 30 min centrifugation at 18,000×g. To encourage complete chromoprotein assembly, the crude soluble extracts were incubated in darkness for one hour in at least a 10-fold molar excess of BV (biliverdin) prior to affinity purification. The holoproteins were then purified via nickel chelate affinity chromatography and eluted with a 30 mM Tris-HCl (pH 8.0) buffer containing 1 M imidazole. After elution, the buffer was exchanged for 30 mM Tris-HCl (pH 8.0) by ultrafiltration using a Centricon YM-10 column (Millipore, Billerica, Mass.). The ability of proteins to covalently bind BV was monitored by zinc-induced fluorescence of the chromoproteins following SDS-PAGE, as described by Bhoo et al., 2001, *Nature* 414: 776-779.

Spectrophotometric Analysis.

Pr/Pfr spectroscopy was performed with a Beckman DU-640B spectrophotometer. All proteins were diluted with 30 mM Tris-HCl (pH 8.0) so that the Pr peak at ~700 nm had an absorbance between 0.25 and 0.6. Ground state (Pr) spectra were obtained for all proteins following an extended incubation in the darkness. After the Pr spectrum was obtained, the sample was irradiated with red light R (690 nm) until changes in absorbance were no longer detected. Afterwards, the saturated R-irradiated spectrum was recorded. Difference spectra were calculated by subtracting the R-irradiated spectrum from the Pr spectrum.

Fluorescence spectroscopy analysis of the Asp207 mutations was performed at the UW-Madison Biophysics Instrumentation Facility using a QuantaMaster Model C-60/2000 spectrofluorimeter (Photon Technologies International, Birmingham, N.J.) with both monochromaters set to a 4 nm band pass. Holoprotein assembly and photochemical characteristics of the DrBphP constructions that were analyzed are presented in Table 1.

TABLE 1

Photochemical properties of DrBphP constructions

| Construction | BV Covalent Attachment | Absorbance at 280 nm | Pr $\lambda_{Max}$ (nm) | Pr Absorb. Max | R-irradiated $\lambda_{Max}$ (nm) | Photo-conversion | UV Fluorescence |
| --- | --- | --- | --- | --- | --- | --- | --- |
| WT | Yes | 0.556 | 700 | 0.478 | 751 | Pr/Pfr | No |
| E25/27A | Yes | 1.747 | 698 | 0.552 | 751 | Pr/Pfr | No |
| I35A | No | 0.376 | 699 | 0.036 | 751 | Intermediate | N/A |
| P37A | Yes | 0.481 | 701 | 0.269 | 753 | Pr/Pfr | No |
| Y176H | Yes | 1.709 | 696 | 0.502 | 750 | Intermediate | No |
| F203A | Yes | 1.068 | 696 | 0.507 | 738 | Intermediate | Yes |
| F203H | Yes | 1.669 | 695 | 0.556 | 742 | Intermediate | Yes |
| F203W | Yes | 1.625 | 701 | 0.566 | 751 | Pr/Pfr | No |
| D207A | Yes | 0.999 | 700 | 0.268 | 751 | Intermediate | Yes |
| D207E | Yes | 0.701 | 701 | 0.464 | 751 | Intermediate | Yes |
| D207H | Yes | 1.855 | 700 | 0.385 | 739 | Locked in Pr | No |
| D207K | Yes | 0.815 | 700 | 0.531 | 739 | Locked in Pr | Yes |
| D207L | Yes | 0.756 | 700 | 0.512 | N/A | Locked in Pr | Yes |
| D207N | Yes | 0.968 | 700 | 0.356 | 751 | Intermediate | Yes |
| D207Q | Yes | 0.795 | 701 | 0.508 | 746 | Intermediate | Yes |
| D207S | Yes | 2.282 | 697 | 0.299 | 746 | Locked in Pr | No |
| D207T | Yes | 1.036 | 704 | 0.479 | 751 | Intermediate | Yes |
| I208A | Yes | 0.888 | 695 | 0.508 | 751 | Pr/Pfr | No |
| Y216H | Yes | 0.87 | 697 | 0.541 | 748 | Pr/Pfr | No |
| Y216W | Yes | 3.026 | 698 | 0.289 | 751 | Intermediate | N/A |
| R254A | Yes | 2.391 | 700 | 0.514 | 750 | Pr/Pfr | No |
| R254K | Yes | 0.742 | 701 | 0.499 | 750 | Pr/Pfr | No |
| Y263H | Yes | 1.046 | 698 | 0.543 | 742 | Intermediate | Yes |
| H290N | Yes | 0.981 | 699 | 0.573 | 747 | Intermediate | Yes |
| H290Q | Yes | 0.333 | 699 | 0.476 | 746 | Intermediate | Yes |

Generation of Mutants.

The examples of the present invention include 25 substitution mutations at 10 conserved positions in the CBD of DrBphP. These residues included Glu25 and Glu27, which may be important in chromophore ligation (FIG. 1A), Ile35 and Pro37 which are near the knotted interface of the CBD and may play a role in polypeptide folding (FIG. 1B), and Tyr176, Phe203, Ile208, Asp207, Tyr216, Arg254, Tyr263, and His290, which line the bilin binding pocket and therefore may be important for photoconversion (FIGS. 1C, D).

Since the DRCBD alone does not photoconvert from Pr to Pfr but instead appears to become trapped in a bleached intermediate (Karniol et al., 2005, *Biochem. J.* 392: 103-116), all of the amino acid substitutions were introduced into the full-length DrBphP polypeptide. By doing so, it was possible to test a full range of photochemical properties, including bilin binding, photoconversion, and dark reversion. While several of the DrBphP mutants exhibited near normal assembly and photochemical properties, the majority failed to properly photoconvert from Pr to Pfr even though the polypeptides could bind BV.

In some instances, several amino acid changes (i.e., modifications, mutations) were made at a single position. Some of these positions withstood conserved mutations and behaved normally, while one in particular, Asp207, failed to tolerate even conserved substitutions, exhibiting irregular photochemistry for every residue tested. Given the position of Asp207 near the A-, B-, and C-ring pyrrole nitrogens, it has been proposed that Asp207 participates in phototransformation by accepting a proton from BV during the Phy photocycle (Borucki et al., 2005, *J. Biol. Chem.* 280: 34358-34364). In support, Resonance Raman analysis of several of the Asp207 substitutions indicated that even after prolonged exposure to R, the chromophore remained protonated, and thus prevented photoconversion.

FIG. 1 illustrates the locations of the DrBphP amino acid substitutions described herein. FIG. 1(A): the side chains of Glu25 and 27 are near the sulfur moiety of Cys24 which is responsible for covalently binding BV. FIG. 1(B): Ile35 is in the center of the lasso formed by the GAF domain insertion; Pro37 is positioned near the beginning of the PAS domain. FIG. 1(C): positions of the conserved residues within the bilin binding pocket that were substituted to test their effects on bilin ligation and photochemistry. FIG. 1(D): positions of conserved residues in the GAF domain rotated approximately 90° with respect to FIG. 1(C); dashed lines in each pane indicate possible electrostatic interactions.

Figure 2:
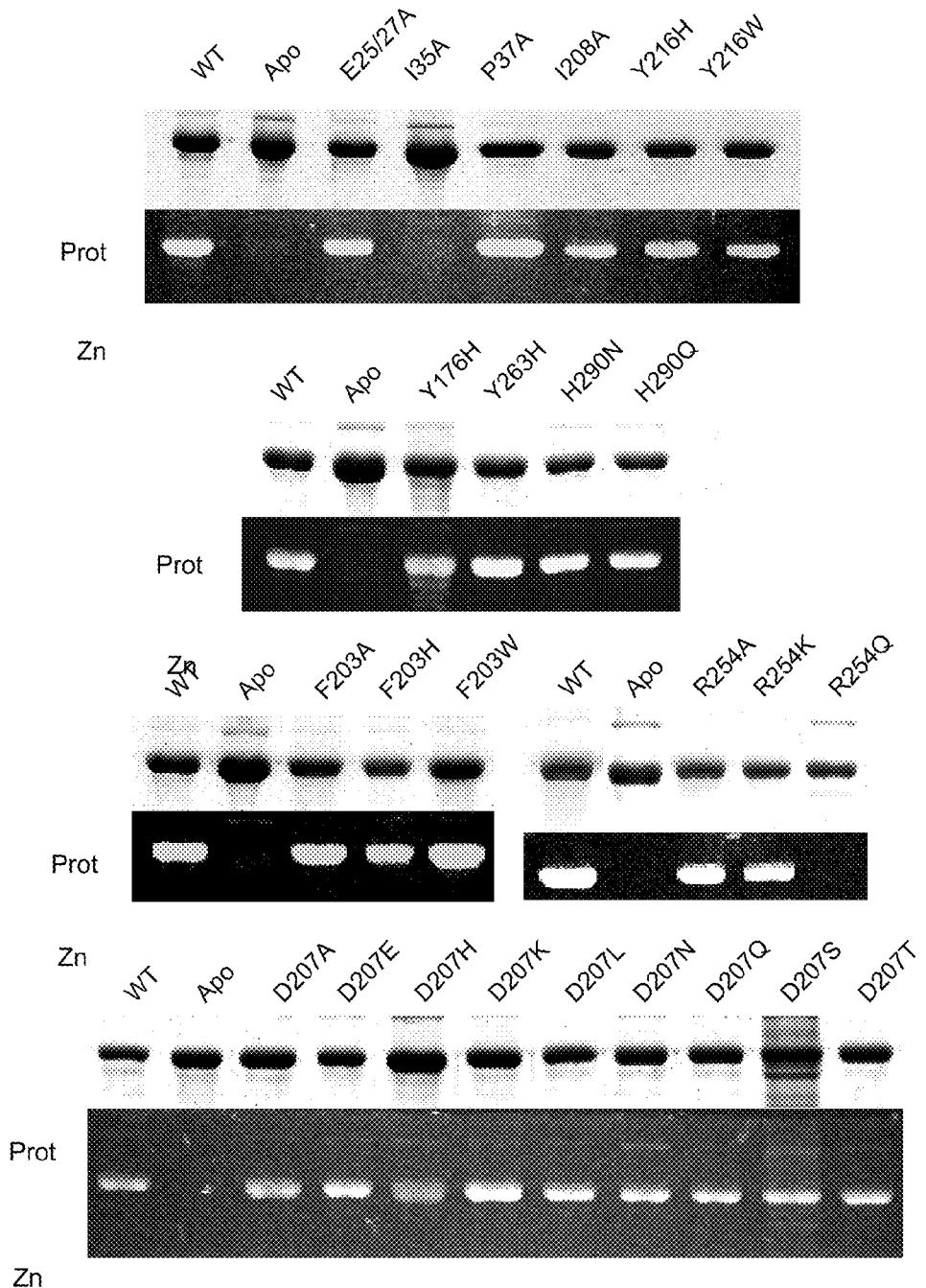
FIG. 2 shows electrophoretic images illustrating the bilin binding efficiency of DrBphP mutants.

FIG. 2 illustrates the bilin binding efficiency of DrBphP mutants. The recombinant wild-type (WT) and mutant polypeptides were incubated with BV for 30 min and purified by nickel chelate chromatography. Samples were subjected to SDS-PAGE and either assayed for the bound bilin by zinc-induced fluorescence (Zn) or stained for protein with Coomassie Blue (Prot). Apo, apoprotein prior to BV incubation.

Figure 3:
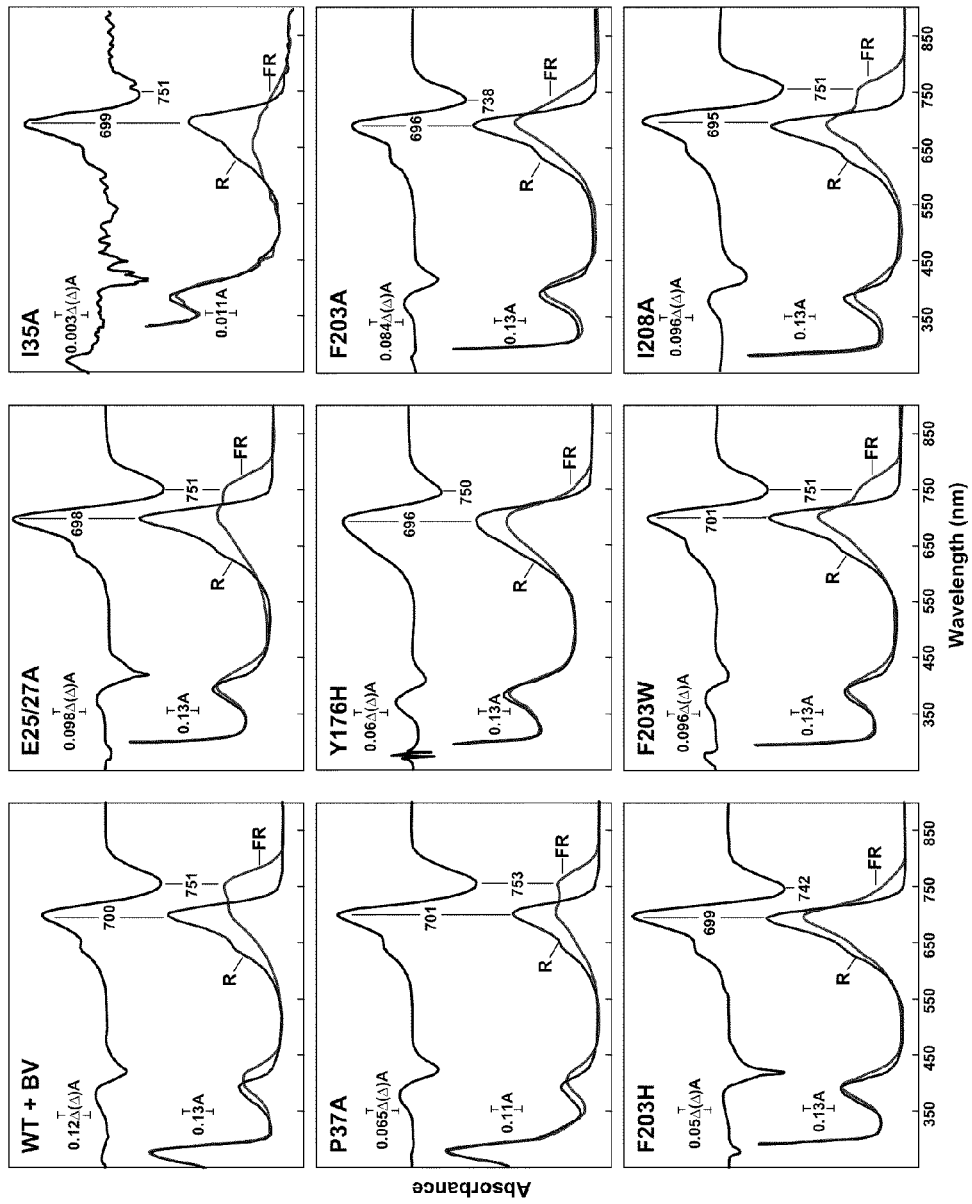
FIG. 3 shows graphs illustrating the spectral characteristics of DrBphP mutants.

FIG. 3 illustrates the spectral characteristics of various DrBphP mutants. Pr (blue) and Pfr (red) absorption spectra (lower graphs in each panel) and difference spectra (upper graph in each panel) of the apoproteins incubated with BV are shown. Pr absorption spectra were recorded after an extended period of darkness. Pfr spectra were recorded after saturating radiation with 690 nm light enriched with interference filters. Difference spectra were calculated by subtracting the Pfr spectra from the Pr spectra. Absorption maxima and minima are indicated.

Resonance Raman Analysis.

Resonance Raman spectra of wild-type (WT-DrBphP), and mutants D207A, D207E, and D207H were obtained with 1064-nm excitation at low temperature (−140° C.) as described elsewhere (Mroginski et al., 2004, *J. Am. Chem. Soc.* 126: 16734-16735). Vibrational spectra were obtained by density functional theory (DFT) using the B3LYP functional (Becke, 1993, *J. Chem. Phys.* 98: 5648-5652) and the 6-31G* basis set. The force field was scaled by a set of global scaling factors determined for a series of model compounds including hydrogen bonded systems (Magdo et al., 1999, *J. Phys. Chem. A* 103: 289-303; Mroginski et al., 2000, *J. Phys. Chem. B* 104: 10885-10899). This approach provides an accuracy of ±11 cm$^{-1}$ for the calculated frequencies.

Modification of Glutamate 25 and 27.

Though much information was obtained from the 3D structure of DrCBD (Wagner et al., 2005), the mechanism for chromophore attachment was unclear. Two glutamic acid residues (Glu25 and 27) are relatively close to Cys24 and may play a role in activating the Cys24 sulfur for hydrophilic attack of the A-ring vinyl group of BV (FIG. 1). These two glutamates were replaced by alanines (E25/27A) to test their importance in holoprotein assembly.

When incubated with BV the E25/27A mutant still covalently bound BV effectively, as judged by zinc-induced fluorescence (Table 1 and FIG. 2). E25/27A was also able to photoreversibly generate Pr and Pfr, though the photoequilibrium for the mutant was slightly shifted in favor of Pr (FIG. 3). Collectively, these results indicate that Glu25 and Glu27 are not necessary for bilin attachment and may play a small role in photo-interconversion.

Modification of Isoleucine 35.

Isoleucine 35 is in the center of the lasso formed by the GAF domain insertion (FIG. 1) and is necessary for the proper folding of apo-Phy (Karniol and Vierstra, 2006, In: *Photomorphogenesis in Plants and Bacteria: Function and Signal Transduction Mechanisms*, Springer, Dordrecht, The Netherlands, pp 65-98). For example, when the corresponding isoleucine residue is substituted with an alanine in pea phyA and *Agrobacterium tumefaciens* BphP2, the resulting polypeptides were insoluble and failed to bind chromophore either in vivo or in vitro (Bhoo et al., 1997; Karniol and Vierstra, 2006).

An Ile35→Ala (I35A) substitution in DrBphP also fails to covalently bind BV (Table 1 and FIG. 2). However, it was still able to interact with BV in a noncovalent manner and generate a Pr conformer that has an absorption maximum at 699 nm. The amount of Pr was dramatically reduced as compared to unmodified DrBphP implying that the efficiency of bilin binding was much lower (FIG. 3). When irradiated with R, the I35A construction produces an absorption spectrum similar to bleached intermediates of the Phy photocycle, implying that upon R-irradiation, the Ile35 mutation is trapped in a photocycle intermediate. Based on these results and the position of Ile35 in the center of the GAF-inserted lasso, it appears that this residue is important for chromophore attachment and polypeptide folding.

Modification of Proline 37.

Proline 37 is often conserved within the Phy superfamily and is located at the tip of the loop directly preceding the PAS domain, as shown in FIG. 1, and described by Karniol et al., 2005; Wagner et al., 2005. The position of this residue suggests that it plays a role in proper folding of DrBphP around the knot region. An alanine substitution at this position (P37A) was able to bind BV, and form a spectrally active holoprotein with near normal Pr and Pfr absorption maximum (Table 1 and FIGS. 2 and 3). Because position 37 is in a loop region of the protein, it can likely withstand a variety of mutations.

Modification of Tyrosine 176 and Tyrosine 263.

Tyrosines 176 and 263 lie above and below the D ring of BV (FIGS. 1C, D) (Wagner et al., 2005). Tyr176 is necessary for proper photoconversion in a cyanobacterial Phy (Cph) from *Synechocystis* PCC6803 (Sy) (Fischer and Lagarias, 2004, *Proc. Natl. Acad. Sci. USA* 101: 17334-17339). Tyr263 may also play a role in photoconversion because it is near the D ring and is also predicted to form a hydrogen bond with the carboxylate of Asp207. To test the role(s) that these two tyrosines play in the photoconversion of DrBphP, they were substituted with histidines (Y176H and Y263H). Both mutants were able to covalently bind BV to generate Pr (Table 1, FIG. 2). While the Pr absorption spectrum of Y263H was normal, the Pr absorption spectrum of Y176H was much more broad in the R region with an absorption maximum at 696 nm (Table 1, FIGS. 3, 5), implying that Tyr76 in DrBphP is necessary for normal Pr formation. When irradiated with R, both constructions photoconverted poorly to Pfr (Table 1, FIGS. 3, 5) indicating that both Tyr176 and Tyr263 are necessary to stabilize the Pfr conformer.

When exposed to UV light (UV), the Y176H mutation in SyCph1 fluoresces red (Fischer and Lagarias, 2004, *Proc. Natl. Acad. Sci. USA* 101: 17334-17339), which is an indication it cannot complete Pr to Pfr photoconversion. Unlike the Y176H substitution in SyCph1, the Y176H substitution in DrBphP failed to fluoresce under UV; however, Y263H did fluoresce, suggesting that Tyr263 in DrBphP may play a role similar as Tyr176 in SyCph1. These results suggest that Tyr176 does not fulfill the same roles in BphPs and Cphs, and that because they exhibit similar phenotypes, Tyr263 may perform the same roles in BphPs as Tyr176 does in Cphs.

Modification of Phenylalanine 203.

In the Pr conformer of DrBphP, the phenylalanine at position 203 forms part of the hydrophobic pocket that interacts with the D-ring vinyl and methyl side chains (FIGS. 1C,D). This phenylalanine was replaced by alanine (F203A) to abolish the contacts to the D ring, histidine (F203H) to change the electrochemical environment around the D ring, or tryptophan (F203W) to determine if a bulky hydrophobic residue can compensate for a phenylalanine.

All three mutations were able to covalently bind BV and form a near normal Pr absorption spectrum (Table 1, FIGS. 2, 3). When Phe203 was replaced with either histidine or alanine there was a slight blue shift in the Pr absorbance maxima (FIG. 3). This shift in absorbance may be the effect of torsional strain on the π conjugation system of BV. It is possible that the void of atoms in the F203A mutant shrinks the pocket surrounding the D ring, thus forcing it to assume a new position. In F203H, the blue shift in absorption could be due to charge repulsions between itself and the hydrophobic side chains of the D ring. F203A and F203H had similar R-irradiated spectra with both mutations forming a bleached intermediate after saturating R (FIG. 3), indicating that these two mutants fail to properly photoconvert to Pfr. As further proof that these two mutants have abnormal photochemistry, both fluoresced red when exposed to UV indicating that energy absorbed by R cannot drive phototransformation and is instead released as light. Unlike F203A and F203H, F203W generated a Pr absorbance spectrum with a peak at 700 nm and though not as robust as WT, F203W appeared to form Pfr with a maximum absorption of 750 nm (FIG. 3). These results imply that a hydrophobic residue at position 203 assists in Pr to Pfr photoconversion.

Modification of Aspartate 207.

Aspartate 207 is located in the highly conserved Asp-Ile-Pro (or DIP) motif in the GAF domain of Phys and is responsible for forming part of the bilin binding pocket (FIGS. 1C, D). Asp207 in SyChp1 is necessary for the formation of Pfr (Hahn et al., 2006, *FEBS J.* 273: 1415-1429). The DRCBD structure revealed that the main chain oxygen of Asp207 is within hydrogen binding distance to the pyrrole nitrogens of rings B and C of BV, while its carboxylate side chain may form an interaction with Tyr263. In addition, the carboxylate side chain of Asp207 is positioned near the A-ring carbonyl and may provide the repulsive force causing the torsional strain that rotates the A ring out of the plane formed by rings B and C.

In separate experiments, Asp207 was changed to: alanine (D207A), glutamic acid (D207E), histidine (D207H), lysine (D207K), leucine (D207L), asparagine (D207N), glutamine (D207Q), serine (D207S), or threonine (D207T). These residues were chosen for a variety of reasons. The alanine mutation was chosen to abolish any contacts to the chromophore at this position, while glutamic acid, asparagine, and glutamine were chosen because they are most similar to Asp and would test the importance of size and charge at position 207. Serine and threonine were chosen because their hydrophilic side chains would alter the hydrogen bonding patterns in the pocket. Histidine and lysine were chosen to test the effects positive charge would have on bilin ligation and photochemistry. Lastly, the leucine substitution was chosen because it is close to the same size as aspartic acid, but is hydrophobic.

Figure 4:
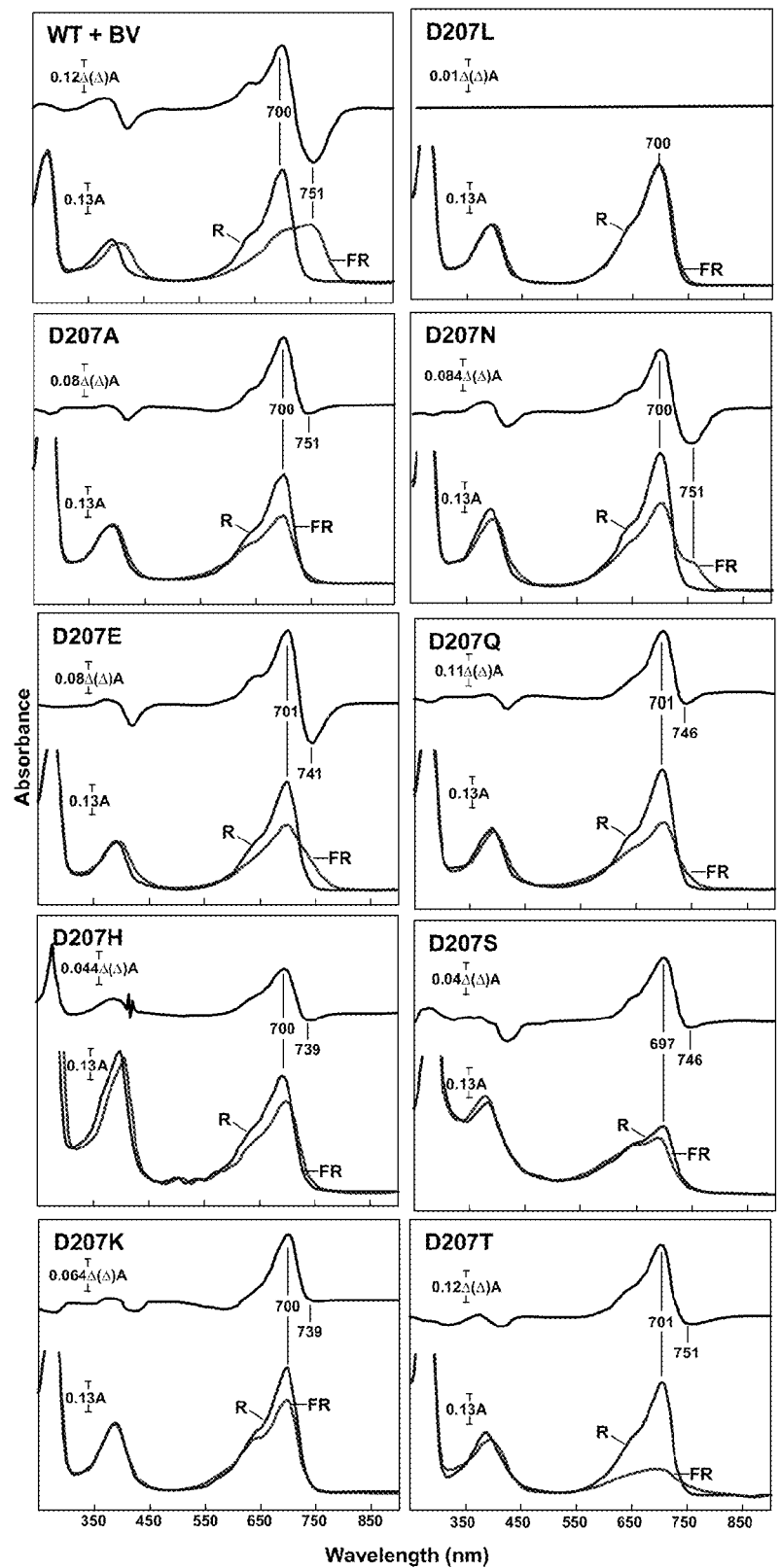
FIG. 4 shows graphs illustrating the spectral characteristics of DrBphP mutants.

While most of the Asp207 constructions expressed robustly in *E. coli*, the D207S protein expressed poorly with the majority of the protein present in the inclusion body fraction indicating that a serine at position 207 is deleterious to protein folding. Based on zinc-induced fluorescence, all the 207 mutants were able to covalently bind BV, even the insoluble D207S (Table 1, FIG. 2). Though all mutations formed Pr, even the most conserved mutations; D207E, D207N, and D207Q, fail to properly photoconvert to Pfr and arrested at an intermediate in the Phy photocycle (FIG. 4). In addition, all of the other mutants failed to properly photoconvert (FIG. 4). Several, including D207A, D207H, D207K, and D207S, also arrest at a photocycle intermediate when exposed to R (FIG. 4). D207L appears to be completely locked in Pr and shows no photoconversion after prolonged R-irradiation, while D207T appears to completely photobleach upon R-irradiation (FIG. 4).

Fluorescence Spectroscopy of Position D207.

The majority of the tested D207 mutants exhibited increased fluorescence. Indeed all mutants, except D207E and D207S, fluoresced red when the purified proteins were excited with UV light (Table 1). FIG. 4 illustrates the visual properties of the D207 mutants assembled with BV. The proteins were standardized for equal absorbance at 700 nm. The purified WT BphP and D207 substitution mutants were imaged in white light or UV light. Not wanting to be bound by the following explanation, it is possible that the energy required to drive the isomerization of the chromophore is released as fluorescence.

Figure 6:
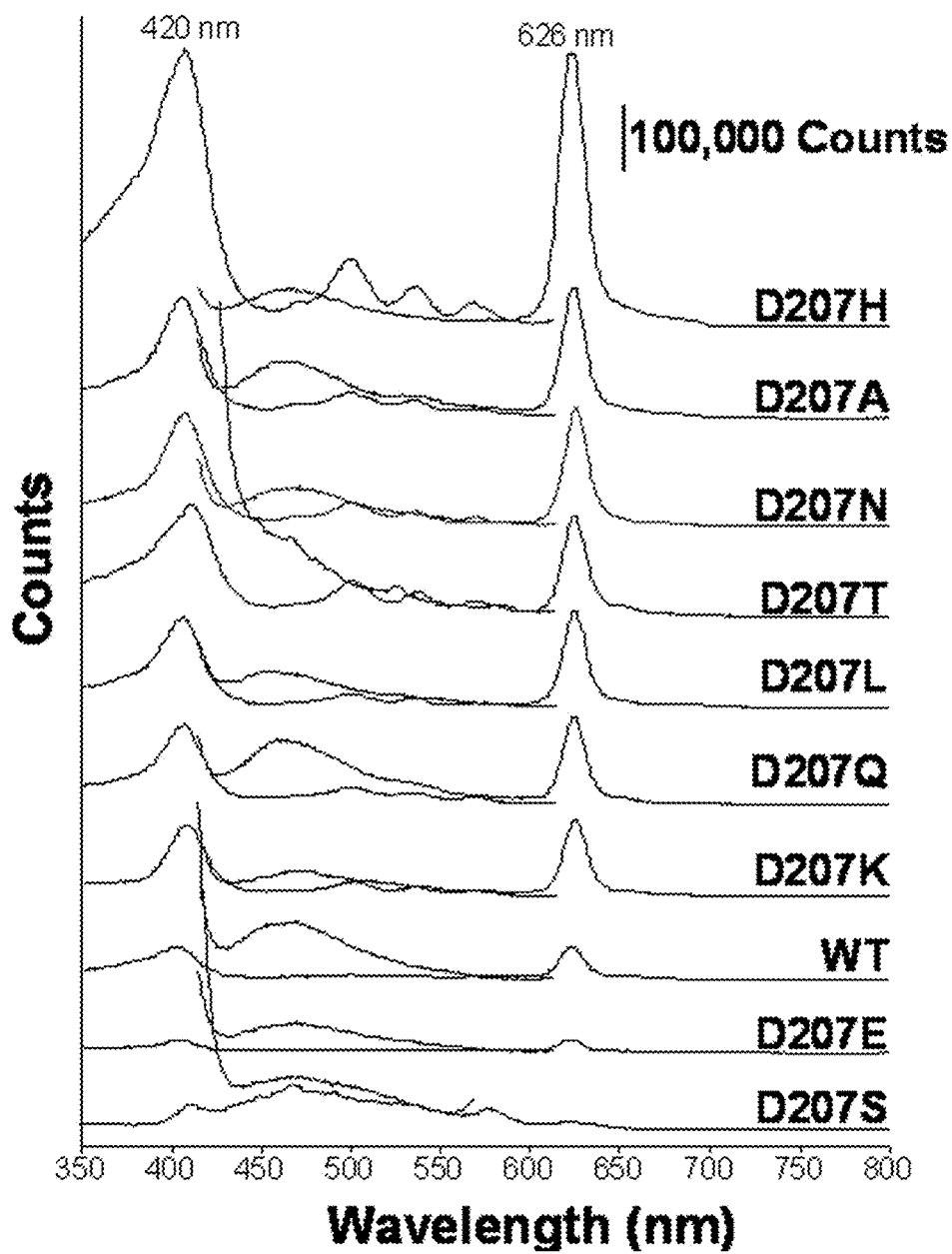
FIG. 6 is a graph showing fluorescence excitation and emission spectra of various D207 *D. radiodurans* mutants assembled with BV (biliverdin).

To better define the fluorescent properties of the mutants, they were analyzed by fluorescence spectroscopy and their excitation and emission maxima were determined. FIG. 6 illustrates the fluorescence excitation and emission spectra of D207 mutants assembled with BV. Fluorescence excitation (left peak, 410-420 nm) and emission spectra (right peak, 626 nm) of the purified WT and mutant D207 samples were measured after being standardized for equal protein (absorbance at 280 nm). Bar represents 100,000 counts.

The D207 constructions displayed similar excitation and emission spectra and maxima (FIG. 6). All samples displayed maximum emission at 626 nm when irradiated at 410-420 nm (FIG. 6). The mutant D207H exhibited the largest excitation and emission peaks with both being over twice the size as the next highest construction (FIG. 6).

The amount of fluorescence does not correlate to the apparent degree of photoconversion. For instance, the mutant D207L exhibited the least amount of photoconversion, yet it showed intermediate excitation and emission spectra. Conversely, the D207N mutation generated the most photoproduct and yet generated significant excitation and emission spectra (FIG. 6). These two mutants are similar with respect to fluorescence, yet dissimilar with respect to photoconversion.

Resonance Raman Spectroscopy of D207.

To better understand the photochemical properties of several mutants, Asp207, D207A, D207E, and D207H were investigated by Resonance Raman spectroscopy. D207A was chosen because it likely abolishes any contacts made to the chromophore at position 207 based on the 3D structure of DRCBD (Wagner et al., 2005). D207H was chosen because of its bright fluorescence in UV, and D207E was chosen because its photochromic properties were the least affected when compared to those of other D207 substitutions.

Resonance Raman spectroscopy provides information about the vibrations of atoms and is very similar to infra-red (IR) spectroscopy (Meier, 2005, *Chem. Soc. Rev.* 34: 734-752). Because Resonance Raman spectroscopy exclusively probes the vibrational bands of the bilin and not the protein, it is an ideal technique for analyzing the structure and protonation state of BV (Mroginski et al., 2004).

Figure 7:
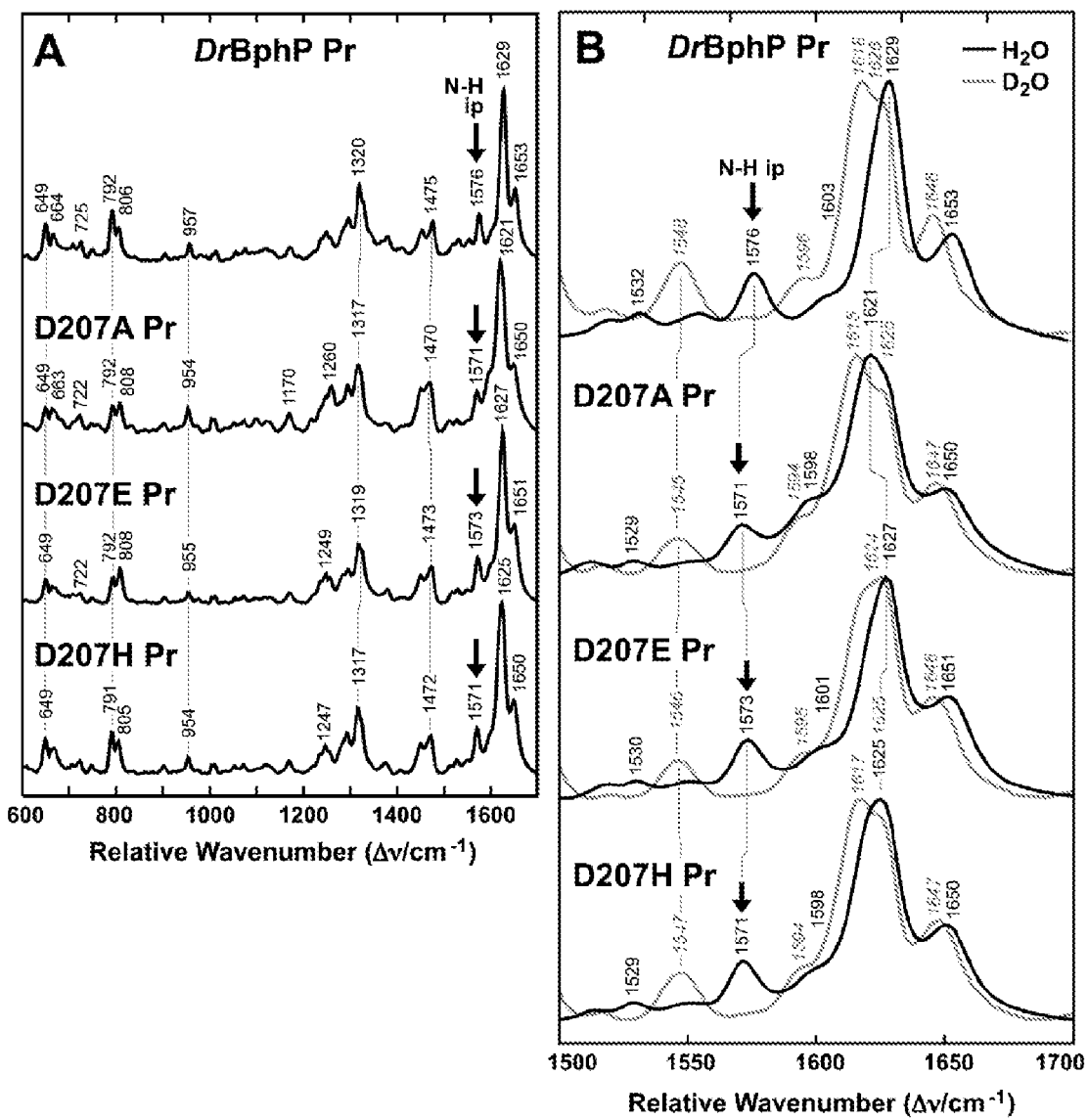
FIG. 7 shows graphs illustrating Resonance Raman analysis of Pr conformer of D207A, D207E, and D207H mutants of *D. radiodurans*.

FIG. 7 illustrates the resonance Raman analysis of Pr conformer of D207A, D207E, and D207H. FIG. 7(A): experimental Resonance Raman spectra of the Pr conformer of the various D207 substitutions in $H_2O$. FIG. 7(B): enlarged view of (A) showing the Resonance Raman spectra of the same polypeptides in both $H_2O$ and $D_2O$. The vibrational node corresponding to the N—H plane is indicated. The spectral region between 1400 and 1700 $cm^{-1}$ is particularly diagnostic for the configuration, conformation, and the protonation state of BV (Borucki et al., 2005, *J. Biol. Chem.* 280: 34358-34364) (FIGS. 7A, B). The Resonance Raman spectra of the parent Pr states of WT-DrBphP, D207A, D207E, and D207H (all in $H_2O$) are compared in FIG. 7A. Inspection of this region confirmed that the chromophore geometry of the mutants is quite similar to that of DrBphP in the Pr form (FIGS. 7A, B). Moreover, the spectra demonstrate that the chromophore is protonated since the marker band originating from the N—H in-plane bending mode of the rings B and C at 1577 $cm^{-1}$ is clearly visible in all four spectra but disappears in a $D_2O$ containing buffer (FIG. 7B).

Inspection of the high-frequency region (1400-1700 $cm^{-1}$) reveals some differences between the mutants and DrBphP beyond the level of tetrapyrrole configuration and conformation (FIGS. 7A, B). All three D207 mutants show a distinct downshift of the most prominent bands observed for DrBphP at 1577, 1631, and 1656 $cm^{-1}$ by ~5 $cm^{-1}$. The N—H in-plane bending (1577 $cm^{-1}$), which is a diagnostic band for the protonated chromophore, had a similar intensity in the D207E and D207H variants, indicating that the chromophore is protonated in each case. The downshift of this mode in both D207E and D207H suggests that the hydrogen-bond interactions around the chromophore are altered (FIG. 7B). Specifically, the downshift indicates an increase in the distances between the ring B and C nitrogens and the hydrogen bond acceptor. As a consequence, electrostatic interactions between the protein and the chromophore are modified, which are expected to have an effect on the C═C stretching frequencies as well. This is likely the origin for the downshift of the C═C stretching modes at 1631 and 1656 $cm^{-1}$ (FIGS. 7A, B). This interpretation only partly accounts for the spectral differences between D207A and the WT protein. Here the apparent frequency downshifts are even larger but a detailed analysis is complicated by the fact that the chromophore is in equilibrium between a major protonated and a minor non-protonated form. This conclusion is derived from the slightly reduced intensity of the N—H in-plane bending and the concomitant small intensity increase at ~1595 $cm^{-1}$ (FIG. 7A).

Figure 8:
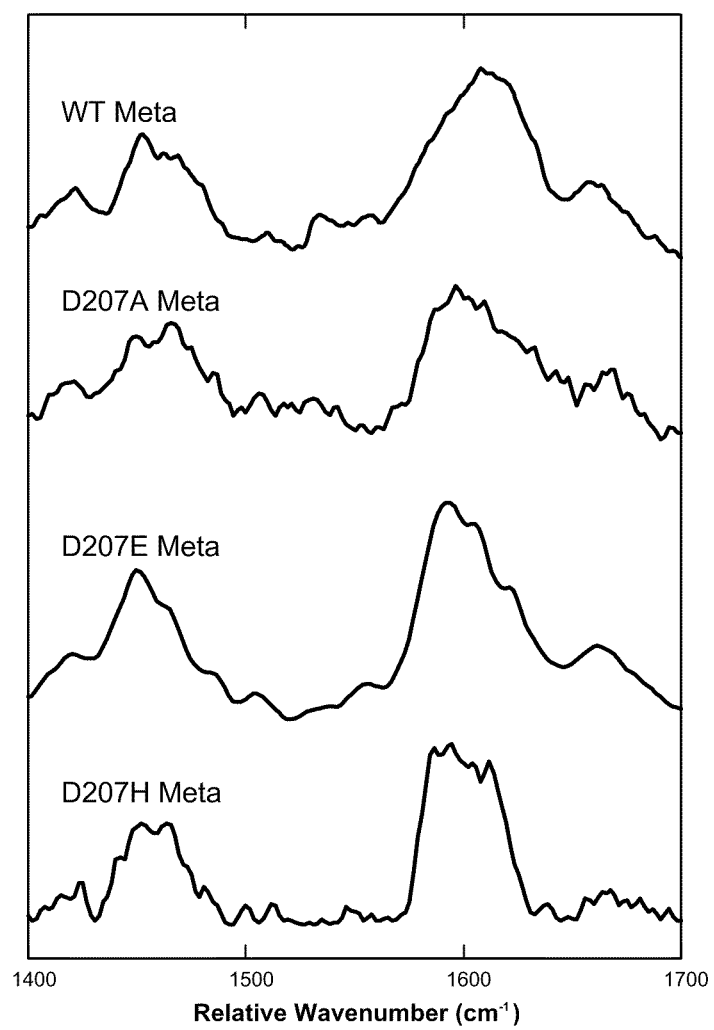
FIG. 8 is a graph illustrating Resonance Raman analysis of R-irradiated conformer of D207A, D207E, and D207H mutants of *D. radiodurans* in $H_2O$.

FIG. 8 illustrates the Resonance Raman analysis of R-irradiated conformer of D207A, D207E, and D207H in $H_2O$. R-irradiated Resonance Raman spectra were generated after subtraction of the non-photoconverted sample. The Meta spectrum was obtained by trapping R-irradiated WT-DrBphP (WT) at −30° C. When irradiated with R, the degree of photoconversion was relatively small for all D207 mutants such that the corresponding Resonance Raman spectra obtained after subtraction of the contribution of the non-photoconverted sample had a relatively poor signal-to-noise ratio. Given these restrictions, the spectra of the D207 mutants were very similar to each other. Their spectra were also similar to the spectrum of the Meta transition state of the WT protein that is trapped at −30° C. (Borucki et al., 2005), and indicate that BV is protonated after R-irradiation in all three mutations (FIG. 8). This conclusion is further supported by experiments carried out with samples in $D_2O$ ruling out a deprotonated chromophore. The analysis of D207E is particularly surprising because it too can only convert to a Meta transition state. These results suggest that during photoconversion the relative orientation of the Asp207 side chain with respect to the chromophore is altered allowing its carboxylate side chain to directly interact with the inner pyrrole rings, possibly removing a proton from one of them. This interaction may be impaired in D207E because of its slightly larger side chain. Taken together, these results show that Asp207 is essential for Pr to Pfr photoconversion in Phys.

Asp207 appears to be essential for the proper photochemical properties of DrBphP (FIGS. 3, 4, and 7). Because Asp207 and its neighboring Ile and Pro residues are conserved throughout the Phy superfamily (Karniol et al., 2005; Wagner et al., 2005), it is not surprising that even the most conserved substitutions at position 207, glutamic acid and asparagine, fail to properly photoconvert from Pr to Pfr (FIGS. 3 and 7). Glutamic acid and aspartic acid differ by only 1 carbon atom; nevertheless, a Resonance Raman spectrum for D207E is similar to D207A and D207H, indicating that all three are unable to compensate for an aspartic acid (FIG. 8).

Modification of Isoleucine 208.

Isoleucine 208 is situated in the same highly conserved DIP motif as Asp207 (Karniol et al., 2005; Wagner et al., 2005) (FIGS. 1C, D) and appears to provide hydrophobic packing contacts for the B and C rings. Only subtle differences in photochemistry were observed when this isoleucine was changed to an alanine in DrBphP. The Ile208Ala (I208A) mutant could covalently bind BV and effectively form Pr. When exposed to R, the assembled I208A chromoprotein produced a photoproduct with an absorption spectrum similar to DrBphP, but with reduced absorption (Table 1 and FIGS. 2, 3). These results suggest that though not necessary for Pfr production, Ile208 affects the photoequilibrium between Pr and Pfr and thus plays a role in optimal Pfr formation.

Modification of Tyrosine 216.

The B-ring propionic side chain of BV forms a salt bridge with the amines of Arg254 and may also form a hydrogen bond with the hydroxyl of Tyr216 (FIGS. 1C,D) (Wagner et al., 2005). To test whether Tyr216 helps to secure BV in the binding pocket, it was substituted for either a histidine (Y216H) or tryptophan (Y216W).

Both mutants covalently bound BV and produced Pr (Table 1 and FIGS. 1, 2). When irradiated with R, Y216H produced a Pfr absorption spectrum with a slightly blue-shifted maximum at 748 nm, indicating that a histidine can likely compensate for a tyrosine at position 216 (FIG. 2). Although Y216W also formed Pr, its absorption was dramatically reduced as compared to DrBphP. When exposed to R, Y216W showed little photoconversion to Pfr (FIG. 2).

While histidine at position 216 appeared to fulfill the role of a tyrosine, a tryptophan, because of its bulky side chain, may negatively alter the structure of the bilin binding pocket and therefore preclude proper photochemistry. These results suggest that Tyr216, though not necessary for chromophore attachment, does participate in Pr to Pfr photoconversion.

Modification of Arginine 254.

The amine group of Arg254 forms a salt bridge to the B-ring propionate side chain of BV (Wagner et al., 2005) (FIGS. 1C, D). To test if Arg254 plays a role in chromophore attachment and the Phy photocycle, position 254 was changed to alanine (R254A), lysine (R254K), or glutamine (R254Q). While R254A and R254K were able to assemble with BV to form Pr (Table 1 and FIGS. 2, 5), R254Q failed to covalently associate with BV (Table 1 and FIG. 2). In addition, R254Q does not make Pr, suggesting that glutamine blocks noncovalent association with BV.

It is plausible that lysine at position 254 should be able to form an electrostatic interaction with the chromophore and partially fulfill the role of Arg254. In accord, R254K can convert between Pr and Pfr with absorption maxima at 700 nm and 750 nm, respectively (Table 1 and FIG. 5) suggesting that lysine is able to perform the same photochemical processes as arginine at position 254. Similar results were seen with a corresponding mutation in SyCph1 (Hahn et al., 2006).

Figure 5:
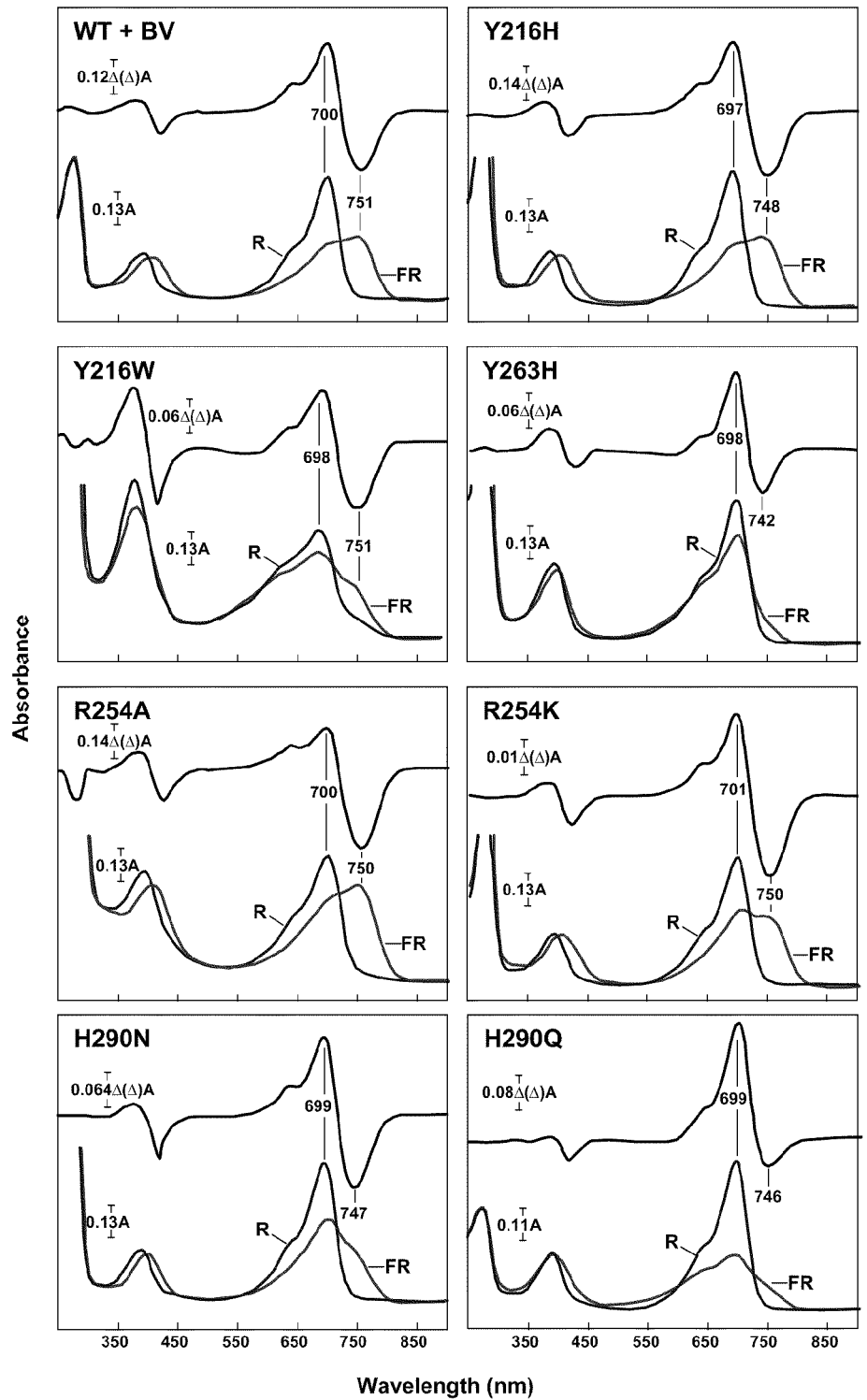
FIG. 5 shows graphs illustrating the spectral characteristics of DrBphP mutants.

An alanine substitution at position 254 would abolish the salt bridge between the protein and the propionate side chain of BV. While R254A was able to form Pr, its Pr absorbance was nearly four times weaker than that of DrBphP as judged by the ratio between absorption at 700 and 280 nm, and surprisingly, even before R irradiation, the R254A mutation exhibits residual Pfr (FIG. 5). When R-irradiated, R254A displays normal Pr to Pfr photo-conversion (FIG. 5). However, the R245A mutation displays no photoconversion even after 12 hrs of continuous darkness while DrBphP appears to revert to mixture of Pr/Pfr more substantially enriched for Pr. Collectively these results demonstrate that positively charged Arg254 helps in securing BV in the bilin pocket and may play a role in dark reversion kinetics.

Modification of Histidine 290.

In the Pr conformer of DRCBD, the Nε of His290 provides the sole electrostatic interaction to the D-ring carbonyl of BV suggesting that it may be responsible for the stability of the Pr conformer (FIGS. 1C,D) (Wagner et al., 2005). To test the importance of His290, it was substituted with asparagine (H290N) or glutamine (H290Q). Both constructions were able to bind BV and form Pr with an absorption maximum at 699 nm (Table 1 and FIGS. 2, 5).

While H290N displayed a normal Pr absorption spectrum, the absorption maximum in H290Q was larger than the Pr maximum of DrBphP when the spectra were normalized for protein concentration (FIG. 5). When exposed to R, both H290N and H290Q formed nearly indistinguishable bleached intermediates with absorption maxima at 747 and 746 nm, respectively. Like several of the other mutants that fail to photoconvert to Pfr, H290N and H290Q also fluoresced when excited with UV (Table 1). These results imply that His290 is necessary for the maintenance of Pr and for the proper formation of Pfr.

Emission Spectra from *D. radiodurans* BphP 501-D207H, *Agrobacterium tumefaciens* Agro2 N504-Wild Type, and *Agrobacterium tumefaciens* Agro2 N504-D196H Mutant.

The plasmids used in these experiments were all pET 21a (Novagen), with an N-terminal T7 tag and C-terminal 6×His tag. Growth and purification for all was as follows: growth of bacteria in 1 L LB+0.1 mg/mL Ampicillin to OD600~1, induction with 250 mg IPTG at 20° C. for four hours. Bacterial cells were harvested by centrifugation, and the cell pellets were stored −80° C.

Pellets were resuspended in 25 mL 30 mM Tris pH 8.0, 0.3 M NaCl, 5 mM imidazole, 1 mM TCEP, EDTA-free Complete Mini protease inhibitor tablet (Roche) per manufacturer's instructions. Cells were lysed by two passes through a French press, lysate was cleared by centrifugation. 200 µL of 20 mM biliverdin was added to cleared lysate under green safe lights and incubated on ice for 1 hour. All subsequent steps were performed under green safe lights. Cleared lysate was passed over a 1.5 mL NiNTA column, washed with 15 mL lysis buffer (less TCEP and protease inhibitor), and eluted in 6 mL 30 mM Tris pH 8.0, 0.3 M NaCl, 250 mM imidazole.

*D. radiodurans* CBD-D207H and 501-D207H proteins were further purified as follows: First, 0.6 mL 3.5 M ammonium sulfate was added to 6 mL of protein sample, which was then run over an 8 mL Phenyl-sepharose column and eluted in a gradient from 30 mM Tris pH 8.0, 0.3 M AmSO$_4$ to 30 mM Tris pH 8.0. Pure protein fractions having the highest 700/280 ratio (save Agro2 N504 Wild-type where the 750/280 ratio was used) were pooled and dialyzed versus 2 L 30 mM Tris pH 8.0, 50 mM NaCl.

Fluorescence measurements were recorded on a Jobin Yvon Horiba Fluoromax-3 fluorimeter at 20° C. in a 2.5 mL sample. Measurements were taken on protein that had been kept under safe lights save for the time it took to put the sample into the fluorimeter.

Table 2 shows a summary of major excitation and emission wavelengths, and the relative amount of fluorescence (i.e., emission count) for the tested *Deinococcus radiodurans* mutant BphP 501-D207H, *Deinococcus radiodurans* mutant CBD-D207H, *Agrobacterium tumefaciens* mutant Agro2N504-D196H (i.e., BphP2), and *Agrobacterium tumefaciens* Agro2 N504-Wild type (Karniol and Vierstra, 2003, *Proc. Natl. Acad. Sci. USA* 100: 2807-2812; Karniol et al., 2005). The Agro2 BphP2 protein sequence can be found in the GenBank under accession number Q8UDG1. The importance of Agro2 is that it is Pfr in the ground state instead of the normal Pr, unlike other phytochromes described herein.

Figure 9:
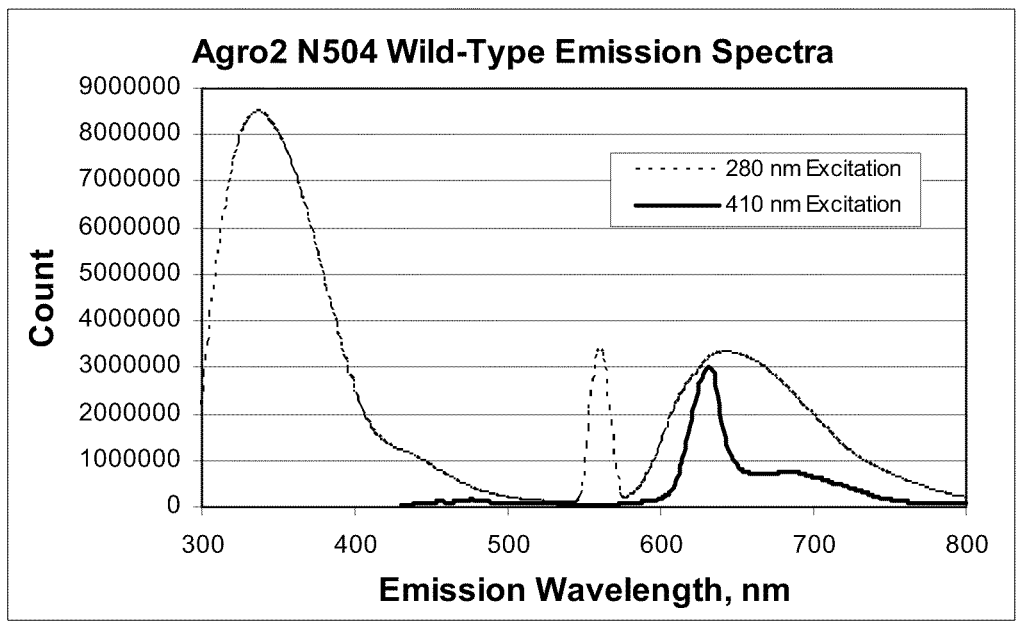
FIG. 9 shows the emission spectra from Agro2 N504-Wild type.
Figure 10:
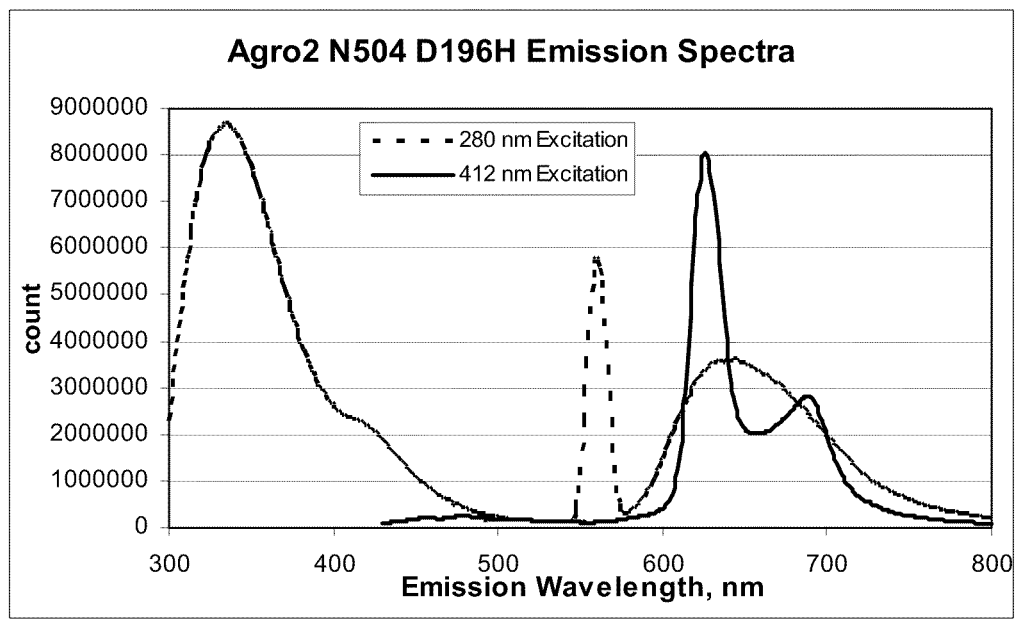
FIG. 10 shows the emission spectra from the Agro2 mutant N504-D196H.
Figure 11:
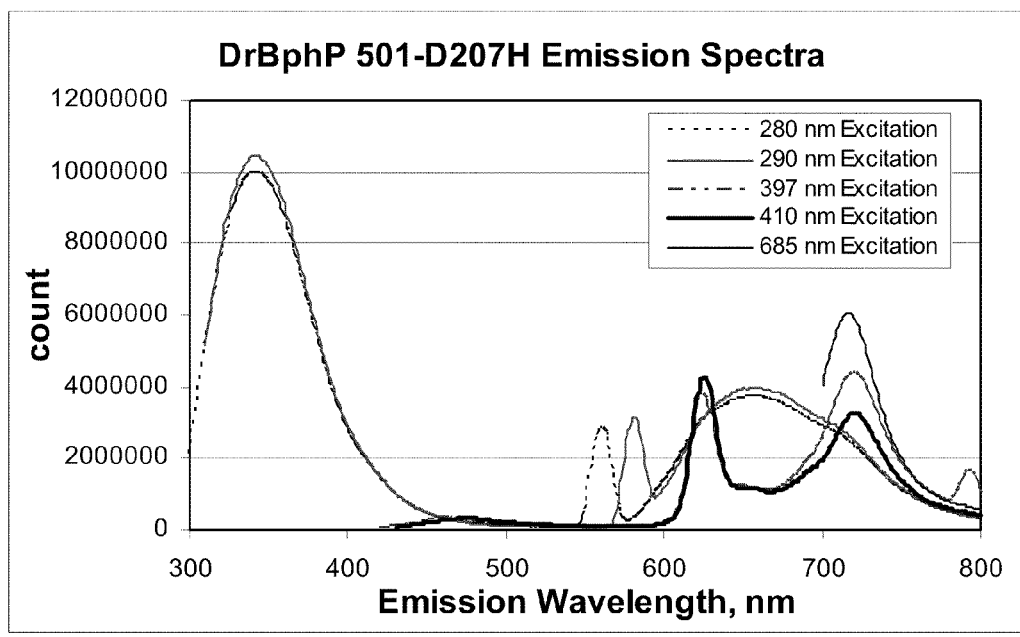
FIG. 11 shows the emission spectra from the *D. radiodurans* mutant BphP 501-D207H.
Figure 12:
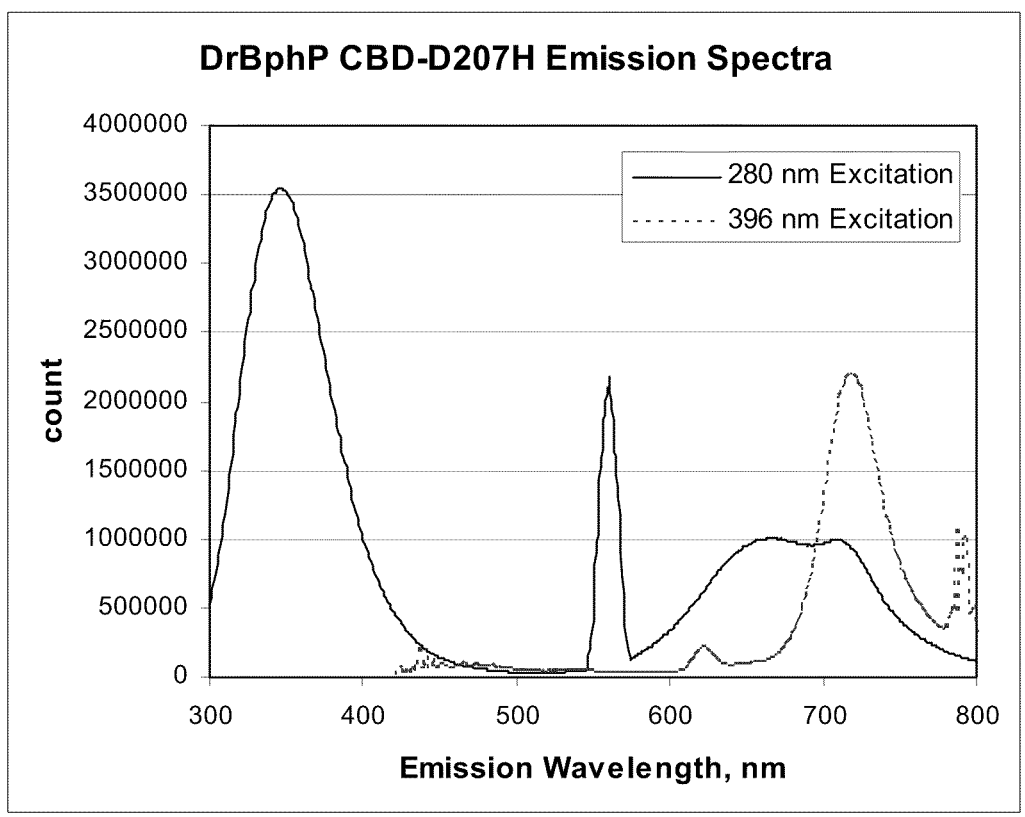
FIG. 12 shows the emission spectra from the *D. radiodurans* mutant CBD-D207H.

FIG. 9 shows the emission spectra from Agro2 N504-Wild type. FIG. 10 shows the emission spectra from Agro2 N504-D196H. FIG. 11 shows the emission spectra from *D. radiodurans* BphP 501-D207H. FIG. 12 shows the emission spectra from the *D. radiodurans* mutant CBD-D207H.

FIGS. 9-12 all have spurious peaks at twice the excitation wavelength; for example excitation at 280 nm produces an apparent 560 nm peak in the emission spectrum. These peaks are due to the equipment, and are not included in Table 2.

The *D. radiodurans* DrBphP 501-D207H mutant had an A280 absorbance of 0.516, an A700 absorbance of 0.422, and 700/280 ratio of 0.818, in sample buffer consisting of 30 mM Tris pH 8.0, 50 mM NaCl. The *D. radiodurans* CBD-D207H mutant (N321-D207H) had an A280 absorbance of 0.1452, an A700 absorbance of 0.2952, and 700/280 ratio of 2.03, in the same sample buffer as above.

The Agro2 N504-wt absorbance values had an A280 absorbance of 1.806, an A750 absorbance of 1.49, and 750/280 ratio of 0.825, in sample buffer consisting of 30 mM Tris pH 8.0, 50 mM NaCl, 30 mM imidazole. The Agro2 N504-

D196H mutant had an A280 absorbance of 2.094, an A700 absorbance of 0.358, and 700/280 ratio of 0.171, in the same sample buffer as above.

The increase in fluorescence intensity for Agro2 N504-D196H/WT, after normalizing concentration by comparing absorbance at 280 nm and comparing similar peaks from the same excitation wavelength, was as follows: with excitation at 280 nm, the 334(D196H)/336(WT) emission was 0.88; the 644/640 emission was 0.94; with excitation at 412 nm, the 626/632 emission was 2.29, and the 688/685 emission was 3.17. D196H was slightly less fluorescent than the wild-type when excited at 280 nm, but significantly brighter when excited at 412 nm.

TABLE 2

Summary of major excitation and emission wavelengths

| Excitation wavelength (nm) | Emission wavelength (nm) | Emission count |
|---|---|---|
| D. radiodurans BphP 501-D207H | | |
| 280 | 342 | 9992890 |
|  | 658 | 3743920 |
| 290 | 341 | 10457760 |
|  | 656 | 3984970 |
| 397 | 459 | 363760 |
|  | 624 | 3782050 |
|  | 653 | 1217540 |
|  | 721 | 4384670 |
| 410 | 475 | 377280 |
|  | 625 | 4274320 |
|  | 720 | 3270040 |
| 685 | 716 | 6078400 |
| Agro2 N504-D196H | | |
| 280 | 334 | 8683000 |
|  | 644 | 3621800 |
| 412 | 626 | 8047720 |
|  | 688 | 2830940 |
| Agro2 N504 Wild-type | | |
| 280 | 336 | 8492880 |
|  | 640 | 3326820 |
| 410 | 632 | 3027550 |
|  | 685 | 769850 |
| D. radiodurans BphP CBD-D207H | | |
| 280 | 347 | 3542757 |
|  | 668 | 1008171 |
|  | 710 | 998235 |
| 396 | 622 | 211085 |
|  | 718 | 2197514 |

Example 2

Phytochrome-Based Fluorophores from *Synechococcus*

Operon Organization and Sequence Alignment.

Genomic sequences for the SyA-Cph1 and SyB-Cph1 operons from *Synechococcus* sp. OS-A (also referred to as sp. JA-3-3Ab: NCBI Accession NC_007775) and *Synechococcus* sp. OS-B' (also referred to as sp. JA-2-3B'a(2-13): NCBI Accession NC_007776) were obtained from The Institute for Genomic Research (TIGR; Rockville, Md.) Comprehensive Microbial Resource (CMR) website. Operon organizations were predicted by the FGENESB bacterial and operon gene prediction (Softberry, Inc., Mount Kisco, N.Y.) and TIGR CMR operon prediction functions. Related proteins were identified by BLAST searches of the GenBank™ database, aligned by CLUSTAL W (Higgins et al., 1994, *Nucleic Acids Research* 22: 4673-4680), and displayed using MACBOX-SHADE version 2.15 (Institute of Animal Health, Pirbright, UK).

Construction of Recombinant Phy Expression Strains.

PCR-based modifications of Phys involved paired amplifications that were subsequently combined, melted, and re-annealed to generate blunt-ended doubled-stranded fragments as described by Ulijasz et al., 1996, *J. Bacteriol.* 178: 6305-6309. The DNA templates for SyA-Cph1 and SyB-Cph1 full-length coding sequences were PCR amplified directly from *Synechococcus* sp. OS-A and OS-B' DNA, respectively. The pBAD-C expression plasmid encoding the PAS-GAF-PHY domains from *Synechocystis* sp. PCC6803 (Syn) Cph1 (residues 1-514) was as described by Gambetta and Lagarias, 2001, *Proc. Natl. Acad. Sci. USA* 98: 10566-10571. The codons for the C-terminal c-Myc tag attached to Syn-Cph1 (PAS-GAF-PHY) were replaced with those encoding a 6His tag (underlined) followed by a stop codon by ligating the annealed primers 5'-AGCTTTGCATCATCAT-CATCATCATTGAAGC-3' (SEQ ID NO:39) and 5'-AGCT-GCTTCAATGATGATGATGATGCAA-3' (SEQ ID NO:40) into HindIII-digested pBAD-C plasmid containing the Syn-Cph1 (PAS-GAF-PHY) construction. From this manipulation, the plasmid pBAD-6H was generated.

Assemblies of the various Cph truncations and mutants were accomplished by PCR using appropriate primer pairs, the sequences of which can be found in the accompanying sequence listing. Products for the two PCR reactions were combined, melted and re-annealed, phosphorylated, and purified as described by Ulijasz et al., 1996, *J. Bacteriol.* 178: 6305-6309. Phosphorylated flush inserts were then ligated into the NcoI- and HindIII-digested pBAD-6H plasmid. Site-directed mutations were introduced into the 6His-tagged SyB-Cph1 (GAF) construction by the QuickChange method (Stratagene, La Jolla, Calif.) using Pfx polymerase (Invitrogen, Carlsbad, Calif.) in combination with the appropriate mutagenic primers (see sequence listing). All coding regions were sequenced in their entirety to confirm the presence of the desired mutation and the absence of secondary mutations.

The PAS-GAF-PHY truncation (residues 1-501) of the bacterio-Phy from *D. radiodurans* (DrBphP) was generated by PCR amplification of the full-length coding region with the primers 5'-CGTAAGGATCCATGAGCCGGGAC-CCGTTGCCC-3' (SEQ ID NO:41) and 5'-CCTGACTC-GAGCGCCCCGGTCAATGTGTCACG-3' (SEQ ID NO:42) that were designed to add BamHI and XhoI sites to the 5' and 3' ends, respectively. The PCR product was digested with BamHI and XhoI and ligated into the pET21a plasmid (Novagen, Madison, Wis.) that was similarly digested.

Protein Expression and Purification.

PCB-containing holo-Cphs suitable for absorption, resonance Raman (RR), and/or NMR spectroscopy were produced using the dual-plasmid *Escherichia coli* expression system developed by Gambetta and Lagarias, 2001, *Proc. Natl. Acad. Sci. USA* 98: 10566-10571. The kanamycin-resistance plasmid pPL-PCB expressed the HO and BVR enzymes under β-D isopropyl thiogalactopyranoside (IPTG) control to direct the synthesis of PCB from heme. Ampicillin-resistance pBAD-6H plasmids expressed the 6His-tagged SyA-Cph1, SyB-Cph1 and Syn-Cph1 truncations solely under arabinose control (Gambetta and Lagarias, 2001, *Proc. Natl. Acad. Sci. USA* 98: 10566-10571). The pPL-PCB and pBAD-6H plasmids were simultaneously introduced into the ara operon-deficient *E. coli* expression strain BL21-AI (Invitrogen, Carlsbad, Calif.) and cultured in 500 mL of repression medium (RM) to suppress protein production. After an overnight incubation, the cells were harvested, resuspended, and grown at 37° C. in 2 L of M9 minimal medium containing $NH_4Cl$, 0.2% glycerol, 100 µM α-aminolevulinic acid (ALA) (Wang et al., 1999, *J. Bacteriol.* 181: 1211-1219), 100 µM $FeCl_3$, 5 mg of thiamine, and a vitamin mix (Venters et al., 1991, *Biochemistry* 30: 4491-4494). To synthesize isotopically-labeled SyB-Cph1 (GAF), $NH_4Cl$ and glycerol were replaced with $^{15}N$- and $^{13}C$-isotopically labeled forms, respectively. To produce SyB-Cph1 (GAF) that contained either [$^{15}N$]-PCB or [$^{13}C$]-PCB (isotopically-labeled at all six methyl groups and the $CH_2$ carbon located on each propionate side chain (FIG. 20A) attached to unlabeled protein, unlabeled ALA in the medium was replaced with 100 µM [$^{15}N$]-ALA (Medical Isotopes Inc., Pelham, N.H.) or 1,2-[$^{13}C$]-ALA (a gift from Dr. Mario Rivera, Kansas State University), respectively. In all cases, once the $OD_{600}$ of the culture reached 0.8-0.9, PCB synthesis was induced by adding 1 mM IPTG. After 2 hrs, synthesis of the Cph1 apo-proteins was induced by the addition of 0.2% w/v arabinose and the cultures were grown overnight at 20° C. All subsequent steps were performed under green safelights.

To purify the various Phy chromoproteins, the expressing cells were collected by centrifugation, resuspended in 25 ml/L of culture in lysis buffer, consisting of 50 mM Tris-HCl (pH 8.0), 100 mM NaCl, 1 mM dithiothreitol, 1 mM phenylmethylsulfonyl fluoride, and a tablet of Complete-EDTA free protease inhibitor cocktail (Hoffmann-La Roche, Basel, Switzerland), and lysed by sonication. NP-40 (0.1% v/v) was then added to the lysates followed by incubation on ice for 30 min, agitation at 4° C. for 2 hrs, and finally clarified by centrifugation at 16,000×g for 30 min. The resulting supernatant was filtered through a 0.45 µM filter (Corning, Corning, N.Y.) and dialyzed into extraction/wash buffer (50 mM Tris-HCl (pH 7.0), 300 mM NaCl, 10% (v/v) glycerol, 20 mM imidazole, 0.05% (v/v) Tween-20, and 1 mM 2-mercaptoethanol) overnight at 4° C. as described by Gambetta and Lagarias, 2001, *Proc. Natl. Acad. Sci. USA* 98: 10566-10571. The Phy chromoproteins were then purified by nickel chelate-affinity chromatography (Qiagen Sciences, Germantown, Md.) using the extraction/wash buffer plus 300 mM imidazole for elution. The Phy-containing eluates were subjected to hydrophobic interaction FPLC using a 1×10 cm phenyl HP column (Pharmacia, Uppsala, Sweden) with a 0 to 300 mM ammonium sulfate gradient in 25 mM Tris-HCl (pH 8.0) for elution. Pooled Phy-containing fractions for NMR analysis were exchanged and concentrated into 10 mM deuterated Tris-HCl (pH 8.5) (Sigma, St. Louis, Mo.) in 100% $H_2O$ using an Amicon Ultra-15 filter (Millipore, Billerica, Mass.). [$^{13}C$]-PCB containing samples were exchanged into 10 mM Tris-DCl (pH 8.5) in 100% $D_2O$. This buffer was found to enhance the stability of SyB-Cph1 (GAF) chromoprotein based on the solubility screen of Collins et al., 2004, *Acta. Crystallogr. D. Biol. Crystallogr.* 60: 1674-1678. For all non-isotopically labeled Cph1 holo-proteins, the same protocol was applied except non-isotopically labeled reagents were used in the M9 media preparation and the FPLC purification step was omitted.

To test for bilin specificity, the various Phy apo-proteins were expressed in the pBAD-6H plasmid as above without co-expression of the HO and BVR genes from pL-PCB. Apo-DrBphP(PAS-GAF-PHY) C-terminally tagged with a 6His sequence was expressed as described by Karniol et al., 2005, *Biochem. J.* 392: 103-116. The *E. coli* cells were resuspended in 30 mM Tris-HCl (pH 8.0), 100 mM NaCl and 30 mM imidazole, and lysed by sonication. The resulting extracts were clarified by centrifugation as above and then mixed with 100 µM of either PCB or BV for 2 hrs at 4° C. The polypeptides were then purified by nickel-chelate affinity chromatography using 300 mM imidazole for elution. Presence of the covalently bound bilin was assayed by zinc-induced fluorescence of the chromoproteins following SDS-PAGE (Bhoo et al., 2001, *Nature* 414: 776-779). PCB was purified from lyophilized *Spirulina platensis* as described (Scheer, 1984, In: *Techniques in Photomorphogenesis*, Smith et al., ed., pp. 227-256, Academic Press, New York) but without the final HPLC step. Purified BV was obtained from Frontier Scientific (Logan, Utah).

Size Exclusion Chromatography.

Size exclusion chromatography (SEC) was performed by FPLC using a 24 ml Superose 6 (S6) column (GE Healthcare, Pittsburgh, Pa.). The chromoproteins (100 µl of a 5 mg/ml sample) were first purified through the phenyl HP step, dissolved in 30 mM Tris-HCl (pH 8.0) and 200 mM NaCl, and either loaded onto the column as Pr or immediately following saturating irradiation of the sample with red light (630 nm). Absorption spectra were recorded before and after SEC to verify that the chromoproteins remained enriched in the desired states (Pr or Pfr).

Absorption and Fluorescence Spectroscopy.

Absorption spectra were measured with a PerkinElmer Lambda 650 UVN is Spectrometer (PerkinElmer, Waltham, Mass.) with the samples dissolved in 30 mM Tris-HCl (pH 8.0). Photoconversions between Pr and Pfr by red and far-red light were achieved with white light filtered through appropriate interference filters (Andover Corp. Salem, N.H.); 630-nm and 690-nm filters, respectively, for SyA-Cph1 and SyB-Cph1, and 690-nm and 730-nm filters, respectively, for Syn-Cph1. Thermostability was measured in the dark for Pr samples (absorbance of the Pr absorption maximum was adjusted to 1.5) dissolved in 30 mM Tris-HCl (pH 8.0). After heating for 20 minutes at the appropriate temperature, the samples were clarified by centrifugation at 16,000×g and the amounts of soluble chromoproteins remaining were measured spectrophotometrically. Rates of Pr→Pfr photoconversion and Pfr→Pr dark reversion were measured spectrophotometrically using the absorbance of the samples at 704 nm to determine the amount of Pfr generated or lost, respectively.

Fluorescence excitation and emission spectra were recorded with a QuantaMaster Model C-60/2000 spectrofluorimeter (Photon Technologies International, Birmingham, N.J.). Chromoprotein concentrations were adjusted to have an absorbance of 0.6 for the Pr absorbance maximum. Emission spectra were recorded during an excitation at 360 nm. Excitation spectra were recorded by measuring emission at the peak wavelength (646 nm to 664 nm depending on the sample).

Resonance Raman (RR) Spectroscopy.

RR spectra were recorded with 1064-nm excitation (Nd-YAG cw laser, line width <1 $cm^{-1}$) using Digilab BioRad (Varian, Darmstadt, Germany) or a RFS100/S (Bruker Optics, Ettlinger, Germany) Fourier-transform Raman spectrometers (4 $cm^{-1}$ spectral resolution). The near-infrared excitation line was sufficiently close to the first electronic transition to generate a strong pre-resonance enhancement of the chromophoric vibrational bands such that Raman bands of the protein matrix remained very weak in the spectra of the parent states. All spectra were measured at −140° C. using a liquid-nitrogen cooled cryostat (Linkam, Waterfield, Surrey, UK). The laser power at the sample was set at ~700 mW, which did not damage the chromoproteins as checked by comparing the absorption spectra of the samples obtained before and after RR data acquisition. The total accumulation time was less than 2 hrs for each spectrum. For all RR spectra shown herein, the background was subtracted.

The photoproducts were accumulated by irradiating the samples for a few minutes at room temperature. These raw RR spectra for Pfr included substantial contributions from residual Pr, which was subtracted using the characteristic RR bands of Pr as a reference. Further RR experimental details have been described previously (Wagner et al., 2008, *J. Biol. Chem.* 283: 12212-12226; Kneip et al., 1999, *Biochemistry* 38: 15185-15192).

NMR Spectroscopy.

Isotopically-labeled forms of SyB-Cph1(GAF) assembled with PCB (~2 mM) were dissolved in 93% $H_2O$, 7% $D_2O$, 10 mM deuterated Tris-HCl (pH 8.5), and 0.15 mM $NaN_3$ and placed in a 280 µl Shigemi microcell. Prior to NMR analysis, the tube was heated to 65° C. for 10 min to inactivate contaminating thermo-sensitive *E. coli* proteases that slowly compromised the sample. NMR spectra were collected at 25° C. using an 800 MHz $^1H$ frequency Varian INOVA spectrometer (Varian Inc., Palo Alto, Calif.) equipped with a cryogenic probe. Samples with a high proportion of Pfr were obtained by irradiating the microcell solution with saturating red light (630 nm); this photoequilibrium was maintained throughout NMR data acquisition by continuous irradiation of the microcell with a low fluence rate of red light provided by a 100-mW, 620-nm light-emitting diode (LED) (LiteON LED, Mouser Electronics, Mansfield, Tex.) channeled into the glass plunger by a fiber optic cable. Photoconversion of Pfr back to Pr was completed by irradiating the microcell with saturating far-red light (690 nm).

$^1H$-$^{15}N$ heteronuclear single quantum coherence (HSQC) spectra with $^{15}N$-$^{13}C$-labeled SyB-Cph1 (GAF) chromoprotein or unlabeled SyB-Cph1(GAF) protein assembled with [$^{15}N$]-PCB were collected as 128*(t1, $^{15}N$)×1022*(t2, $^1H$) data matrices. Acquisition times were 48 ms and 85 ms in the t1 and t2 dimensions, respectively. $^1H$-$^{13}C$ HSQC spectra that centered on the methyl region of unlabeled SyB-Cph1 (GAF) protein assembled with [$^{13}C$]-PCB were collected as 32*(t1, $^{13}C$)×769* (t2, $^1H$) data matrices. Acquisition times were 10 ms and 80 ms in the t1 and t2 dimensions, respectively. Data were processed and plotted using the NMRPipe software package (Delaglio et al., 1995, *J. Biomol. NMR* 6: 277-293). All NMR data were collected at the NIH-sponsored NMR Facility at the University of Wisconsin-Madison (NMR-FAM).

SyA-Cph1 and SyB-Cph1 Identify a New Subfamily of Phys.

A set of phytochromes with novel structures and/or photochemical properties has been discovered. The novel DNA sequences originated from two newly discovered cyanobacterial species designated *Synechococcus* sp. Octopus Spring (OS)-A and *Synechococcus* sp. Octopus Spring (OS)-B', (The Institute for Genomic Research—TIGR; Rockville, Md.). Apparent Phy homologs in these species included those closely related to Phys as well as possible orthologs of *Synechocystis* (abbreviated as Syn) Cph2 (Wu and Lagarias, 2000, *Biochemistry* 39: 13487-13495; Park et al., 2000, *Biochemistry* 39: 10840-10847), suggesting that these cyanobacteria employ an array of bilin-containing photoreceptors for their complex light behaviors.

Figure 14A:
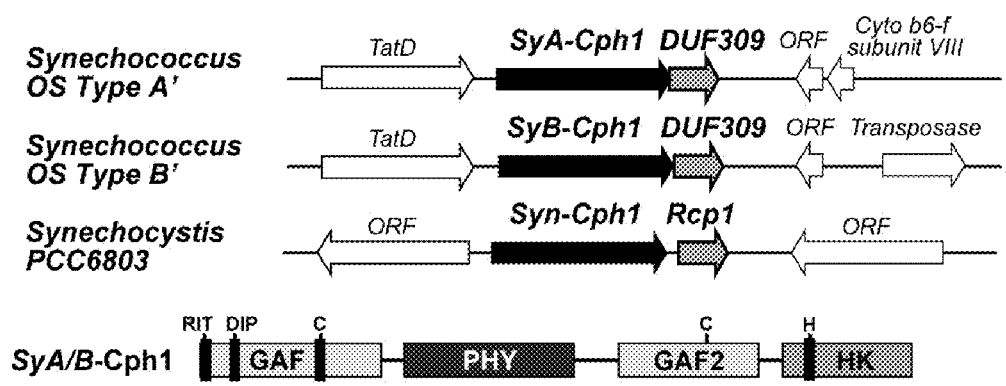
FIG. 14 shows the organization of the SyA-Cph1 (*Synechococcus* OS A phytochrome) and SyB-Cph1 (*Synechococcus* OS B' phytochrome) operons and proteins: A, Diagrams of the operons and domain architectures of the encoded proteins; B, Alignment of GAF-PHY modules in SyA-Cph1 and SyB-Cph1 with representatives from the Phy superfamily.
Figure 14B:
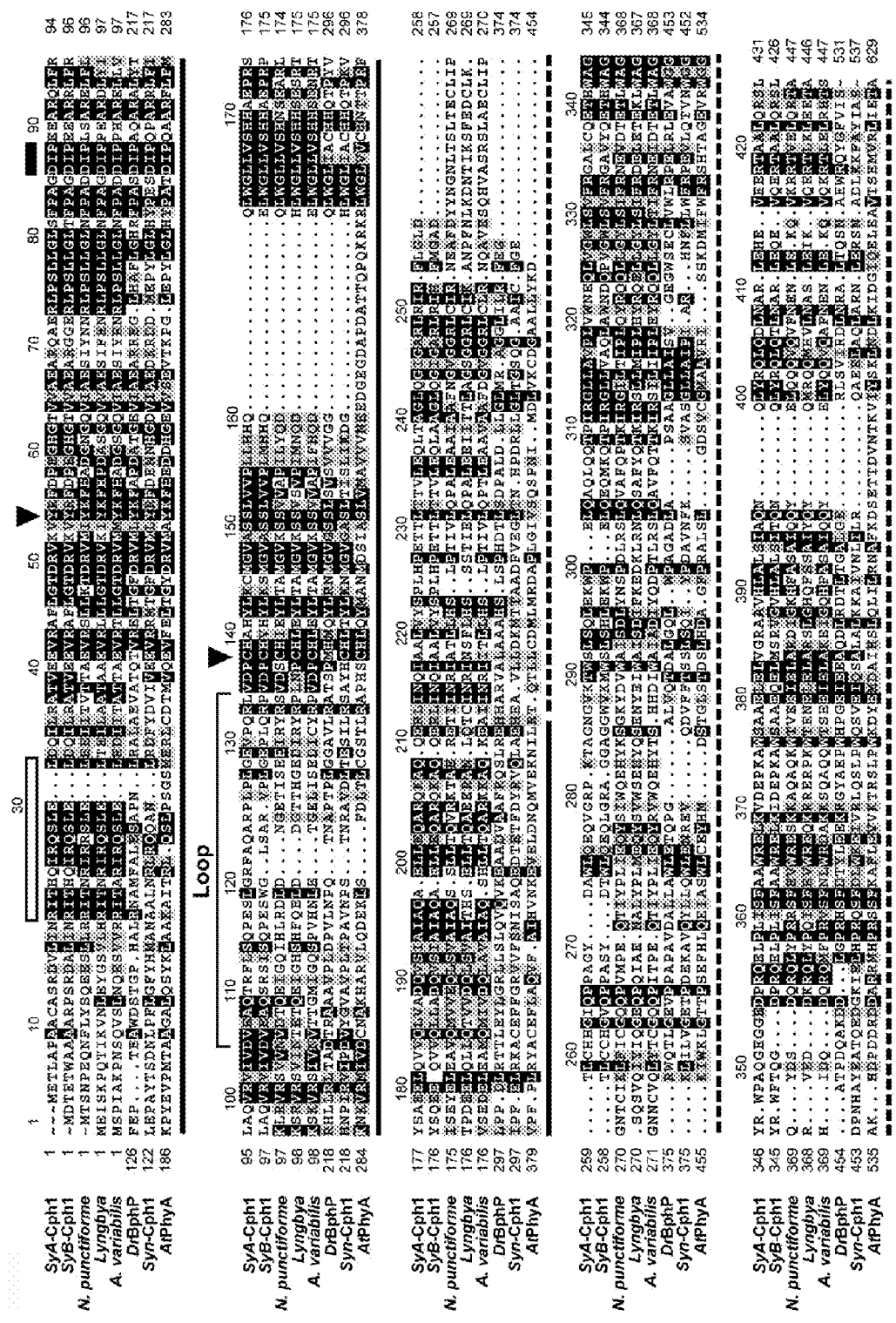

Two Phy genes, designated here as SyA-Cph1 (TIGR locus number CYA 2779) and SyB-Cph1 (TIGR locus number CYB 2465), are particularly notable for encoding proteins with GAF and PHY domain arrangements near their N-termini. The organization of the SyA-Cph1 and SyB-Cph1 operons and domain architectures of the encoded proteins is shown in FIG. 14. The Syn-Cph1 operon from *Synechocystis* PCC6803 is included for comparison. Cph1 coding regions are shown in black boxes. Other coding regions within the operons and nearby separate genes are shown in grey and white boxes, respectively. Positions of the conserved RIT and DIP motifs, the GAF cysteine (C) that binds PCB, the conserved cysteine in GAF2, and the conserved histidine (H) that is the likely phospho-acceptor site in the HK domain are indicated. Shown in FIG. 14B is an alignment of GAF-PHY modules in SyA-Cph1 and SyB-Cph1 with representatives from the Phy superfamily. Identical and similar amino acids are shown in black and gray boxes, respectively. Dots denote gaps. The RIT and DIP motifs are indicated by open and black rectangles, respectively, and the PCB-binding cysteine by the arrowhead. Asterisks identify conserved amino acids shown to be photochemically important in other Phys (Hahn et al., 2006, *FEBS J.* 273: 1415-1429; Fischer and Lagarias, 2004, *Proc. Natl. Acad. Sci. USA* 101: 17334-17339; von Stetten et al., 2007, *J. Biol. Chem.* 282: 2116-2123). The GAF lasso loop sequence that forms part of the figure-of-eight knot in DrBphP is defined by the bracket. The GAF and PHY domains are shown by the solid and dashed lines, respectively. Sequences in the alignment include those from SyA-Cph1 (YP-476144), SyB-Cph1 (YP-478662), related Cphs from *Nostoc punctiforme* PCC73102 (ZP_00111485), *Lyngbya* sp. PCC8106 (ZP_01618934), *Acaryochloris marina* (ABW26890) and *Anabaena variabilis* (YP_324761), *Deinococcus radiodurans* DrBphP (INP_285374), *Synechocystis* sp. PCC6803 Cph1 (NP_442237), and *Arabidopsis thaliana* PhyA (AAC33219). The amino acid numbering is based on the SyB-Cph1 sequence. Each of the GAF domains includes: (i) the positionally conserved cysteine (Cys-138 in both) used by Cphs to covalently bind PCB; (ii) the conserved aspartic acid (Asp-86 in SyB-Cph1) within the invariant DIP motif that helps coordinate the pyrrole water associated with the bilin; and (iii) a set of conserved/similar residues within the GAF domain that have been shown to be important for bilin ligation (for example, Arg-133, His-139 and His-169 in SyB-Cph1) and Pr→Pfr phototransformation (for example, Tyr-54, Asp-86, Phe-82, Phe-95, Tyr-142, and His-169 in SyB-Cph1) in other Phys, strongly suggesting that these Cphs assemble with linear bilins and become red/far-red photochromic.

A novel structural feature that is most likely common to the CBD of canonical Phys is a figure-of-eight knot that helps tether the PAS and GAF domains. The ~33 amino-acid loop sequence that forms the knot lasso is present within the GAF domains of both SyA-Cph1 and SyB-Cph1 (FIG. 14B). Likewise, amino acid sequence alignments revealed strong conservation within the PHY domains of both (FIG. 14B), suggesting that this domain also contributes to the formation and stability of Pfr. HK domains are also present at their C-termini. Included within the HK sequence are recognizable H, N, D/F and G boxes present in typical HKs, with the H Box containing the positionally conserved histidine (His-608) expected to participate in phosphotransfer. The GAF domains contain CH motifs. The cysteine in the first GAF domain is expected to bind PCB via a thioether linkage. It is not yet clear if the cysteine in the second GAF domain (GAF2) can also bind bilins.

Figure 22:
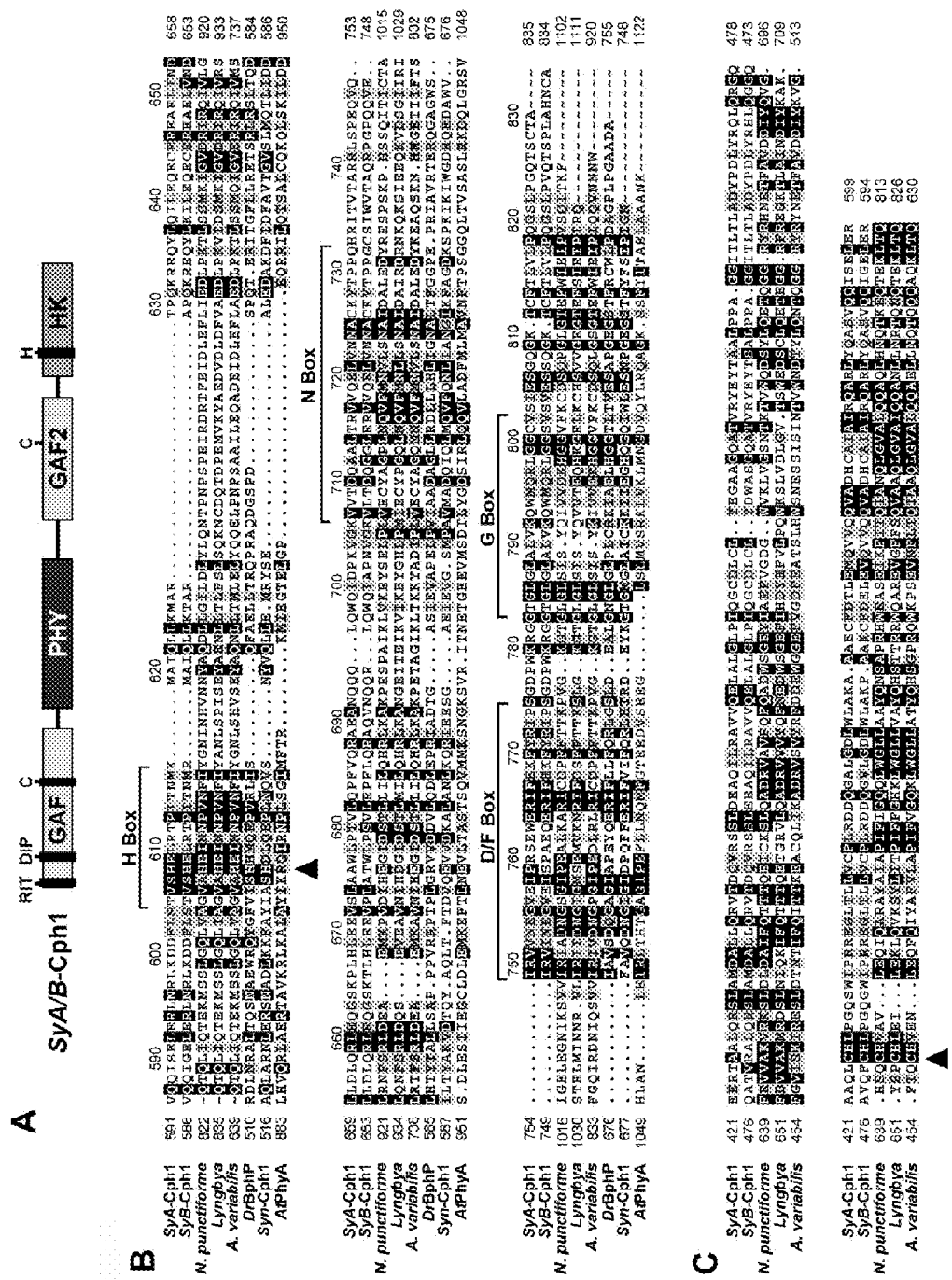
FIG. 22 is a sequence alignment of the HK and GAF2 domains in SyA-Cph1 and SyB-Cph1 with representatives from the Phy superfamily.
Figure 23:
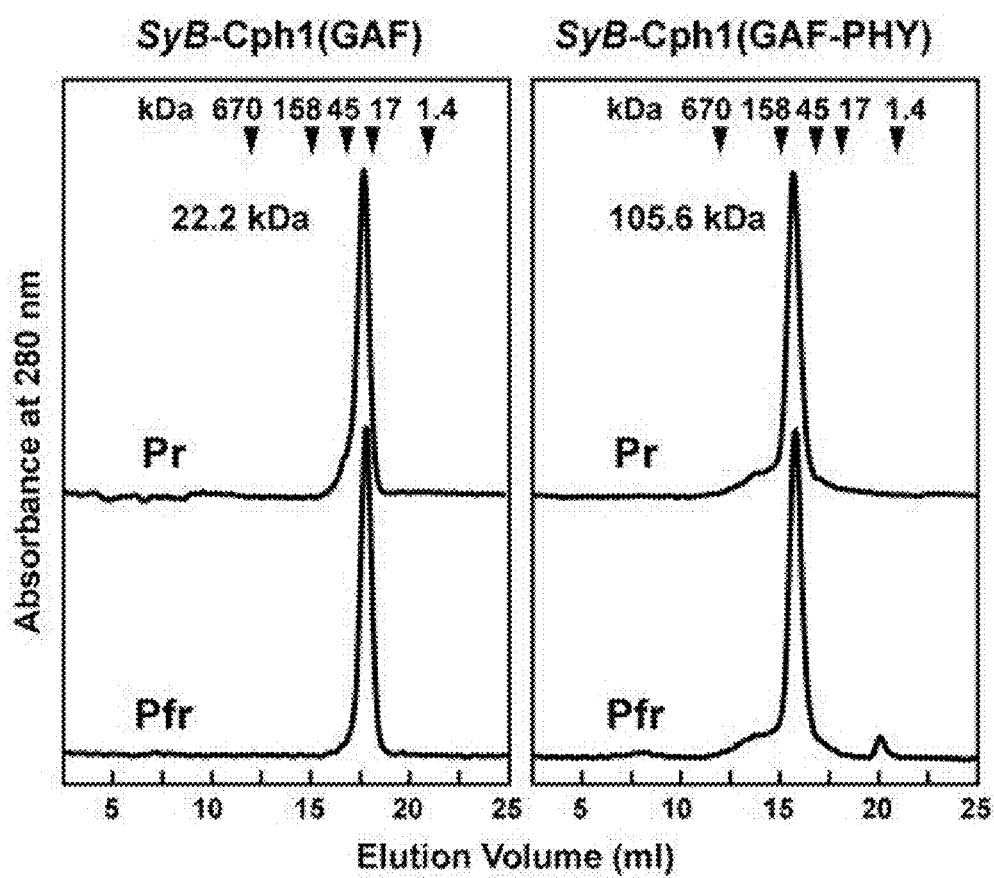
FIG. 23 shows graphs of a size exclusion chromatogram (SEC) of SyB-Cph1 (GAF) and SyB-Cph1 (GAF-PHY) chromoproteins under non-denaturing conditions as Pr or following saturating red light (mostly Pfr).

Phys from proteobacteria and fungi typically connect the HK domain directly to the PHY domain, whereas higher plant Phys have an intervening region embedded with two PAS domains. In contrast, SyA-Cph1 and SyB-Cph1 contain a second predicted GAF domain (GAF2) after the PHY domain (FIG. 14A and FIG. 22). The GAF2 sequences lack the DIP motif, the lasso loop sequence, and a number of other conserved residues present in the canonical GAF domain of Phys (see above), but do contain a cysteine (Cys-516 in SyB-Cph1) within a Cys-His-Leu motif that could interact with bilins covalently (FIGS. 22 and 23). Several other Phys from cyanobacteria (e.g., *Synechocystis* Cph2) also contain a similar GAF domain distal to the PHY domain. In the case of *Synechocystis* Cph2, this second GAF sequence can bind bilins, at least in vitro (Wu and Lagarias, 2000, *Biochemistry* 39: 13487-13495), suggesting that SyA-Cph1 and SyB-Cph1 contain two functioning bilin lyase domains.

FIG. 22 shows a sequence alignment of the HK and GAF2 domains in SyA-Cph1 and SyB-Cph1 with representatives from the Phy superfamily. FIG. 22A shows domain architectures of SyA-Cph1 and SyB-Cph1. Positions of the conserved RIT and DIP motifs, the GAF cysteine (C) that binds PCB, the conserved cysteine in GAF2, and the conserved histidine (H) that is the likely phosphoacceptor site in the HK domain are indicated. FIG. 22B shows alignment of HK domain. Brackets locate the conserved H, N, D/F, and G boxes common in HK domains. The arrowhead indicates the presumed phosphoacceptor histidine. FIG. 22C shows alignment of C-terminal GAF2 from SyA-Cph1 and SyB-Cph1 with other Phys that also contain the RIT domain. The cysteine that could bind bilins is indicated by the arrowhead. Identical and similar amino acids are shown in black and gray boxes, respectively. Dots denote gaps. Sequences in the alignments include those from SyA-Cph1 (YP_476144), SyB-Cph1 (YP_478662), related sequences from *Nostoc punctiforme* PCC73102 (ZP_00111485), *Lyngbya* sp. PCC8106 (ZP_01618934), and *Anabaena variabilis* (YP_324761).

A striking feature of the SyA-Cph1 and SyB-Cph1 architectures is the clear absence of the N-terminal PAS domain found in most bona-fide Phys identified thus far (Vierstra and Karniol, 2005, In: *Handbook of Photosensory Receptors*, Briggs and Spudich, eds., Wiley-VCH Press, Weinheim, Germany, pp 171-196). Instead, both amino acid sequences begin immediately at the start of the first GAF domain (FIG. 14). Although the contribution(s) of the PAS domain to Phy function are not yet clear, crystal structures reveal that it is in loose contact with the GAF domain through electrostatic interactions between the knot interface and the propionate side chain of the B pyrrole ring. Additional BLAST searches of the GenBank database revealed a small collection of other cyanobacterial Phys with similar domain architectures, including Cph sequences from *Nostoc punctiforme, Lyngbya, Anabaena variabilis*, and *Acaryochloris marina* (FIG. 14B and FIG. 22). Like SyA-Cph1 and SyB-Cph1, these "PAS-less" Phys contain one or two additional GAF domains downstream of the PHY domain and a 12-amino-acid conserved sequence RITX(Q/R)IR(Q/R)SLEL (SEQ ID NO:43) or RIT motif (where X is any amino acid) at the N-terminal end of the first GAF domain (residues 20-31 in SyB-Cph1 (FIG. 14B). The function of the RIT motif is unclear. The corresponding stretch in the DrphP CBD structure forms the α4 helix and α4-α5-helix linker domain, which comprise part of the three-helix bundle that may help sister GAF domains dimerize.

Analysis of the surrounding genomic region revealed that the SyA-Cph1 and SyB-Cph1 coding regions are the first part of a two-locus operon in *Synechococcus* sp. OS-A and OS-B' (FIG. 14A). The immediate 3' open reading frames (TIGR locus numbers CYA 2781 and CYB 2484), which are 4-bp downstream or overlap with the Cph1 coding region, respectively, encode small (130 residues in OS-A and 123 residues in OS-B') highly conserved proteins predicted to contain a Domain of Unknown Function 309 (DUF309). DUF309 sequences can be found in a number of archaeal, bacterial, fungal, algal, and higher plant species where they may bind metals via the consensus sequence HXXXEXXW (SEQ ID NO:44) or the consensus sequence HXXXEXXY (SEQ ID NO:45). Additional synteny is revealed by the presence of similar TatD homologs located 128- and 215-bp upstream from the SyA-Cph1 and SyB-Cph1 coding regions, respectively, which are predicted to be separate transcriptional units (FIG. 14A).

SyA-Cph1 and SyB-Cph1 Assemble with PCB to Generate Photochromic Phys.

Given their potential thermostability and the possibility that the 200-amino-acid GAF alone can complete Pr→Pfr photoconversion, SyA-Cph1 and SyB-Cph1 might be advantageous for various physico-chemical analyses of Phy-type receptors. Full-length polypeptides of both bearing a C-terminal 6His tag expressed well in *E. coli* but were completely insoluble. Truncated variants of each encompassing just the GAF domain or the GAF domain in combination with the PHY domain expressed well, were highly soluble, and could be easily purified by nickel-chelate affinity chromatography followed by hydrophobic FPLC.

Figure 15:
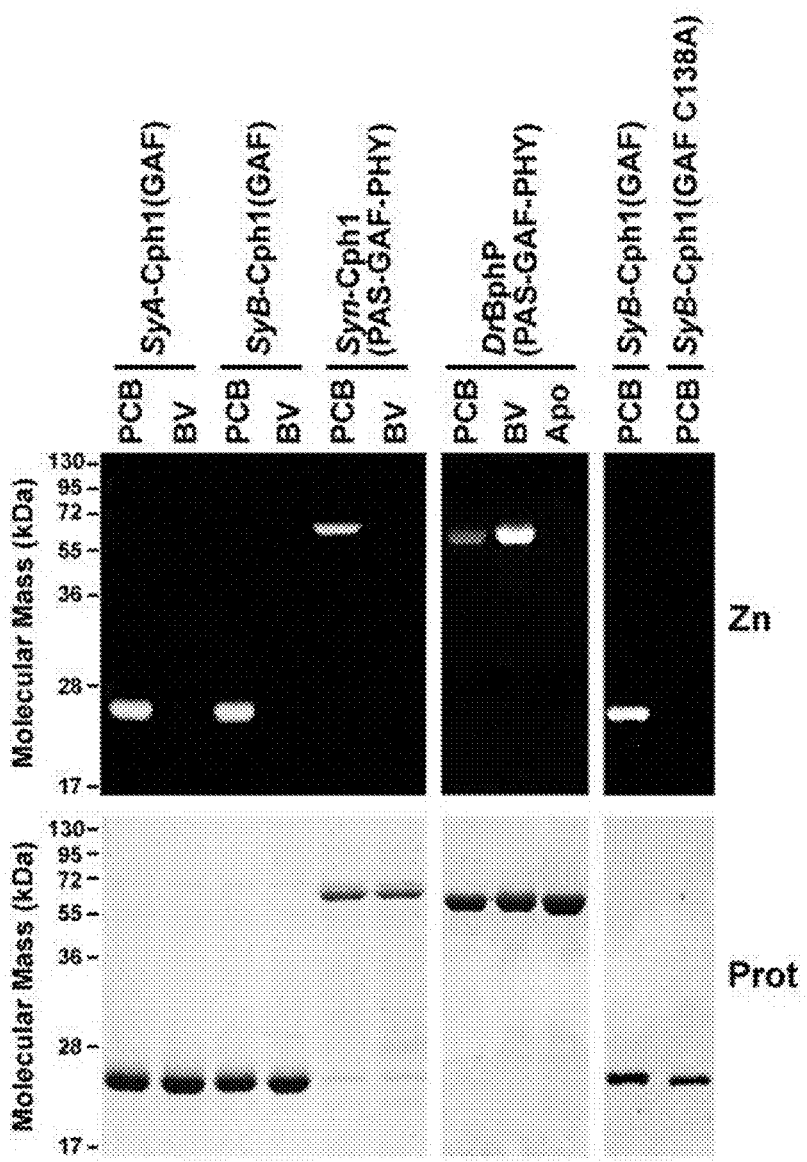
FIG. 15 is an electrophoretic image showing data from in vitro assembly of SyA-Cph1 and SyB-Cph1 with phycocyanobilin (PCB).

To test for their ability to assemble with bilins, purified SyA-Cph1 (GAF) and SyB-Cph1 (GAF) apo-proteins were incubated with PCB or BV in vitro and then assayed for covalent attachment by zinc-induced fluorescence of the products following SDS-PAGE. FIG. 15 shows in vitro assembly of SyA-Cph1 and SyB-Cph1 with PCB. Recombinant GAF polypeptides from SyA-Cph1 and SyB-Cph1, SyB-Cph1 GAF polypeptide where Cys-138 was substituted for an alanine, and PAS-GAF-PHY polypeptides from *D. radiodurans* (DrBphP) and *Synechocystis* (Syn) were incubated with PCB or BV and purified by nickel-chelate affinity chromatography. Samples were subjected to SDS-PAGE and either assayed for the bound bilin by zinc-induced fluorescence (Zn), or stained for protein with Coomassie Blue (Prot). Apo, apo-protein before incubation with the bilins.

As can be seen in FIG. 15, these GAF only constructions, like a PAS-GAF-PHY fragment from the cyanobacterial Phy Cph1 from *Synechocystis*, readily bound PCB but not BV. In contrast, a PAS-GAF-PHY fragment from the bacterio-Phy DrBphP bound only BV under identical conditions, consistent with its preference for BV as the chromophore. Sequence alignments with other members of the Phy superfamily identified Cys-138 as the likely bilin attachment site for SyA-Cph1 and SyB-Cph1 (FIG. 14B). In support, a Cys-138 to alanine substitution in SyB-Cph1 effectively abrogated PCB ligation (FIG. 15).

Figure 16:
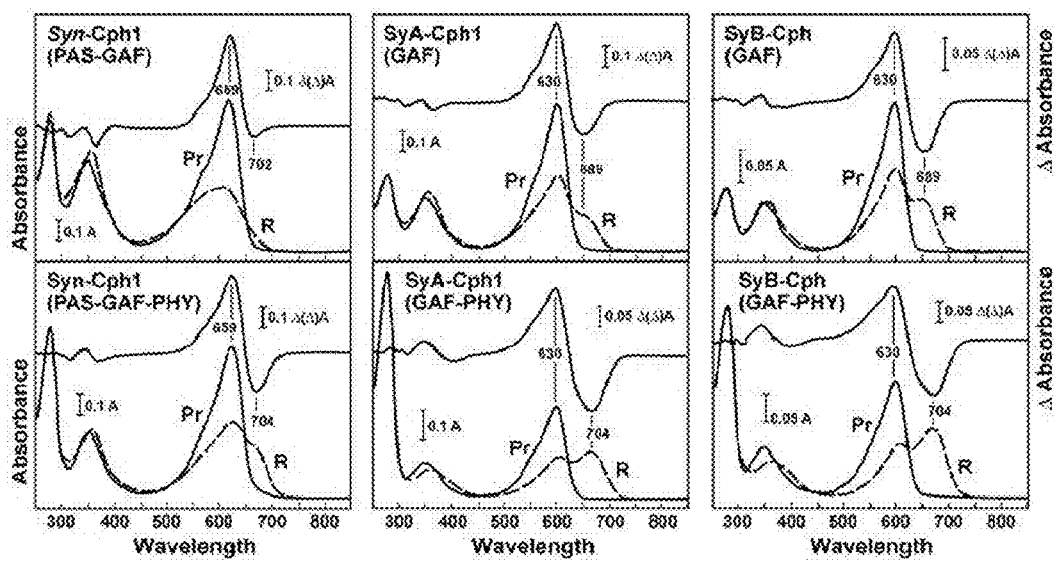
FIG. 16 shows graphs of UV-vis absorption spectra of PCB-assembled SyA-Cph1 and SyB-Cph1 encompassing only the GAF domain or the GAF-PHY region as Pr (solid lines) or following saturating red light (R) irradiation (mostly Pfr, dashed lines).

To scale-up SyA-Cph1 and SyB-Cph1 chromoprotein production, the dual-plasmid *E. coli* system of Gambetta and Lagarias was exploited (Gambetta and Lagarias, 2001, *Proc. Natl. Acad. Sci. USA* 98: 10566-10571). This system co-expresses the apo-protein with the HO and BVR enzymes needed to synthesize PCB from heme. FIG. 16 shows the UV-vis absorption spectra of PCB-assembled SyA-Cph1 and SyB-Cph1 encompassing only the GAF domain or the GAF-PHY region as Pr (solid lines) or following saturating red light (R) irradiation (mostly Pfr, dashed lines). Pr-minus-Pfr difference spectra with their maxima and minima are shown above. The absorption and difference spectra of PAS-GAF and PAS-GAF-PHY regions of Syn-Cph1 assembled with PCB are included for comparison.

Absorption spectra of the resulting in vivo assembled photoreceptors, either spanning the GAF-PHY region or just the GAF domain, resembled typical Phys and were photochromic following red and far-red light irradiations (FIG. 16). The Pr absorption spectra of the GAF-PHY fragments had maxima at 629 nm for the Q bands, which were substantially blue shifted relative to the Pr form generated by the PAS-GAF-PHY or PAS-GAF fragments from Syn-Cph1 with absorption maxima at 659 nm (FIG. 16). Saturating red light irradiations of the GAF-PHY fragments from SyA-Cph1 and SyB-Cph1 converted most Pr to Pfr with absorption maxima at 704 nm, much like Syn-Cph1 (PAS-GAF-PHY) (FIG. 16). In contrast to truncations of other Phys missing the PHY domain, including Syn-Cph1 and DrBphP that are poorly photochromic (FIG. 16), the SyA-Cph1(GAF) and SyB-Cph1(GAF) constructions retained most of their red/far-red light photoreversibility. Saturating red light transformed a substantial portion of the PCB-bound GAF polypeptides to a species resembling Pfr. This photoconversion was more efficient for SyB-Cph1 (GAF) which produced a defined Pfr absorption peak at 689 nm in saturating red light (FIG. 16).

SEC has shown that most, if not all, Phys are dimeric with their binding interface(s) involving one or more regions, including the GAF domain in DrBphP, the PAS-GAF-PHY domain in Syn-Cph1, and the C-terminal HK and HK-related regions in microbial and higher plants Phys. Similar SEC analysis of the GAF and GAF-PHY constructions of SyB-Cph1 assembled with PCB indicated that the PHY domain helps this chromoprotein dimerize. Whereas the GAF domain alone as Pr behaved as a monomer of 22 kDa, consistent with its calculated molecular mass of 23.3 kDa, the GAF-PHY fragment behaved as a dimer species at 105-kDa, nearly twice the size of its calculated mass of 48.4 kDa (FIG. 23). Shown in FIG. 23 is a size exclusion chromatogram (SEC) of SyB-Cph1 (GAF) and SyB-Cph1 (GAF-PHY) chromoproteins under non-denaturing conditions as Pr or following saturating red light (mostly Pfr). Arrowheads indicate the elution positions of standards thyroglobulin (608 kDa), gamma globulin (158 kDa), ovalbumin (45 kDa), myglobulin (17 kDa), and biotin (1.4 kDa). The predicted molecular masses of monomeric SyB-Cph1 (GAF) and SyB-Cph1 (GAF-PHY) polypeptides are 23.3 kDa and 48.4 kDa, respectively, while the apparent molecular masses measured by SEC are 22 and 106 kDa, respectively. The SEC elution profiles of both GAF and GAF-PHY constructions of SyB-Cph1 were indistinguishable following exposure to saturating red light, suggesting that their overall shapes and dimerization status are not dramatically altered upon photoconversion to Pfr (FIG. 23).

SyA-Cph1 and SyB-Cph1 are Thermostable.

*Synechococcus* sp. OS-A and OS-B' grow well between 54° C. and 63° C. with an optimum growth temperature of 60° C. By exposing recombinant SyA-Cph1 and SyB-Cph1 chromoproteins to a wide range of temperatures, it was confirmed that the photoreceptors are likewise thermotolerant and could withstand temperatures exceeding 70° C.

Figure 17:
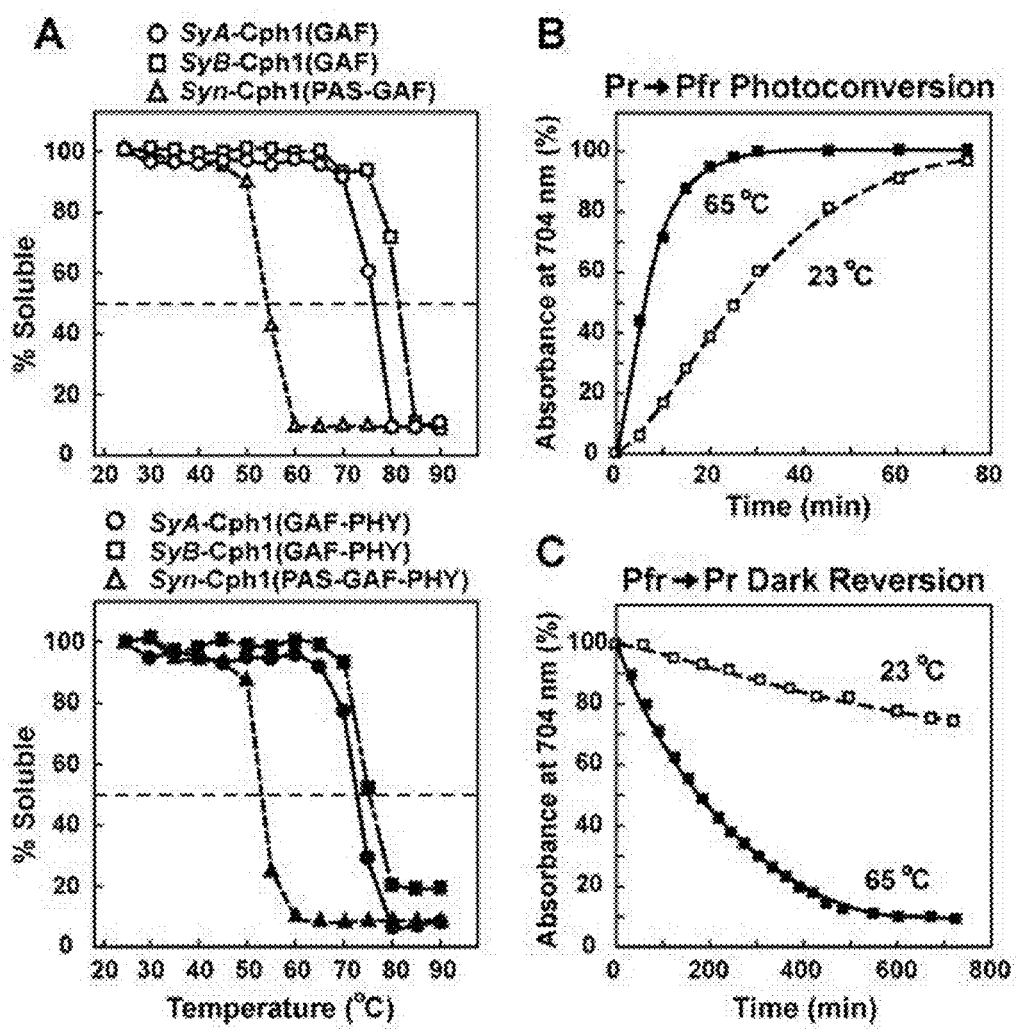
FIG. 17 shows graphs of thermostability of the SyA-Cph1 and SyB-Cph1 chromoprotein: A, Solubility of the chromoproteins upon exposure to increasing temperatures. B and C, Effect of temperature (23° C. versus 65° C.) on Pr→Pfr photoconversion by red light irradiation (B) and Pfr→Pr dark reversion (C) of SyB-Cph1 (GAF) assembled with PCB.

FIG. 17 shows the thermostability of the SyA-Cph1 and SyB-Cph1 chromoprotein. Recombinant GAF and GAF-PHY fragments of SyA-Cph1 and SyB-Cph1 were assembled with PCB in vivo and purified by nickel-chelate affinity chromatography. FIG. 17A shows the solubility of the chromoproteins upon exposure to increasing temperatures. PAS-GAF and PAS-GAF-PHY fragments of Syn-Cph1 from the mesophillic *Synechocystis* PCC6803 species are included for comparison. FIGS. 17B and C shows the effect of temperature (23° C. versus 65° C.) on Pr→Pfr photoconversion by red light irradiation (B) and Pfr→Pr dark reversion (C) of SyB-Cph1 (GAF) assembled with PCB.

The GAF constructions of SyA-Cph1 and SyB-Cph1 had denaturation temperatures (temperature where 50% of the protein becomes insoluble) of 76° C. and 83° C., respectively, which decreased slightly to 72° C. and 76° C., respectively, upon inclusion of the PHY domain (FIG. 17A). By contrast, the PAS-GAF and PAS-GAF-PHY chromoproteins from Syn-Cph1, which were derived from the mesophilic *Synechocystis* PCC6803 species, denatured at 54° C. and 53° C., respectively (FIG. 17A).

Figure 24:
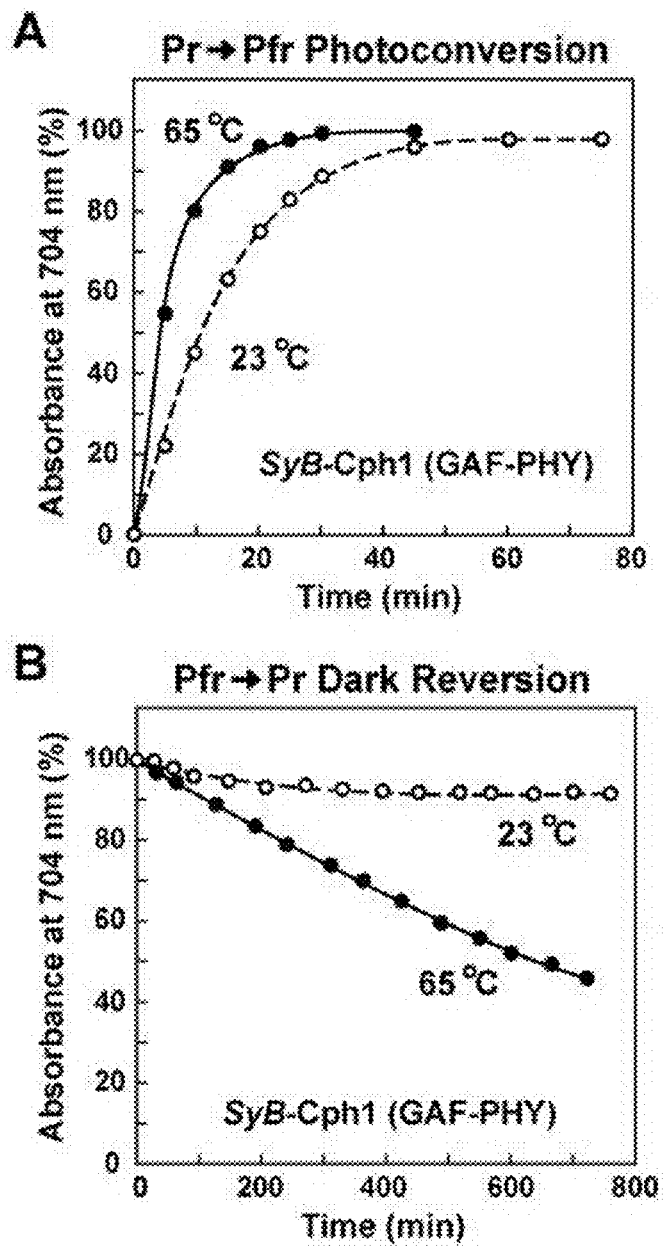
FIG. 24 shows graphs of the effect of temperature (23° C. and 65° C.) on Pr→Pfr photoconversion by saturating red light (A) and Pfr→Pr dark reversion (B) of SyB-Cph1 (GAF-PHY) assembled with PCB.

Thermostable enzymes typically work more efficiently at higher temperatures, with optimal performance often matching the preferred growth temperature of the host organism. This expectation may also hold true for the Pr/Pfr interconversion of SyA-Cph1 and SyB-Cph1. Both the GAF and GAF-PHY constructions of SyB-Cph1 were more efficient at Pr→Pfr photoconversion at 65° C. versus 23° C. using the same fluence rate of red light (initial rates increased by ~3 and 2 fold, respectively (FIG. 17B and FIG. 24). Shown in FIG. 24 is the effect of temperature (23° C. and 65° C.) on Pr→Pfr photoconversion by saturating red light (FIG. 24A) and Pfr→Pr dark reversion (FIG. 24B) of SyB-Cph1 (GAF-PHY) assembled with PCB. Since the primary photochemical event is temperature independent, much of this increased rate should reflect accelerated thermal relaxation steps from the lumi-R intermediate to Pfr. Subsequent Pfr→Pr thermal reversion of the GAF chromoprotein was also faster at 65° C. versus 23° C., with the initial rate increased by 9-fold at the higher temperature (FIG. 17C). Surprisingly, little thermal reversion occurred at 23° C. for the GAF-PHY construction of SyB-Cph1 even after 12 hrs of dark incubation (FIG. 24), suggesting that even lower temperatures might effectively stabilize the Pfr form of this fragment.

Use of SyB-Cph1 (GAF) Chromoproteins as Fluorophores.

The discovery of a set of SyB-Cph1 mutants that emit red fluorescence may have utility in various cell biological and molecular assays as small portable fluorescent tags. In particular, the SyB-Cph1 (PAS-GAF D86H) mutant emits strong fluorescence and when directly compared was significantly brighter than the previously reported Y176H mutant generated with the PAS-GAF-PHY fragments of *Synechocystis* Cph1 (FIG. 13).

Figure 13:
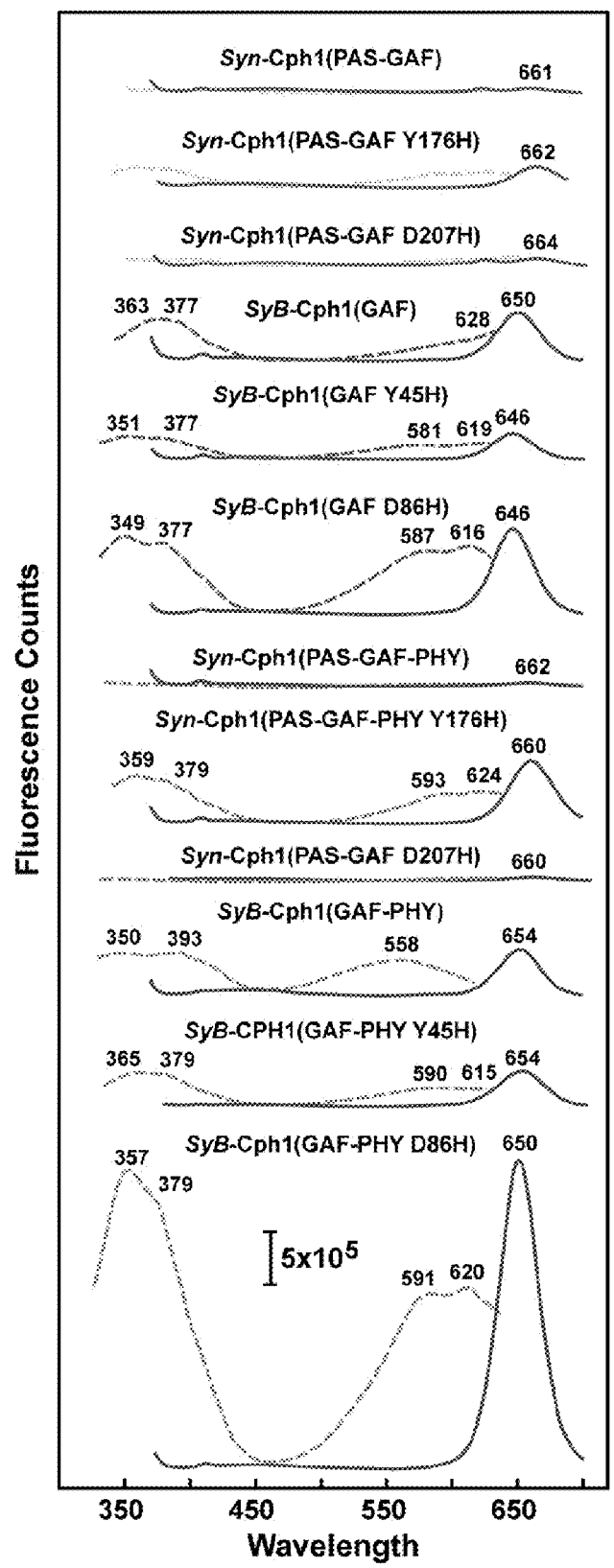
FIG. 13 is a composite graph depicting UV-irradiated and fluorescent scans of various Cph1 (C) and CYB (B) chromoprotein constructs with wild-type, Asp>H (D) or Tyr>H (Y) mutations within their respective DrBphP coordinates of Asp207 and Tyr176.

Fluorescence characteristics of the tyrosine and aspartic acid substitutions in Syn-Cph1 and SyB-Cph1 are shown in FIG. 13, which indicates various UV-irradiated Cph1 (C) and CYB (B) chromoprotein constructs with wild-type, Asp>H (D) or Tyr>H(Y) mutations within their respective DrBphP coordinates of Asp207 and Tyr176. All samples were adjusted to have a 0.6 absorbance at the Pr absorption maximum. Top panels in FIG. 13 show purified solutions in white light (WL) and upon irradiation with UV light. Bottom spectra in FIG. 13 show fluorescence excitation (dashed lines) and emission spectra (solid lines) of the chromoprotein samples shown in panel A. Excitation and emission maxima are indicated. CYB is thermostable *Cyanobacteria Yellowstone B'*. In particular, CG refers to cph1 PAS-GAF; CGY refers to cph1 PAS-GAF with a Tyr>His mutation; CGD refers to cph1 PAS-GAF with a Asp>His mutation; BG refers to CYB GAF; BGY refers to CYB GAF with a Tyr>His mutation; BGD refers to CYB GAF with a Asp>His mutation; CP refers to cph1 PAS-GAF-PHY; CPY refers to cph1 PAS-GAF-PHY with a Tyr>His mutation; CPD refers to cph1 PAS-GAF-PHY with a Asp>H mutation; BP refers to CYB GAF-PHY; BPY refers to CYB GAF-PHY with a Tyr>His mutation; and BPD refers to CYB GAF-PHY with a Asp>His mutation (FIG. 13). As shown in FIG. 13, the Asp207>His207 mutation is more fluorescent than the Tyr176>His176 mutation. In addition, there was greater amount of fluorescent emission with CYB, especially the CYB GAF-PHY construct harboring the Asp>His mutation (bottom graph, BPD). The D86H mutant retains its red fluorescence in a monomeric truncation that encompasses only the 200-amino acid GAF domain, thus making this fluorophore even smaller than the commonly used green fluorescent protein (GFP). Advantages over other fluorophores such as GFP include: (i) its remarkable thermostability, (ii) the large separation of the electronically excited state (Soret transition at 380 nm) from the emitting state (650 nm), which would minimize light contamination, and (iii) the ability to modify fluorescence in both time and space by controlling PCB (or any other adduct which emits fluorescence as a result of binding the apoprotein) availability (Miller et al., 2006, *Proc. Natl. Acad. Sci. USA* 103: 11136-11141). The D86H mutant may also be excited in the first electronic transition with orange light to produce an identical emission peak, thus circumventing potential damages/effects induced by UV or blue-light excitation.

SvB-Cph1 Mutant Affecting Asp-86 Emit Intense Red Fluorescence.

Random and structurally guided mutagenesis of bacterial Phys has identified a number of conserved residues that interfere with the photoinduced Pr→Pfr conversion. As examples, replacement of Tyr-176 in Syn-Cph1 with a histidine generates a highly red fluorescent chromoprotein that cannot photoconvert to Pfr (25,46), while various substitutions of Asp-207 (e.g., D207H variant) block Pr→Pfr photoconversion in DrBphP (Wagner et al., 2008, *J. Biol. Chem.* 283: 12212-12226). To further compare the binding pocket of these PAS-less Phys relative to more typical Phys, analogous mutations (Y54H and D86H; FIG. 14B) were introduced into the GAF and GAF-PHY constructions of SyB-Cph1.

Figure 18A:
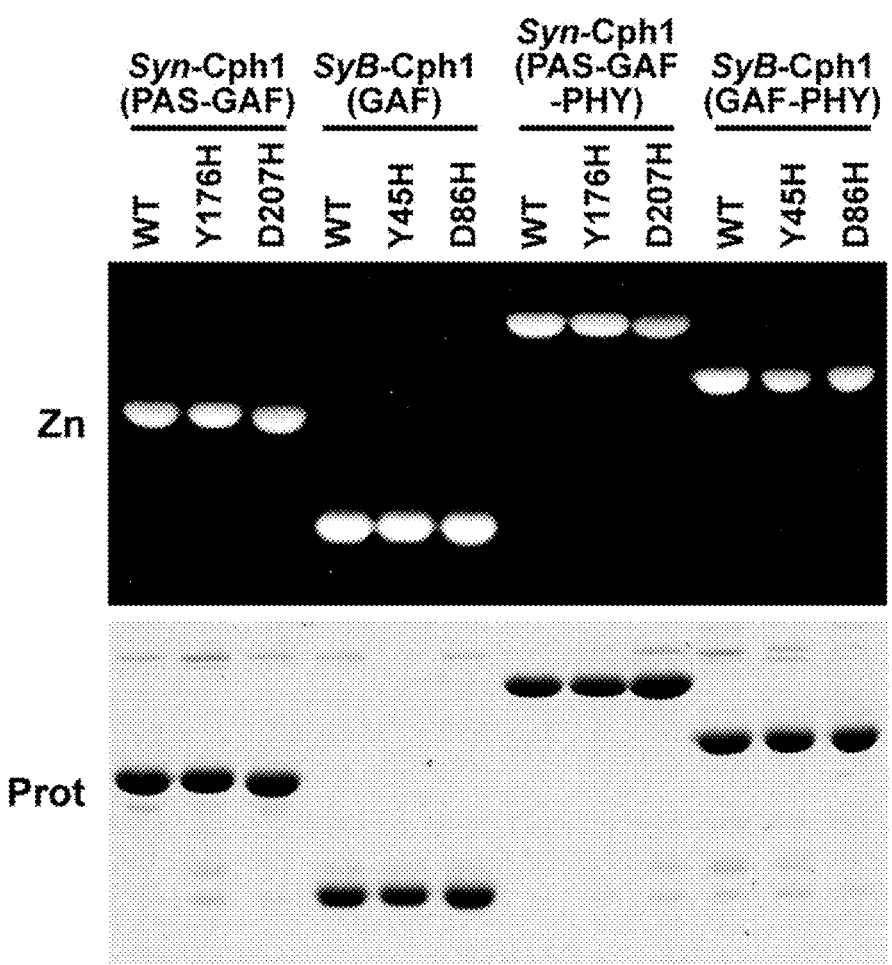
FIG. 18 shows an electrophoretic image (A) of the effects of positionally conserved tyrosine and aspartic acid residues in the GAF domains of SyB-Cph1 and Syn-Cph1 on assembly with PCB; and graphs (B) of UV-vis absorption spectra of the resulting chromoproteins.
Figure 18B:
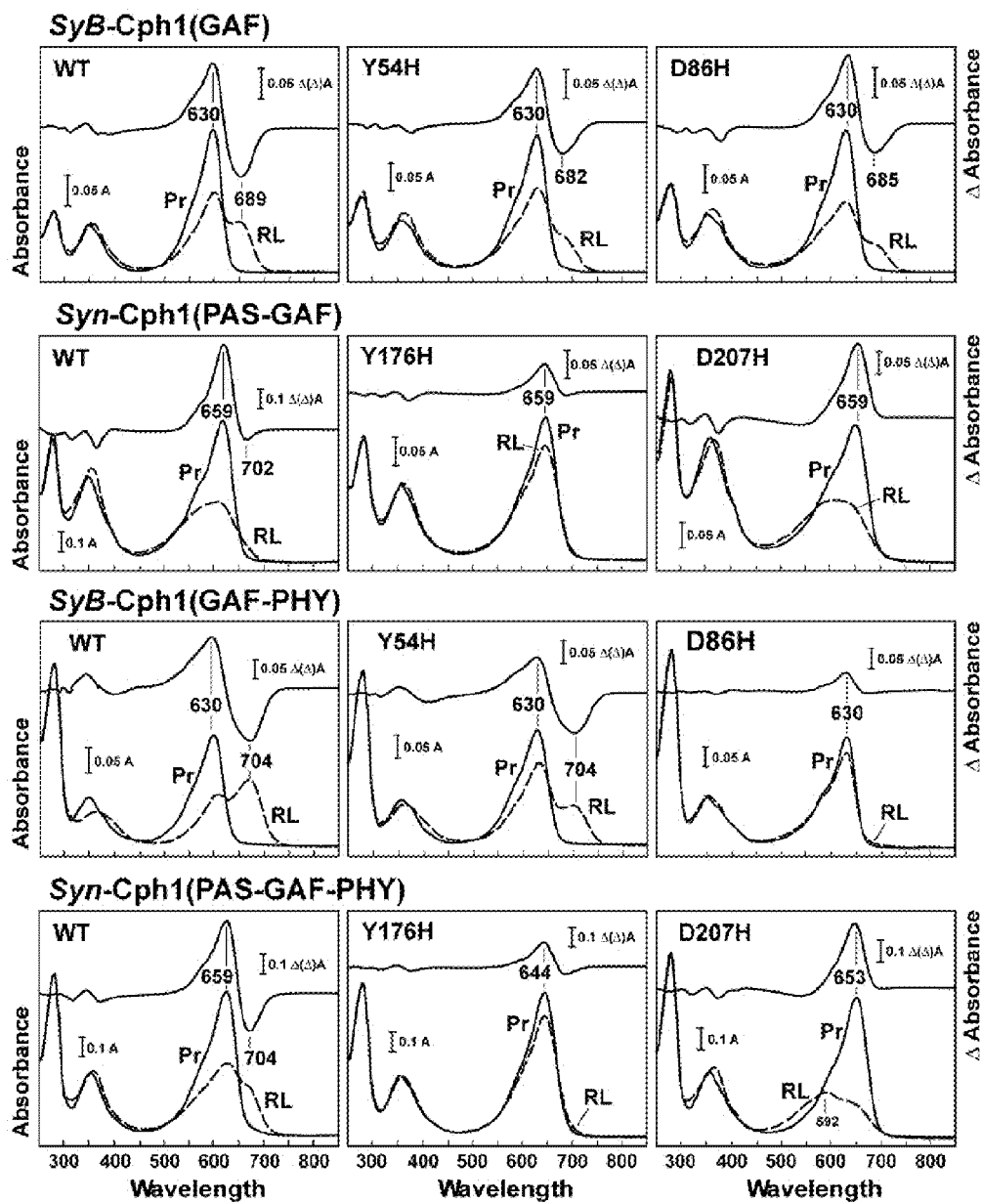

FIG. 18 shows the effects of positionally conserved tyrosine and aspartic acid residues in the GAF domains of SyB-Cph1 and Syn-Cph1 on assembly with PCB and absorption spectra of the resulting chromoproteins. GAF and GAF-PHY polypeptides from SyB-Cph1 and PAS-GAF and PAS-GAF-PHY polypeptides from Syn-Cph1 bearing histidine substitutions for the tyrosine (residue 54 and 176 in SyB-Cph1 and Syn-Cph1, respectively) or aspartic acid (residue 86 and 207 in SyB-Cph1 and Syn-Cph1, respectively) were co-expressed with PCB, and purified by nickel-chelate affinity chromatography. FIG. 18A shows the ability of the mutant apo-proteins to bind PCB. Samples were subjected to SDS-PAGE and either assayed for the bound bilin by zinc-induced fluorescence (Zn) or stained for protein with Coomassie Blue (Prot). FIG. 18B shows the UV-vis absorption spectra of the mutants shown in FIG. 18A as Pr (solid lines) or following saturating red light (R) irradiation (mostly Pfr, dashed lines). Pr-minus-Pfr difference spectra with their difference maxima and minima are shown above.

Both sets of Y54H and D86H variants in SyB-Cph1 were soluble, retained their ability to bind PCB (FIG. 18A), and generated near normal absorption spectra for the Pr state with Q band maxima at or near 630 nm (FIG. 18B), in agreement with prior studies with other Phys showing that these residues do not significantly affect Pr assembly. However, absorption spectra recorded after red light irradiation revealed substantial photochemical defects in the variants (FIG. 18B). For the SyB-Cph1 (GAF) chromoprotein, both substitutions reduced the amount of Pfr accumulation at 689 nm, but the reduction was not accompanied by a concomitant loss in the Pr peak, suggesting that photoconversion in these constructs might not actually have been lost.

In contrast, while only a minor effect on Pfr accumulation was evident in the SyB-Cph1 (GAF-PHY) construction bearing the Y54H substitution, a strong block in photoconversion was evident for the D86H substitution. The Pr absorption spectrum of this variant was only slightly changed by saturating red light, and the small loss of absorbance at 630 nm that was observed was not associated with a concomitant increase in absorption in the far-red wavelength region for Pfr, indicating that most Pr→Pfr photoconversion was inhibited.

Similar photochromic defects were evident in comparable substitutions of Syn-Cph1 (both PAS-GAF and PAS-GAF-PHY truncations), but the effects were stronger with the tyrosine variants (FIG. 18). In agreement with previous studies (Fischer and Lagarias, 2004, *Proc. Natl. Acad. Sci. USA* 101: 17334-17339), the Y176H variant introduced into both Syn-Cph1 constructions strongly compromised Pr→Pfr photoconversion with saturating red light generating little or no Pfr. By contrast, the absorption spectrum of the Syn-Cph1 (PAS-GAF D207H) variant after treatment with saturating red light produced a similar "bleached" photoproduct to its wild-type counterpart. The Syn-Cph1 (PAS-GAF-PHY D207H) mutant also retained its ability to photoconvert in red light, but instead of generating the far-red light-absorbing Pfr-like state, it transformed to an unexpected blue-shifted species with a well-defined absorption maximum at 592 nm.

When the fluorescent properties of the set of SyB-Cph1 and Syn-Cph1 variants were analyzed, similar differential defects were observed that roughly paralleled the effects of the variants on Pr→Pfr photoconversion (FIG. 13). In accord with previous studies, introduction of the Y176H mutation into either the PAS-GAF or PAS-GAF-PHY constructions of Syn-Cph1 generated red fluorescent chromoproteins with strong emission maxima at 662 nm. The PAS-GAF-PHY Y176H variant was approximately three times more fluorescent than the equivalent PAS-GAF construction. Neither the wild-type chromoproteins nor constructions bearing the D207H mutation were fluorescent.

The opposite trend existed for SyB-Cph1 even though the overall fluorescence yield was much greater for this Phy (FIG. 13). The wild-type GAF and GAF-PHY constructions of SyB-Cph1 and the corresponding Y54H substitutions displayed moderate fluorescence, with emission maxima at 646-654 nm. In contrast, the D86H substitutions were substantially more fluorescent with the SyB-Cph1 (GAF-PHY D86H) variant showing especially strong fluorescence output. Excitation maxima were evident at 357, 379, 591 and 620 nm with a single emission peak at 650 nm. By comparing fluorescence emission using equivalent amounts of chromoprotein (based on equal absorbance of the Pr Q band), the SyB-Cph1 (GAF-PHY D86H) chromoprotein was ~3.5 times more fluorescent than the comparable chromoprotein without the PHY domain and was 5 times more fluorescent when compared to the Syn-Cph1 (PAS-GAF-PHY Y176H) chromoprotein.

Resonance Raman (RR) Spectroscopy of SyB-Cph1.

The sequence homology within the GAF domains of SyA-Cph1 and SyB-Cph1 relative to more typical Phys strongly suggested that these PAS-less Phys adopt similar bilin geometry and employ a similar reaction mechanism to generate Pfr from Pr, including the use of a deprotonation/reprotonation cycle during the relaxation steps from the initial intermediate photoproduct (Lumi-R) to Pfr. To help support these possibilities RR spectroscopy was employed to assess bilin conformation and protonation state. In particular, RR bands in the region between 1500 and 1700 $cm^{-1}$ can (i) help predict the methine bridge configurations and conformations (i.e. ZIE and synlanti geometries), (ii) reveal the protonation state of the pyrrole nitrogens in the Pr and Pfr states, and (iii) detect the accumulation of transformation intermediates if complete photoconversion stalls (e.g., deprotonated Meta-$R_c$ intermediate). Moreover, by comparing the RR spectra of the GAF and GAF-PHY constructions it was possible to define the importance of the PHY domain during Pr→Pfr photoconversion for these thermostable PAS-less Phys.

Figure 19:
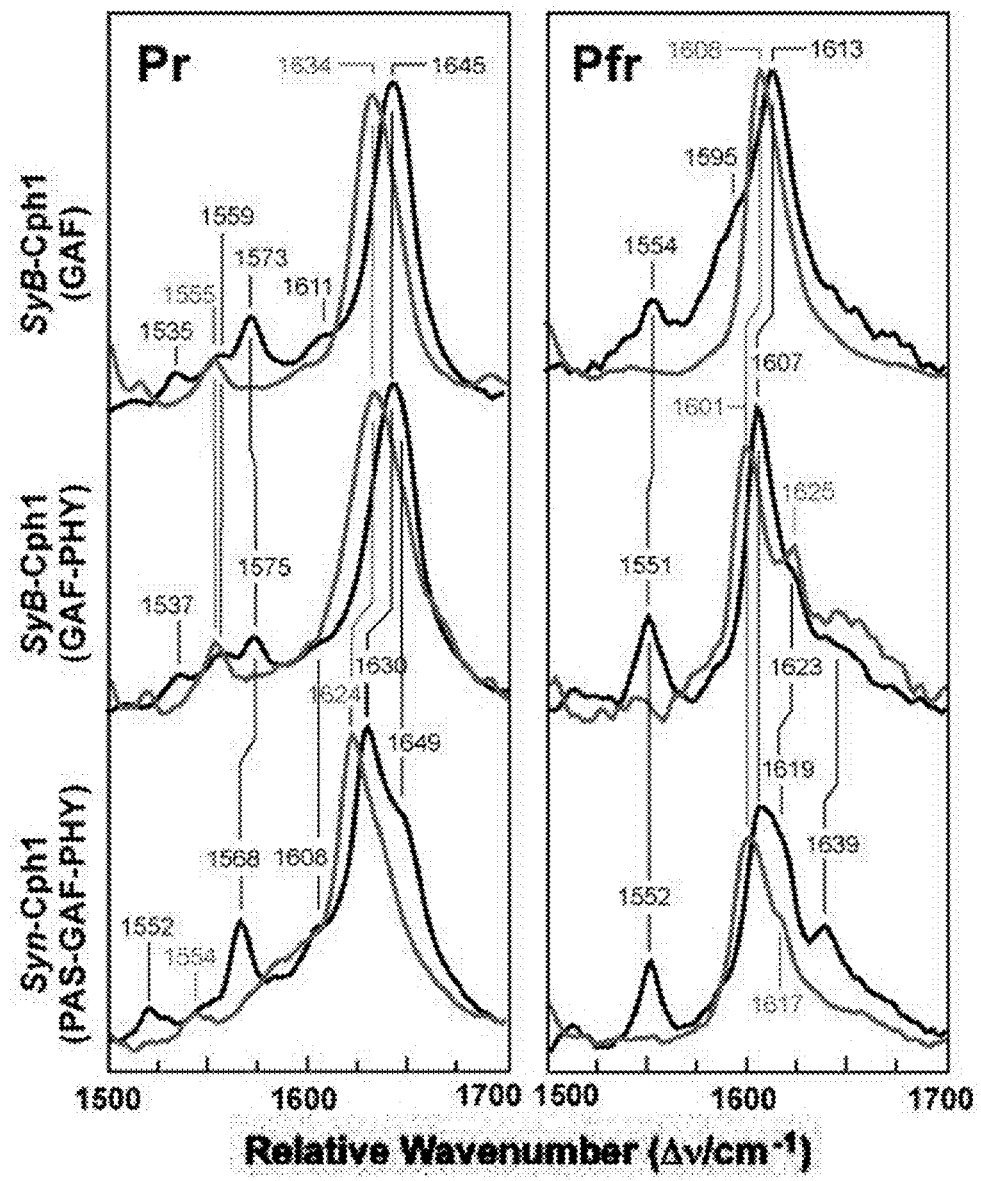
FIG. 19 shows graphs of the Resonance Raman (RR) spectra of the Pr and Pfr forms of the GAF and GAF-PHY fragments of SyB-Cph1 as compared to the PAS-GAF-PHY fragment from *Synechocystis* (Syn).

FIG. 19 shows the Resonance Raman (RR) spectra of the Pr and Pfr forms of the GAF and GAF-PHY fragments of SyB- Cph1 as compared to the PAS-GAF-PHY fragment from *Synechocystis* (Syn). RR spectra were recorded between 1500 and 1700 cm$^{-1}$ for Pr (left panel) and after saturating red light (Pfr, right panel). Samples were measured in the presence of H$_2$O (black lines) or D$_2$O (grey lines). The positions of the pyrrole N—H ip modes are marked by the arrows. RR spectra for Syn-Cph1 (PAS-GAF-PHY) were taken from Remberg et al, 1997, *Biochemistry* 36: 13389-13395.

Figure 25:
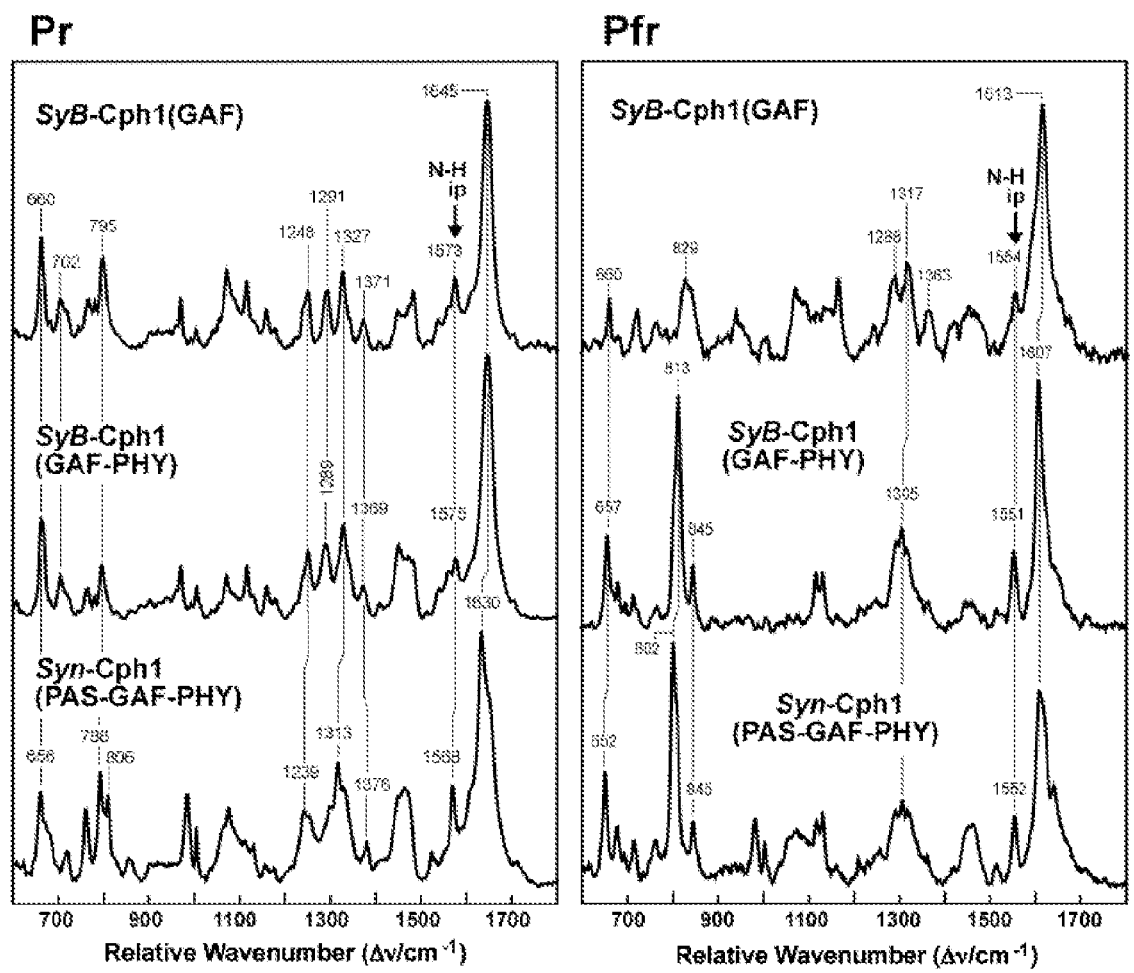
FIG. 25 shows graphs of Resonance Raman (RR) spectra of the Pr and Pfr forms of the GAF and GAF-PHY fragments of SyB-Cph1 as compared to the PAS-GAF-PHY fragment from *Synechocystis* (Syn) Cph1.

As shown in FIG. 25, the RR spectra of the Pr state of SyB-Cph1 (GAF) and SyB-Cph1 (GAF-PHY) displayed very similar overall vibrational band patterns. Shown in FIG. 25 is a Resonance Raman (RR) spectra of the Pr and Pfr forms of the GAF and GAF-PHY fragments of SyB-Cph1 as compared to the PAS-GAF-PHY fragment from *Synechocystis* (Syn) Cph1. RR spectra between 600 and 1800 cm$^{-1}$ for Pr (left panel) and following saturating irradiation with red light (Pfr, right panel) were measured in the presence of H$_2$O (black lines) or D$_2$O (grey lines). The positions of the pyrrole N—H ip modes are marked by the arrows. RR spectra for Syn-Cph1 (PAS-GAF-PHY) were taken from Remberg et al., 1997, *Biochemistry* 36: 13389-13395. These data agreed with previous studies demonstrating that the PHY domain has little impact on Pr absorption and bilin geometry. In particular, RR bands attributed to the methine bridge geometry of PCB (1600-1650 cm$^{-1}$) and subtle details of the bilin structure (600-900 cm$^{-1}$) were identical or very similar for SyB-Cph1 (GAF) and SyB-Cph1(GAF-PHY) (FIG. 19 and FIG. 25). The N—H in-plane bending (ip) mode of pyrrole rings B and C in Pr, assigned based on its disappearance in D$_2$O, was at nearly the same position for both chromoproteins (1573 versus 1575 cm$^{-1}$; FIG. 19). These data imply that PCB retained its protonation (cationic) state and that its hydrogen bond interactions with the protein environment were for the most part unaffected by removal of the PHY domain. Only subtle differences were evident in the region between 1400 and 1500 cm$^{-1}$, which could reflect slightly greater contributions from protein Raman bands in the SyB-Cph1 (GAF-PHY) preparations (FIG. 25).

The RR spectra of the Pr state of SyB-Cph1 (GAF) and SyB-Cph1 (GAF-PHY) differed from that obtained with Syn-Cph1 (PAS-GAF-PHY), suggesting that subtle differences in bilin geometry exist between the two Cph classes. The marker band region for protonated bilins (1600-1650 cm$^{-1}$) is usually dominated by two species originating from the C=C stretching modes of the ring A-B and C-D methine bridges; these can be seen as a prominent band (1630 cm$^{-1}$) and a shoulder (1649 cm$^{-1}$) in the RR spectrum of Syn-Cph1(PAS-GAF-PHY) (FIG. 19). However, for SyB-Cph1(GAF) and SyB-Cph1(GAF-PHY), the 1630-cm$^{-1}$ band seems to be upshifted to nearly coincide with the higher-frequency mode, thus creating a single symmetric band at 1645 cm$^{-1}$ (FIG. 19). This shift most likely reflects a conformational difference at the C-D bridge as compared to Syn-Cph1 (PAS-GAF-PHY). This structural difference may also affect hydrogen bonding of the ring-C N—H group as indicated by the 7-cm$^{-1}$ higher ip frequency of the N—H group for SyB-Cph1 (GAF-PHY) (1575 cm$^{-1}$) compared to Syn-Cph1 (PAS-GAF-PHY) (1568 cm$^{-1}$). In contrast, RR spectra provide no indication for structural differences at the A-B and B-C methine bridges since the corresponding stretching bands at 1649 cm$^{-1}$ (A-B) and 1609 cm$^{-1}$ (B-C) were largely unchanged in SyB-Cph1 (GAF-PHY) versus Syn-Cph1 (PAS-GAF-PHY) (FIG. 19).

Differences in absorption spectra of SyB-Cph1 (GAF) and SyB-Cph1 (GAF-PHY) following red light suggested that the GAF-only chromoprotein is not fully competent in forming Pfr (FIG. 16). However, in contrast to other bacterial Phys that lack the PHY domain, RR spectra revealed the SyB-Cph1 (GAF) fragment does not arrest in a Meta R$_c$-like intermediate upon red light irradiation. Instead, several signature RR bands of the SyB-Cph1 (GAF) photoconversion product were consistent with the accumulation of Pfr. Included were a drastic downshift of the C-D methine bridge stretching from 1645 cm$^{-1}$ in Pr to 1613 cm$^{-1}$ and the rings B and C N—H ip mode at 1554 cm$^{-1}$ that is characteristic of the protonated Pfr state (FIG. 19). Only the shoulder at ~1595 cm$^{-1}$ on the low-frequency side of the prominent 1608-cm$^{-1}$ peak in the RR spectrum of the Pfr-like state of SyB-Cph1 (GAF) is reminiscent of a Meta-Rc-like species (FIG. 19). However, this band was not observed in D$_2$O leaving its assignment ambiguous.

The most significant difference in the RR spectra of the photoconversion products between the GAF and GAF-PHY constructions of SyB-Cph1 was a large intensity reduction in the band at ~813 cm$^{-1}$ (FIG. 25). This band originates from the C—H out-of-plane mode of the C-D methine bridge; its high RR intensity, which is a typical feature of the Pfr chromophore, may reflect torsion of the C-D methine bridge. Furthermore, the A-B stretching cannot be identified as a distinct peak or shoulder in SyB-Cph1 (GAF) but may overlap with the dominant 1613-cm$^{-1}$ band. Instead, the RR spectra of the Pfr states for SyB-Cph1 (GAF-PHY) and Syn-Cph1 (PAS-GAF-PHY) display two bands at ~1620 and 1640 cm$^{-1}$ which both are possible candidates for the A-B stretching pointing to a conformational heterogeneity at the A-B methine bridge. These differences suggest that the PHY domain subtly affects the chromophore-protein architecture of SyB-Cph1 in the Pfr state with respect to the structural details of the A-B and C-D methine bridges.

One-Dimensional and Two-Dimensional NMR Analysis of PCB Bound to SyB-Cph1 (GAF).

The fact that the 200-amino acid GAF domain of SyB-Cph1 retains its bilin lyase activity and most of its red/far-red photochromicity combined with its monomeric state, indicated that this fragment could help visualize by NMR spectroscopy global movements of a Phy chromophore and its binding pocket during phototransformation. Using the dual expression system (Gambetta and Lagarias, 2001, *Proc. Natl. Acad. Sci. USA* 98: 10566-10571), SyB-Cph1 (GAF) holoproteins were synthesized and assembled, in which either PCB or the polypeptide were labeled individually with $^{15}$N and/or $^{13}$C. Incorporation of isotopically labeled PCB into unlabeled protein was accomplished by replacing the bilin precursor ALA, added in excess to the growth medium, with either $^{15}$N- or $^{13}$C-labeled derivatives. Incorporation of $^{15}$N and $^{13}$C into the polypeptide was achieved by replacing NH$_4$Cl and glycerol in the medium with $^{15}$N- and $^{13}$C-labeled counterparts, respectively, together with an excess of unlabeled ALA.

Figure 20:
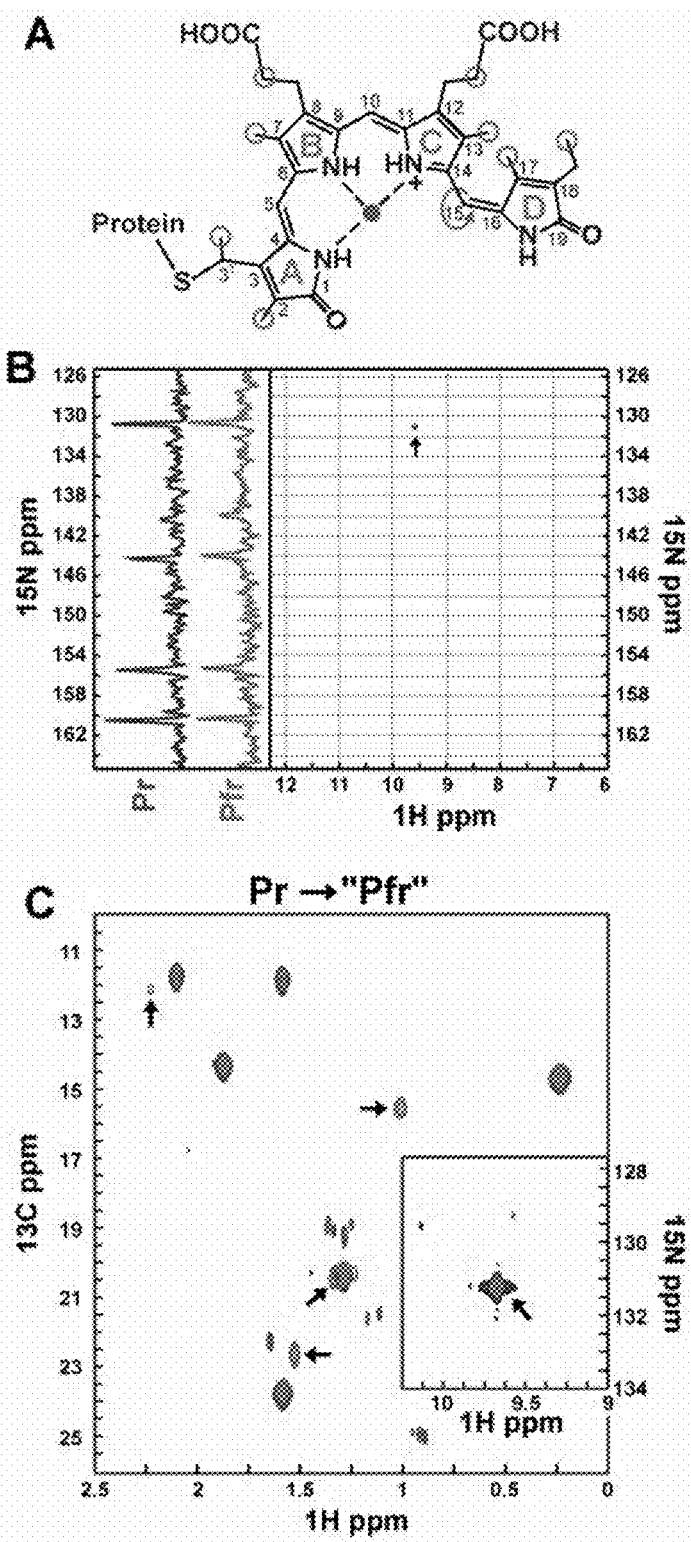
FIG. 20 illustrates the location of the PCB carbons (circled) labeled with $^{13}C$ using the heme precursor 1,2-[$^{13}C$]-ALA (A) and shows graphs of one-dimensional $^{15}N$ spectra (B) and two-dimensional $^{1}H$-$^{15}N$ and $^{1}H$-$^{13}C$ HSQC NMR spectra (C) of SyB-Cph1 (GAF) assembled with isotopically labeled $^{15}N$ and $^{13}C$ PCB.

FIG. 20 shows one-dimensional $^{15}$N spectra and two-dimensional $^{1}$H-$^{15}$N and $^{1}$H-$^{13}$C HSQC NMR spectra of SyB-Cph1(GAF) assembled with isotopically labeled $^{15}$N and $^{13}$C PCB. FIG. 20A shows the location of the PCB carbons (circled in red) labeled with $^{13}$C using the heme precursor 1,2-[$^{13}$C]-ALA. PCB is shown in the predicted ZZZsyn,syn,anti conformation for Pr. The arrow shows the predicted Z to E rotation of the C15-C16 double bond during photoconversion from Pr to Pfr. The position of the pyrrole water that is coordinated by the A-, B- and C-pyrrole ring nitrogens is shown. FIG. 20B shows one-dimensional $^{15}$N NMR spectra of [$^{15}$N]-PCB SyB-Cph1 (GAF) as Pr or following saturating red light (Pfr), and a two-dimensional $^{1}$H-$^{15}$N HSQC spectrum of the same sample in Pr. FIG. 20C shows $^{1}$H-$^{13}$C HSQC spectra of SyB-Cph1 (GAF) assembled with [$^{13}$C]-PCB isotopically-labeled at the positions shown in A or assembled with [$^{15}$N]-PCB where all nitrogens were isotopically-labeled (inset). Data collected as Pr were overlaid with those obtained during continuous irradiation with red light (Pfr). Arrows identify new peaks that appeared during red light irradiation. For a visual aid, FIG. 20A shows the predicted position of the $^{13}$C-labeled carbons incorporated into PCB upon addition of 1,2-[$^{13}$C]-ALA to the medium.

Prior one-dimensional $^{15}$N NMR analysis of Syn-Cph1 (PAS-GAF-PHY) assembled with [$^{13}$C-$^{15}$N]-PCB in vitro detected all four pyrrole ring nitrogens in the Pr conformer, whose peaks split into eight peaks upon red light irradiation, implying that all four chromophore nitrogens change their geometry/chemical environment during Pr→Pfr photoconversion. A similar one-dimensional-NMR spectrum was obtained here for the Pr conformer of SyB-Cph1 (GAF) assembled with uniformly labeled [$^{15}$N]-PCB (FIG. 20B). Four distinct peaks were evident in the $^{15}$N spectrum representing each of the four pyrrole nitrogens. That these peaks were below 180 ppm were consistent with all of these nitrogens being protonated at neutral pH. Interestingly, for Syn-Cph1 (PAS-GAF-PHY) two of these peaks overlapped, indicative of similar chemical environments, whereas in SyB-Cph1 they were more uniformly resolved, indicative of more distinct chemical environments (FIG. 20B).

Three of the four one-dimensional-$^{15}$N NMR peaks (131, 155, and 160 ppm) from SyB-Cph1 (GAF) were unaffected by red light irradiation, implying that the environments of these pyrrole nitrogens do not change upon photoconversion to Pfr (FIG. 20B). A potential decrease in signal was observed for the fourth $^{15}$N peak at 144 ppm coincident with the appearance of a new $^{15}$N peak at 142 ppm, suggesting that this pyrrole nitrogen experiences a new environment upon Pr→Pfr photoconversion. Surprisingly, two-dimensional $^{1}$H-$^{15}$N HSQC of [$^{15}$N]-PCB-labeled SyB-Cph1 (GAF) as Pr revealed only a single H—N correlation peak at 131 ppm (FIG. 20B), which did not change position or intensity upon red light exposure (FIG. 20C, inset). This failure to detect additional H—N correlation peaks implied that that the protons associated with three of the four pyrrole nitrogens readily exchange with the solvent.

To examine movements of the PCB carbons in SyB-Cph1 (GAF) 1,2-[$^{13}$C]-ALA was used as the PCB precursor to label all six methyl groups and two methylenes present in the B- and C-ring propionate side chains (FIG. 20A). Two-dimensional NMR $^{1}$H-$^{13}$C HSQC spectra with the sample as Pr detected peaks for the expected six methyl groups (FIG. 20C). However, there were no peaks for the two propionate CH$_2$ methylene groups, suggesting that they are highly mobile in the Pr conformation. The positions of the $^{1}$H-$^{13}$C peaks for the methyl groups as Pr were similar to those described by Strauss et al., 2005, Biochemistry 44: 8244-8250, for Syn-Cph1 (PAS-GAF-PHY). Taken together with similar RR spectra (FIG. 25), it appears that the Pr conformer of SyB-Cph1 has bilin geometry similar to that for Syn-Cph1 even without the PAS domain. Upon saturating red light irradiation, several new peaks appeared in the $^{1}$H-$^{13}$C HSQC spectra of [$^{13}$C]-PCB SyB-Cph1 (GAF) that can be readily seen by overlaying this spectrum with that for Pr (FIG. 20C). These new peaks likely reflect movement of several PCB methyl groups to new chemical environments during Pr→Pfr photoconversion.

Two-Dimensional-NMR Analysis of $^{15}$N-$^{13}$C-Labeled SyB-CPh1 (GAF) Reveals Global Movement in the GAF Domain During Photoconversion.

To study global movements of the GAF domain polypeptide during Pr→Pfr photoconversion, $^{15}$N and $^{13}$C double-labeled SyB-Cph1 (GAF) chromoprotein were synthesized.

Figure 21:
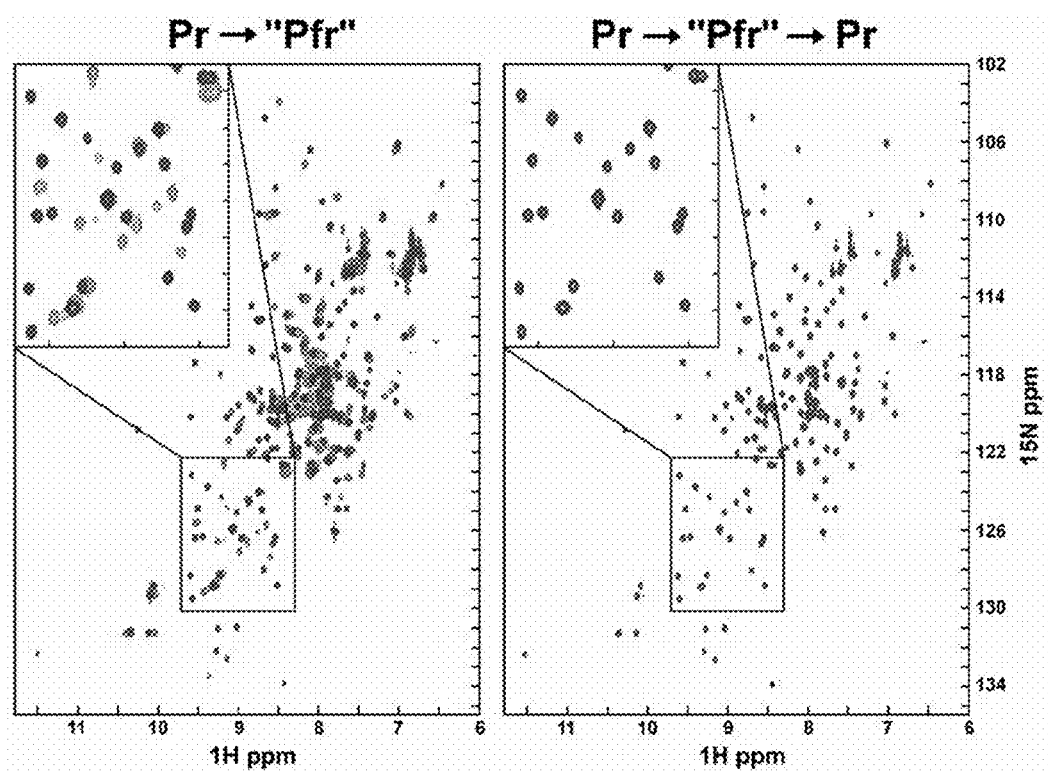
FIG. 21 shows graphs of two-dimensional $^{1}H$-$^{15}N$ HSQC NMR spectra of [$^{13}C$-$^{15}N$]-SyB-Cph1 (GAF) assembled with PCB.

FIG. 21 shows two-dimensional $^{1}$H-$^{15}$N HSQC NMR spectra of [$^{13}$C-$^{15}$N]-SyB-Cph1 (GAF) assembled with PCB. NMR data were collected with four scans over a 20 minute period with 2 mM [$^{15}$N-$^{13}$C]-SyB-Cph1 (GAF) dissolved in 7% D$_2$O 10 mM Tris-HCl (pH 8.5). Left panel, two-dimensional NMR spectrum of Pr (blue) overlaid on that obtained during continuous red light irradiation (Pfr, red). Right panel, two-dimensional NMR spectrum of Pr overlaid on that obtained for a sample exposed to saturating red light (Pfr) followed by saturating far-red light (regenerated Pr). The insets are magnifications of regions in the $^{1}$H-15N HSQC spectra that included a number of peaks that substantially change position upon Pfr formation.

Presumably due to its stability and small size (208 amino acids), this sample generated highly resolved two-dimensional $^{1}$H-15N HSQC spectra as Pr. (FIG. 21A). The number of detected $^{1}$H-15N peaks was reasonably close to the expected number generated from the predicted 208-amino-acid 6His-tagged SyB-Cph1 (GAF) chromoprotein with the addition of some observable side-chain resonances.

When the [$^{15}$N-$^{13}$C]-SyB-Cph1 (GAF) sample was photoconverted to Pfr by saturating red light and then maintained in this photoequilibrium during data collection by continuous red light irradiation, a remarkably distinct $^{1}$H-$^{15}$N HSQC spectrum was captured. When overlaid with the original Pr plot, the two-dimensional NMR Pr/Pfr spectrum not only contained the same $^{1}$H-$^{15}$N peaks observed with Pr (FIG. 21A), thus reflecting residual Pr at photoequilibrium, but also contained numerous new $^{1}$H-$^{15}$N peaks that reflected the movement of various amide groups specific to Pfr (FIG. 21A). Close inspection of the NMR data suggested that the environment of as much as 50% of the amides changed significantly during Pr to Pfr photoconversion. Moreover, when the red light-irradiated samples were converted back to Pr, either by extended darkness or by subsequent irradiation with saturating far-red light, all Pfr-associated peaks returned back to their original Pr positions (FIG. 21B). This photoreversibility demonstrated that the new peaks observed after red light irradiation were not generated by denaturation or photobleaching of the sample, but likely reflected the signature photochromicity of Phys. This measurement thus represents the first assessment of the global movements of a Phy CBD during Pr→Pfr photoconversion in solution and indicates that the conformations of the GAF domain in the Pr and Pfr conformers differ more substantially than previously anticipated.

Novel Features of SyA-Cph1 and SyB-Cph1 Enable Structural Analysis of Phys by NMR.

The structural resolution of both Pr and Pfr will be essential to fully understand how Phys function at the atomic level. While the Pr structures of two CBDs have recently been determined using x-ray crystallography (Wagner et al., 2007, J. Biol. Chem. 282: 12298-12309), those for Pfr have not yet been solved for a variety of technical reasons. Crystallization of the Pfr conformer has been challenged by substantial contamination of Pr even under saturating red light and the instability of Pfr once formed, which for most Phys will revert thermally back to Pr. Generating Pfr by irradiating diffraction quality Pr crystals with red light has also failed thus far. The crystals have either failed to photoconvert or dissolved, implying that the crystal lattice containing Pr cannot accommodate the structural rearrangements that occur during Pr→Pfr photoconversion. Exploiting naturally occurring Phys that prefer Pfr as the most stable state is an alternative for crystallizations.

Solving the solution structure of Pfr using NMR is an attractive alternative, given the ability of this approach to resolve chemical shifts generated solely from Pfr by "subtracting" the NMR spectrum generated with Pr from that obtained after saturating red light irradiation. NMR approaches work best if the size of the protein complex in solution is below 35 kDa. Unfortunately, the Phy CBDs studied to date exceed this size range, needing at least the 30-kDa PAS-GAF fragment to generate the Meta-Rc state from Pr and at least the ~60-kDa PAS-GAF-PHY fragment for full photoconversion. These sizes are further increased by dimerization, thus putting most previously described Phys outside the acceptable size range required for conventional NMR spectroscopy techniques.

The two thermostable Cphs described herein, SyA-Cph1 and SyB-Cph1, belong to a new sub-class of Phys with unique features that are particularly amenable to NMR studies. Like canonical Phys, SyA-Cph1 and SyB-Cph1 contain a GAF domain that binds the bilin, followed by a PHY domain considered essential for proper Phy photochemistry, and end with an HK domain similar to those found in many two-component signaling receptors. The GAF domains of both contain all of the strongly conserved amino acids shown to be important for bilin binding and Pr→Pfr photoconversion. SyA-Cph1 and SyB-Cph1 both have a cysteine at position 138, which like others within the Cph family appears to serve as the bilin linkage site. As expected this pair binds PCB effectively to generate red/far-red light photochromic photoreceptors. Unfortunately, given the insolubility of the full-length recombinant polypeptides, it is not yet known how Pr→Pfr photoconversion affects the phosphotransferase activity of the appended HK domain.

Conservation of the GAF domain is further supported by the analysis of site-directed mutants affecting Tyr-54 and Asp-86 in SyB-Cph1, which have been shown to hold key functional roles in other Phys. Like similar mutations in Syn-Cph1 and DrBphP, replacement of these residues does not affect bilin-binding and formation of Pr but can substantially affect photoconversion to Pfr. The D86H chromoproteins in particular are substantially blocked in Pr→Pfr photoconversion and are highly red fluorescent. The effect of the Y54H and D86H mutations contrasts those for Syn-Cph1 in which the comparable Y176His strongly fluorescent while the D207H mutant is poorly fluorescent (Fischer and Lagarias, 2004, *Proc. Natl. Acad. Sci. USA* 101: 17334-17339; Fischer et al., 2005, *Biochemistry* 44: 15203-15215).

One remarkable feature of SyA-Cph1 and SyB-Cph1 is that they belong to a previously unknown subfamily of Phys present in at least several cyanobacteria (including mesophiles) that lack the N-terminal PAS domain. Members of this family can also be distinguished from other Cphs by a strongly conserved RIT motif at the beginning of the GAF domain. While the function(s) of the PAS domain in Phy signaling are not yet clear, its presence in most Phys studied to date across a wide range of species, including bacteria, cyanobacteria, fungi and plants, has implied that it serves an essential function.

Three-dimensional structures of the CBD revealed that the PAS domain is tethered to the adjacent GAF domain by a figure-of-eight knot, created by threading the residues N-terminal to the PAS domain through a lasso loop between β9 and α7 of the GAF domain (based on the DrBphP CBD structure). The resulting anti-parallel three-helix bundle also contacts the B-ring propionate acid side chain of the bilin, thus connecting the PAS domain indirectly to the chromophore. Strikingly, even though the PAS domain is absent in this PAS-less RIT Cph subfamily, the GAF domain has retained the extra sequence that forms the lasso loop and several conserved residues within that are central to the knot core (e.g., Ile-113, Leu-127 and Arg-133 in SyB-Cph1).

In addition to the RIT subclass, other PAS-less Phys have been reported, including *Synechocystis* Cph2. The functions of Syn-Cph2 are not known but it has been suggested that it participates in blue-light sensing. Like SyA-Cph1 and SyB-Cph1, Syn-Cph2 can bind PCB covalently in vitro and become red/far-red light photochromic with Pr and Pfr absorption maxima at ~645 and 690 nm, respectively. Similarly, Syn-Cph2 also contains a second GAF domain downstream of the PHY domain; this GAF2 sequence can bind PCB when expressed alone but the resulting chromoprotein is not red/far-red photochromic. By inference, it is possible that SyA-Cph1 and SyB-Cph1 can incorporate two bilin groups simultaneously.

Regardless of its function, it is clear that the PAS domain is not essential for photochromicity. Both SyA-Cph1 and SyB-Cph1 constructions containing only the 200-amino acid GAF domain covalently assemble with PCB to generate Pr with absorption spectra close to those obtained with PAS-containing fragments from *Synechocystis* Cph1. The only substantive difference was a blue shift of the Pr absorption maximum of the SyB-Cph1 constructions (630 nm) relative to Syn-Cph1 constructions (659 nm). In contrast to several other Phys (Karniol et al., 2005, *Biochem. J.* 392: 103-116; Mroginski et al., 2007, *Acc. Chem. Res.* 40: 258-266), SyB-Cph1 (and likely SyA-Cph1) also appears less dependent on the PHY domain for full photoconversion to Pfr. Absorption, RR, and NMR spectroscopy indicate that most of the SyB-Cph1 (GAF) truncation photoconverts to the protonated Pfr-type state upon red light irradiation with only slight modifications of its spectral properties (for example, 15-nm blue shift of Pfr absorption maximum). Combined with its monomeric size, the SyB-Cph1 (GAF) fragment is well within the acceptable size range for NMR analysis of Pfr.

Another important feature of these Phys is their remarkable heat stability, being capable of withstanding temperatures above 70° C. NMR data collection was facilitated by the ability to sterilize the recombinant photoreceptors against contaminating *E. coli* proteases simply by heating the preparations to 65° C. before use. These sterilized preparations were surprisingly stable both in terms of solubility and photochemistry, and easily survived long-term three-dimensional data collection. This thermostability was also reflected by its Pr→Pfr photoconversion and Pfr→Pr dark reversion kinetics, which are both faster at high temperatures. Taken together, these Phys might rapidly interconvert between Pr and Pfr when the host *Synechococcus* OS-A and OS-B' organisms are grown in their natural daylight environment.

SyB-Cph1(GAF) can be easily labeled isotopically for NMR analyses. By either introducing $^{15}$N and/or $^{13}$C isotopes into amino acids or feeding the $^{15}$N or $^{13}$C-labeled heme-precursor ALA to SyB-Cph1 (GAF)-expressing cells, it was possible to independently introduce isotopes into the polypeptide and PCB moieties, respectively. The resulting preparations generated two-dimensional NMR spectra with sufficient clarity to discern peaks associated with Pfr from those associated with Pr.

NMR Analysis of the SvB-Cph1 Chromophore PCB.

Initial NMR analyses confirmed the utility of SyB-Cph1 (GAF) preparations for structural studies. One-dimensional NMR spectra of [$^{15}$N]-PCB labeled preparations in the Pr state detected all four of the pyrrole-ring nitrogens (FIG. 20B). Surprisingly, only one of these nitrogens (144 ppm) apparently changed its chemical environment after red light irradiation. Such spectra not only confirmed RR data that PCB is protonated (cationic) as Pfr for this GAF-domain only fragment but implied that the environment/position of three of the four pyrrole N—H groups change little during Pr→Pfr photoconversion. $^1$H-$^{15}$N HSQC spectra both before and after red light irradiation detected only a single $^1$H-13N chemical shift at 131 ppm, further suggesting that one of the four bound protons is tightly held and exchanges slowly with the solvent whereas the remaining three protons readily mix with the surrounding water.

Prior RR, ultrafast and mid-infrared, and NMR spectroscopic studies with a variety of Phys including *Synechocystis* Cph1 have suggested that the B and C pyrrole rings move little during photoconversion with most of the movement involving rings A and D. Contrary to the expected large movements of the D ring following the Z to E double bond isomerization of the C15-C16 methine linker, it has been proposed further that the A ring undergoes the more pronounced conformational changes, potentially via a Zsyn to Zanti rotation around the $C_5$-$C_6$ methine bridge between rings A and B. The $^{15}$N and $^{13}$C NMR data with SyB-Cph1 (GAF) are consistent with these interpretations. The high-resolution crystal structure of DrBphP assembled with BV showed that the pyrrole nitrogens present in the A-C rings are held in a ZZsyn,syn configuration as Pr and hydrogen bond with the centrally positioned pyrrole water (see FIG. 20A), whereas the D-ring N—H group is contorted 44° out-of-plane in a Zanti configuration and held in place by a second hydrogen bond network involving His-290 and water. Assuming this configuration holds true for SyB-Cph1 assembled with PCB, and not wanting to be bound by the following theory, it is possible that the exchangeable protons (detected at 160, 156, and 144 ppm) are all bound to the A-C rings. This assignment is consistent with the RR data which unambiguously show that the pyrrole rings B and C are protonated with the protons rapidly exchanging with the solvent. The free exchange of the ring A-C protons with the solvent is also plausible in view of the deprotonation/protonation cycle of the chromophore during Pr→Pfr photoconversion.

Only one of the exchangeable protons in SyB-Cph1(GAF) changed environment/location upon photoconversion to Pfr. It appeared in the one-dimensional $^{15}$N NMR spectra as a peak at 144 ppm, which appeared to diminish in height during red-light irradiation concomitant with the appearance of a new peak at 142 ppm. Assuming that the B and C rings are in similar chemical environments and are more rigidly held via their propionate side chains, then the moving pyrrole ring is best assigned to the A ring. In support, Rohmer et al., 2006, *J. Phys. Chem. B.* 110: 20580-20585, tentatively assigned a similar $^{15}$N chemical shift, which moved from 146.8 ppm to 142.8 ppm during photoconversion, to the A-ring nitrogen of *Synechocystis* Cph1 (PAS-GAF-PHY) fragment. The remaining slowly exchangeable proton nitrogen in SyB-Cph1 (GAF), which had a cross peak at 131 ppm (15N chemical shift), would then be assigned by default to the D-ring pyrrole N—H group. The absence of additional H—N cross-peaks in the $^1$H-$^{15}$N HSQC Pr/Pfr spectra overlay further implied that the amide of this ring does not change upon photoconversion (see FIG. 20C, inset).

Examination of SyB-Cph1(GAF) bearing [$^{13}$C]-PCB by $^1$H-$^{13}$C HSQC detected all six predicted methyl groups, and revealed that four of the six experience a significantly different environment after red light irradiation (FIG. 20C). Such movements closely parallel those obtained by Strauss et al., 2005, *Biochemistry* 44: 8244-8250, who showed that all but one of the six methyl groups acquire alternate peaks with red light saturation. The peak of one methyl in particular (15.5 ppm) for SyB-Cph1 (GAF) moved a considerable distance during photoconversion, implying that it encounters a radically different chemical environment as Pfr.

SyB-Cph1 (GAF) is Amenable to $^1$H-$^{15}$N-$^{13}$C Three-Dimensional NMR.

While several studies have demonstrated that various regions of the Phy polypeptide move during Pr→Pfr phototransformation, their exact motions remain to be determined. The small size and thermostability of the SyB-Cph1 (GAF) truncation coupled with its ability to effectively complete the Pr→Pfr photocycle strongly suggests that this species may help resolve movements in the GAF domain by NMR approaches. Toward this objective, SyB-Cph1 (GAF) generates excellent three-dimensional NMR spectra using preparations incorporating $^{15}$N and $^{13}$C into the chromophore or polypeptide. Overlays of either $^1$H-$^{15}$N HSQC or $^1$H-$^{13}$C HSQC spectra from [$^{15}$N-$^{13}$C]-SyB-Cph1 (GAF) samples obtained before and during continuous saturating red light irradiations identified numerous reversible peaks that move substantially (FIG. 21). These movements presumably reflect changing chemical environments of specific amino acid-associated amides during Pr→Pfr photoconversion. Moreover, many of these peaks remained well defined as Pfr, indicating that the corresponding amides now occupy new and stable environments in this conformer. The large number of unique Pfr peaks implies that the GAF domain by itself undergoes a more robust conformational change during phototransformation than previously appreciated.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of genetics, molecular biology, and biochemistry, are within the scope of this invention. All publications, patents, and patent applications cited herein are incorporated by reference in their entirety for all purposes.

SUMMARY OF SEQUENCE LISTINGS

SEQ ID NO:1 is the amino acid sequence of the chromophore-binding domain of bacterial phytochrome isolated from *Deinococcus radiodurans* (DrCBD).

SEQ ID NO:2 is the amino acid sequence of the GAF domain of the *Deinococcus radiodurans* phytochrome.

SEQ ID NO:3 is the amino acid sequence of the full-length SyA-Cph1 protein of the bacterium *Synechococcus* sp. OS Type A.

SEQ ID NO:4 is the amino acid sequence of the GAF domain of the bacterium *Synechococcus* sp. OS Type A.

SEQ ID NO:5 is the amino acid sequence of the full-length SyB-Cph1 protein of the bacterium *Synechococcus* sp. OS Type B'.

SEQ ID NO:6 is the amino acid sequence of the GAF and PHY domains of the bacterium *Synechococcus* sp. OS Type B'.

SEQ ID NO:7 is the amino acid sequence of the GAF domain of the bacterium *Synechococcus* sp. OS Type B'.

SEQ ID NO:8 is the amino acid sequence of an attenuated GAF domain from *Synechococcus* OS B'.

SEQ ID NO:9 is the sequence of an oligonucleotide primer used to construct the Phy truncation Syn-Cph1 (PAS-GAF): primer 1 used in reaction 1.

SEQ ID NO:10 is the sequence of an oligonucleotide primer used to construct the Phy truncation Syn-Cph1 (PAS-GAF): primer 2 used in reaction 1.

SEQ ID NO:11 is the sequence of an oligonucleotide primer used to construct the Phy truncation Syn-Cph1 (PAS-GAF): primer 1 used in reaction 2.

SEQ ID NO:12 is the sequence of an oligonucleotide primer used to construct the Phy truncation Syn-Cph1 (PAS-GAF): primer 2 used in reaction 2.

SEQ ID NO:13 is the sequence of an oligonucleotide primer used to construct the Phy truncation SyA-Cph1 (GAF): primer 1 used in reaction 1.

SEQ ID NO:14 is the sequence of an oligonucleotide primer used to construct the Phy truncation SyA-Cph1 (GAF): primer 2 used in reaction 1.

SEQ ID NO:15 is the sequence of an oligonucleotide primer used to construct the Phy truncation SyA-Cph1 (GAF): primer 1 used in reaction 2.

SEQ ID NO:16 is the sequence of an oligonucleotide primer used to construct the Phy truncation SyA-Cph1 (GAF): primer 2 used in reaction 2.

SEQ ID NO:17 is the sequence of an oligonucleotide primer used to construct the Phy truncation SyB-Cph1 (GAF): primer 1 used in reaction 1.

SEQ ID NO:18 is the sequence of an oligonucleotide primer used to construct the Phy truncation SyB-Cph1 (GAF): primer 2 used in reaction 1.

SEQ ID NO:19 is the sequence of an oligonucleotide primer used to construct the Phy truncation SyB-Cph1 (GAF): primer 1 used in reaction 2.

SEQ ID NO:20 is the sequence of an oligonucleotide primer used to construct the Phy truncation SyB-Cph1 (GAF): primer 2 used in reaction 2.

SEQ ID NO:21 is the sequence of an oligonucleotide primer used to construct the Phy truncation SyA-Cph1 (GAF-PHY): primer 1 used in reaction 1.

SEQ ID NO:22 is the sequence of an oligonucleotide primer used to construct the Phy truncation SyA-Cph1 (GAF-PHY): primer 2 used in reaction 1.

SEQ ID NO:23 is the sequence of an oligonucleotide primer used to construct the Phy truncation SyA-Cph1 (GAF-PHY): primer 1 used in reaction 2.

SEQ ID NO:24 is the sequence of an oligonucleotide primer used to construct the Phy truncation SyA-Cph1 (GAF-PHY): primer 2 used in reaction 2.

SEQ ID NO:25 is the sequence of an oligonucleotide primer used to construct the Phy truncation SyB-Cph1 (GAF-PHY): primer 1 used in reaction 1.

SEQ ID NO:26 is the sequence of an oligonucleotide primer used to construct the Phy truncation SyB-Cph1 (GAF-PHY): primer 2 used in reaction 1.

SEQ ID NO:27 is the sequence of an oligonucleotide primer used to construct the Phy truncation SyB-Cph1 (GAF-PHY): primer 1 used in reaction 2.

SEQ ID NO:28 is the sequence of an oligonucleotide primer used to construct the Phy truncation SyB-Cph1 (GAF-PHY): primer 2 used in reaction 2.

SEQ ID NO:29 is the sequence of oligonucleotide primer 1 used to construct the Phy truncation Syn-Cph1 D207H; 19C is a mutagenic nucleotide.

SEQ ID NO:30 is the sequence of oligonucleotide primer 2 used to construct the Phy truncation Syn-Cph1 D207H; 18G is a mutagenic nucleotide.

SEQ ID NO:31 is the sequence of oligonucleotide primer 1 used to construct the Phy truncation Syn-Cph1 Y176H; 21C is a mutagenic nucleotide.

SEQ ID NO:32 is the sequence of oligonucleotide primer 2 used to construct the Phy truncation Syn-Cph1 Y176H; 21 G is a mutagenic nucleotide.

SEQ ID NO:33 is the sequence of oligonucleotide primer 1 used to construct the Phy truncation Syn-Cph1D86H; 19C is a mutagenic nucleotide.

SEQ ID NO:34 is the sequence of oligonucleotide primer 2 used to construct the Phy truncation Syn-Cph1D86H; 18G is a mutagenic nucleotide.

SEQ ID NO:35 is the sequence of oligonucleotide primer 1 used to construct the Phy truncation Syn-Cph1 Y54H; 18C is a mutagenic nucleotide.

SEQ ID NO:36 is the sequence of oligonucleotide primer 2 used to construct the Phy truncation Syn-Cph1 Y54H; 16G is a mutagenic nucleotide.

SEQ ID NO:37 is the sequence of oligonucleotide primer 1 used to construct the Phy truncation Syn-Cph1 C138A; 22G and 23C are mutagenic nucleotides.

SEQ ID NO:38 is the sequence of oligonucleotide primer 2 used to construct the Phy truncation Syn-Cph1C138A.

SEQ ID NO:39 is the sequence of one oligonucleotide primer used to replace codons with those encoding a 6His tag.

SEQ ID NO:40 is the sequence of another oligonucleotide primer used to replace codons with those encoding a 6His tag.

SEQ ID NO:41 is the sequence of one oligonucleotide primer used to generate a PAS-GAF-PHY truncation of DrB-phP.

SEQ ID NO:42 is the sequence of another oligonucleotide primer used to generate a PAS-GAF-PHY truncation of DrB-phP.

SEQ ID NO:43 is a "PAS-less" phytochrome consensus amino acid sequence.

SEQ ID NO:44 is a DUF309 domain consensus amino acid sequence.

SEQ ID NO:45 is a DUF309 domain consensus amino acid sequence.

SEQ ID NO: 46 is the polynucleotide coding sequence of the chromophore binding domain of bacterial phytochrome isolated from *Deinococcus radiodurans* (DrCBD).

SEQ ID NO: 47 is the polynucleotide coding sequence of the full-length SyACphl protein of the bacterium *Synechococcus* sp. OS Type A.

SEQ ID NO: 48 is the polynucleotide coding sequence of the full-length SyBCphl protein of the bacterium *Synechococcus* sp. OS Type B'.

SEQUENCE LISTING

```
<160> NUMBER OF SEQ ID NOS: 48

<210> SEQ ID NO 1
<211> LENGTH: 342
<212> TYPE: PRT
<213> ORGANISM: Deinococcus radiodurans

<400> SEQUENCE: 1
```

```
Met Ala Leu Ser Met Thr Gly Gln Gln Met Gly Arg Gly Ser Met
1               5                   10                  15

Ser Arg Asp Pro Leu Pro Phe Phe Pro Pro Leu Tyr Leu Gly Gly Pro
            20                  25                  30

Glu Ile Thr Thr Glu Asn Cys Glu Arg Glu Pro Ile His Ile Pro Gly
                35                  40                  45

Ser Ile Gln Pro His Gly Ala Leu Leu Thr Ala Asp Gly His Ser Gly
        50                  55                  60

Glu Val Leu Gln Met Ser Leu Asn Ala Ala Thr Phe Leu Gly Gln Glu
65                  70                  75                  80

Pro Thr Val Leu Arg Gly Gln Thr Leu Ala Ala Leu Leu Pro Glu Gln
                85                  90                  95

Trp Pro Ala Leu Gln Ala Ala Leu Pro Pro Gly Cys Pro Asp Ala Leu
            100                 105                 110

Gln Tyr Arg Ala Thr Leu Asp Trp Pro Ala Ala Gly His Leu Ser Leu
        115                 120                 125

Thr Val His Arg Val Gly Glu Leu Leu Ile Leu Glu Phe Glu Pro Thr
    130                 135                 140

Glu Ala Trp Asp Ser Thr Gly Pro His Ala Leu Arg Asn Ala Met Phe
145                 150                 155                 160

Ala Leu Glu Ser Ala Pro Asn Leu Arg Ala Leu Ala Glu Val Ala Thr
                165                 170                 175

Gln Thr Val Arg Glu Leu Thr Gly Phe Asp Arg Val Met Leu Tyr Lys
            180                 185                 190

Phe Ala Pro Asp Ala Thr Gly Glu Val Ile Ala Glu Ala Arg Arg Glu
        195                 200                 205

Gly Leu His Ala Phe Leu Gly His Arg Phe Pro Ala Ser Asp Ile Pro
    210                 215                 220

Ala Gln Ala Arg Ala Leu Tyr Thr Arg His Leu Leu Arg Leu Thr Ala
225                 230                 235                 240

Asp Thr Arg Ala Ala Ala Val Pro Leu Asp Pro Val Leu Asn Pro Gln
                245                 250                 255

Thr Asn Ala Pro Thr Pro Leu Gly Gly Ala Val Leu Arg Ala Thr Ser
            260                 265                 270

Pro Met His Met Gln Tyr Leu Arg Asn Met Gly Val Gly Ser Ser Leu
        275                 280                 285

Ser Val Ser Val Val Gly Gly Gln Leu Trp Gly Leu Ile Ala Cys
    290                 295                 300

His His Gln Thr Pro Tyr Val Leu Pro Pro Asp Leu Arg Thr Thr Leu
305                 310                 315                 320

Glu Ser Leu Gly Arg Leu Leu Ser Leu Gln Val Gln Val Lys Glu Ala
                325                 330                 335

His His His His His His
            340

<210> SEQ ID NO 2
<211> LENGTH: 165
<212> TYPE: PRT
<213> ORGANISM: Deinococcus radiodurans
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (108)..(108)
```

-continued

```
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 2

Asn Leu Arg Ala Leu Ala Glu Val Ala Thr Gln Thr Val Arg Glu Leu
1               5                   10                  15

Thr Gly Phe Asp Arg Val Xaa Leu Tyr Lys Phe Ala Pro Asp Ala Thr
            20                  25                  30

Gly Glu Val Ile Ala Glu Ala Arg Arg Glu Gly Leu His Ala Phe Leu
        35                  40                  45

Gly His Arg Phe Pro Ala Ser Asp Ile Pro Ala Gln Ala Arg Ala Leu
    50                  55                  60

Tyr Thr Arg His Leu Leu Arg Leu Thr Ala Asp Thr Arg Ala Ala Ala
65                  70                  75                  80

Val Pro Leu Asp Pro Val Leu Asn Thr Gln Thr Asn Ala Pro Thr Pro
                85                  90                  95

Leu Gly Gly Ala Val Leu Arg Ala Thr Ser Pro Xaa His Xaa Gln Tyr
            100                 105                 110

Leu Arg Asn Xaa Gly Val Gly Ser Leu Ser Val Ser Val Val Val
        115                 120                 125

Gly Gly Gln Leu Trp Gly Leu Ile Ala Cys His His Gln Thr Pro Tyr
    130                 135                 140

Val Leu Pro Pro Asp Leu Arg Thr Thr Leu Glu Tyr Leu Gly Arg Leu
145                 150                 155                 160

Leu Ser Leu Gln Val
                165

<210> SEQ ID NO 3
<211> LENGTH: 835
<212> TYPE: PRT
<213> ORGANISM: Synechococcus OS A'

<400> SEQUENCE: 3

Met Glu Thr Leu Ala Pro Ala Ala Cys Ala Ser Arg Asp Val Leu Ile
1               5                   10                  15

Asn Arg Ile Thr His Gln Ile Arg Gln Ser Leu Glu Leu Asp Gln Ile
            20                  25                  30

Leu Arg Ala Thr Val Glu Glu Val Arg Ala Phe Leu Gly Thr Asp Arg
        35                  40                  45

Val Lys Val Tyr Arg Phe Asp Pro Glu Gly His Gly Thr Val Val Ala
    50                  55                  60

Glu Ala Arg Gln Ala Glu Arg Leu Pro Ser Leu Leu Gly Leu Ser Phe
65                  70                  75                  80

Pro Ala Gly Asp Ile Pro Glu Glu Ala Arg Gln Leu Phe Arg Leu Ala
                85                  90                  95

Gln Val Arg Val Ile Val Asp Val Glu Ala Gln Thr Arg Phe Leu Ser
            100                 105                 110

Gln Pro Glu Ser Leu Gly Arg Phe Ala Gln Ala Arg Pro Leu Pro Leu
        115                 120                 125

Gly Glu Val Pro Gln Arg Leu Val Asp Pro Cys His Ala His Tyr Leu
    130                 135                 140
```

```
Lys Cys Met Gly Val Ala Ser Ser Leu Val Pro Leu Leu His His
145                 150                 155                 160

Gln Gln Leu Trp Gly Leu Leu Val Ser His His Ala Glu Pro Arg Ser
                165                 170                 175

Tyr Ser Ala Glu Glu Leu Gln Val Val Gln Leu Val Ala Asp Gln Val
            180                 185                 190

Ser Ile Ala Ile Ala Gln Ala Glu Leu Leu Glu Gln Ala Arg Gln Lys
            195                 200                 205

Ala Gln Gln Glu Arg Leu Ile Asn Gln Ile Ala Ala Leu Val Tyr Ser
210                 215                 220

Pro Leu His Pro Glu Thr Thr Leu Thr Val Leu Glu Gln Leu Thr
225                 230                 235                 240

Ala Gly Leu Gln Gly Ile Gly Ala Arg Leu Arg Ile Arg Phe Leu Gly
                245                 250                 255

Leu Asp Thr Leu Cys His His Gly Ile Gln Pro Pro Ala Gly Tyr Asp
            260                 265                 270

Ala Trp Leu Gln Glu Gln Val Gly Arg Pro Lys Thr Ala Gly Asn Gly
            275                 280                 285

Val Lys Thr Trp Ser Leu Ser Gln Leu Glu Lys Trp Pro Glu Leu Gln
            290                 295                 300

Ala Gln Leu Gln Gln Thr Pro Ile Arg Gly Leu Leu Ala Val Pro Leu
305                 310                 315                 320

Val Trp Asn Glu Gln Leu Val Gly Trp Leu Ser Val Phe Arg Gly Ala
                325                 330                 335

Leu Cys Gln Glu Thr His Trp Ala Gly Tyr Arg Trp Pro Ala Gln Gly
            340                 345                 350

Glu Gly Gly Glu Asp Pro Arg Gln Glu Leu Pro Leu Ile Ser Phe Ala
            355                 360                 365

Ala Trp Arg Glu Leu Lys Val Asp Glu Pro Lys Ala Trp Ser Ala Ala
370                 375                 380

Glu Leu Glu Leu Val Gly Arg Ala Ala Val His Leu Ala Leu Ser Ile
385                 390                 395                 400

Ala Gln Asn Gln Leu Tyr Arg Gln Leu Gln Asp Leu Asn Ala Arg Leu
                405                 410                 415

Glu His Glu Val Glu Glu Arg Thr Ala Ala Leu Gln Arg Ser Leu Ala
            420                 425                 430

Met Asp Ala Leu Leu Gln Arg Val Thr Asp Gln Val Arg Ser Ser Leu
            435                 440                 445

Asp Glu Ala Gln Ile Leu Arg Ala Val Val Gln Glu Leu Ala Leu Gly
            450                 455                 460

Leu Pro Ile Gln Gly Cys Asp Leu Cys Leu Tyr Glu Gly Ala Ala Gly
465                 470                 475                 480

Gln Ala Thr Val Arg Tyr Glu Tyr Thr Ala Ala Leu Pro Pro Ala Gly
                485                 490                 495

Gly Ile Thr Leu Thr Leu Ala Asp Tyr Pro Asp Leu Tyr Arg Gln Leu
            500                 505                 510

Gln Arg Gly Gln Ala Ala Gln Leu Cys His Leu Pro Gly Gln Ser Trp
            515                 520                 525

Ile Pro Arg Arg Glu Gly Leu Thr Leu Leu Val Cys Pro Leu Arg Asp
            530                 535                 540

Asp Gln Gly Ala Leu Gly Asp Leu Trp Leu Ala Lys Ala Ala Ala Glu
545                 550                 555                 560
```

```
Cys Phe Asp Thr Leu Glu Met Gln Val Val Gln Val Ala Asp His
                565                 570                 575

Cys Ala Ile Ala Ile Arg Gln Ala Arg Leu Tyr Gln Ala Ser Val Gln
            580                 585                 590

Gln Ile Ser Glu Leu Glu Arg Leu Asn Arg Leu Lys Asp Asp Phe Leu
        595                 600                 605

Ser Thr Val Ser His Glu Leu Arg Thr Pro Ile Thr Asn Met Lys Met
    610                 615                 620

Ala Ile Gln Leu Leu Lys Met Ala Arg Thr Pro Gln Lys Arg Glu Gln
625                 630                 635                 640

Tyr Leu Gln Ile Leu Glu Gln Glu Cys Glu Arg Glu Ala Glu Leu Ile
                645                 650                 655

Asn Asp Leu Leu Asp Leu Gln Arg Leu Glu Gln Gly Ser Lys Pro Leu
            660                 665                 670

His Leu Glu Glu Val Ser Leu Ala Ala Trp Leu Pro Thr Val Leu Gln
        675                 680                 685

Pro Phe Val Gln Arg Ala Glu Ala Asn Gln Gln Leu Gln Trp Gln
    690                 695                 700

Ile Asp Pro Lys Val Gly Lys Val Val Thr Asp Gln Ala Ala Leu Thr
705                 710                 715                 720

Arg Val Val Gln Glu Leu Val Asn Asn Ala Cys Lys Tyr Thr Pro Pro
                725                 730                 735

Gln His Arg Ile Thr Val Thr Ala Arg Arg Leu Ser Pro Glu Gln Val
            740                 745                 750

Gln Ile Arg Val Val Asn Glu Gly Val Glu Ile Pro Arg Ser Glu Trp
        755                 760                 765

Glu Arg Ile Phe Glu Lys Phe Tyr Arg Ile Pro Ser Gly Asp Pro Trp
    770                 775                 780

Lys Arg Gly Gly Thr Gly Leu Gly Leu Ala Leu Val Lys Gln Trp Met
785                 790                 795                 800

Gln Arg Leu Gly Gly Cys Val Ser Ile Glu Ser Gly Gln Gly Lys Thr
                805                 810                 815

Cys Phe Thr Leu Val Leu Pro Gln Gly Ser Leu Pro Gly Gln Thr Ser
            820                 825                 830

Cys Thr Ala
        835

<210> SEQ ID NO 4
<211> LENGTH: 178
<212> TYPE: PRT
<213> ORGANISM: Synechococcus OS A'

<400> SEQUENCE: 4

Leu Asp Gln Ile Leu Arg Ala Thr Val Glu Glu Val Arg Ala Phe Leu
1               5                   10                  15

Gly Thr Asp Arg Val Lys Val Tyr Arg Phe Asp Pro Glu Gly His Gly
            20                  25                  30

Thr Val Val Ala Glu Ala Arg Gln Ala Glu Arg Leu Pro Ser Leu Leu
        35                  40                  45

Gly Leu Ser Phe Pro Ala Gly Asp Ile Pro Glu Glu Ala Arg Gln Leu
    50                  55                  60

Phe Arg Leu Ala Gln Val Arg Val Ile Val Asp Val Glu Ala Gln Thr
65                  70                  75                  80

Arg Phe Leu Ser Gln Pro Glu Ser Leu Gly Arg Phe Ala Gln Ala Arg
                85                  90                  95
```

```
Pro Leu Pro Leu Gly Glu Val Pro Gln Arg Leu Val Asp Pro Cys His
            100                 105                 110

Ala His Tyr Leu Lys Cys Met Gly Val Ala Ser Ser Leu Val Val Pro
        115                 120                 125

Leu Leu His His Gln Gln Leu Trp Gly Leu Leu Val Ser His His Ala
    130                 135                 140

Glu Pro Arg Ser Tyr Ser Ala Glu Glu Leu Gln Val Val Gln Leu Val
145                 150                 155                 160

Ala Asp Gln Val Ser Ile Ala Ile Ala Gln Ala Glu Leu Leu Glu Gln
                165                 170                 175

Ala Arg

<210> SEQ ID NO 5
<211> LENGTH: 834
<212> TYPE: PRT
<213> ORGANISM: Synechococcus OS B'

<400> SEQUENCE: 5

Met Asp Thr Glu Thr Trp Ala Ala Ala Arg Pro Ser Arg Asp Ala
1               5                   10                  15

Leu Ile Asn Arg Ile Thr His Gln Ile Arg Gln Ser Leu Glu Leu Asp
                20                  25                  30

Gln Ile Leu Arg Ala Thr Val Glu Val Arg Ala Phe Leu Gly Thr
            35                  40                  45

Asp Arg Val Lys Val Tyr Arg Phe Asp Pro Glu Gly His Gly Thr Val
        50                  55                  60

Val Ala Glu Ala Arg Gly Gly Glu Arg Leu Pro Ser Leu Leu Gly Leu
65                  70                  75                  80

Thr Phe Pro Ala Gly Asp Ile Pro Glu Glu Ala Arg Arg Leu Phe Arg
                85                  90                  95

Leu Ala Gln Val Arg Val Ile Val Asp Val Glu Ala Gln Ser Arg Ser
            100                 105                 110

Ile Ser Gln Pro Glu Ser Trp Gly Leu Ser Ala Arg Val Pro Leu Gly
        115                 120                 125

Glu Pro Leu Gln Arg Pro Val Asp Pro Cys His Val His Tyr Leu Lys
    130                 135                 140

Ser Met Gly Val Ala Ser Ser Leu Val Val Pro Leu Met His His Gln
145                 150                 155                 160

Glu Leu Trp Gly Leu Leu Val Ser His His Ala Glu Pro Arg Pro Tyr
                165                 170                 175

Ser Gln Glu Glu Leu Gln Val Val Gln Leu Leu Ala Asp Gln Val Ser
            180                 185                 190

Ile Ala Ile Ala Gln Ala Glu Leu Glu Gln Ala Arg Gln Lys Ala
        195                 200                 205

Gln Gln Glu Arg Leu Ile Asn Gln Leu Ala Ala Leu Val Tyr Ser Pro
    210                 215                 220

Leu His Pro Glu Thr Thr Leu Thr Thr Val Leu Glu Gln Leu Ala Ala
225                 230                 235                 240

Gly Leu Gln Gly Ile Gly Ala Arg Leu Arg Ile His Phe Met Gly Ala
                245                 250                 255

Asp Thr Leu Cys Cys His Gly Val Gln Pro Pro Ala Ser Tyr Asp Thr
            260                 265                 270

Trp Leu Gln Glu Gln Leu Gly Arg Ala Gly Gly Ala Gly Gly Trp Val
        275                 280                 285
```

-continued

```
Lys Met Trp Ser Leu Ser His Leu Glu Lys Trp Pro Glu Leu Gln Glu
290                 295                 300

Gln Met Lys Gln Thr Pro Ile Arg Gly Leu Leu Val Ala Gln Leu Ala
305                 310                 315                 320

Trp Asn Asp Gln Pro Val Gly Trp Leu Ser Val Phe Arg Gly Ala Val
                325                 330                 335

Tyr Gln Glu Thr His Trp Ala Gly Tyr Arg Trp Phe Thr Gln Gly Asp
                340                 345                 350

Pro Arg Gln Glu Leu Pro Leu Ile Ser Phe Ala Ala Trp Arg Glu Leu
                355                 360                 365

Lys Ile Asp Glu Pro Lys Ala Trp Ser Ala Ala Glu Gln Glu Leu Met
370                 375                 380

Ser Arg Val Gly Val His Leu Ala Leu Ser Ile Thr Gln Asn Gln Leu
385                 390                 395                 400

Tyr Arg Gln Leu Gln Thr Leu Asn Ala Arg Leu Glu Gln Glu Val Gln
                405                 410                 415

Glu Arg Thr Ala Ala Leu Gln Arg Ser Leu Ala Met Asp Ala Leu Leu
                420                 425                 430

Gln Arg Val Thr Asp Gln Val Arg Ser Ser Leu Glu Glu Ala Gln Ile
                435                 440                 445

Leu Arg Ala Val Val Gln Glu Leu Ala Leu Gly Leu Pro Ile Gln Gly
450                 455                 460

Cys Asp Leu Cys Leu Tyr Asp Trp Ala Ser Gly Gln Ala Thr Val Arg
465                 470                 475                 480

Tyr Glu Tyr Thr Ser Ala Leu Pro Pro Ala Gly Ile Thr Leu Thr
                485                 490                 495

Leu Ala Asp Tyr Pro Asp Leu Tyr Arg His Leu Gln Gly Gly Gln Ala
                500                 505                 510

Val Gln Phe Cys His Leu Pro Gly Gln Gly Trp Ile Pro Arg Arg Glu
                515                 520                 525

Gly Leu Thr Leu Leu Val Cys Pro Leu Arg Asp Asp Gln Gly Val Leu
530                 535                 540

Gly Asp Leu Trp Leu Ala Lys Pro Ala Ala Lys Cys Phe Asp Glu Leu
545                 550                 555                 560

Glu Val Gln Val Val Gln Gln Val Ala Asp His Cys Ala Ile Ala Ile
                565                 570                 575

Arg Gln Ala Arg Leu Tyr Gln Ala Ser Val Gln Gln Ile Gly Glu Leu
                580                 585                 590

Glu Arg Leu Asn Arg Leu Lys Asp Asp Phe Leu Ser Thr Val Ser His
                595                 600                 605

Glu Leu Arg Thr Pro Ile Thr Asn Met Arg Met Ala Ile Gln Leu Leu
610                 615                 620

Lys Thr Ala Arg Ala Pro Gln Lys Arg Glu Gln Tyr Leu Lys Ile Leu
625                 630                 635                 640

Glu Gln Glu Cys Glu Arg Glu Ala Glu Leu Val Asn Asp Leu Leu Asp
                645                 650                 655

Leu Gln Arg Leu Glu Gln Gly Ser Lys Thr Leu His Leu Glu Glu Val
                660                 665                 670

Pro Leu Ala Thr Trp Leu Pro Ser Val Leu Glu Pro Phe Leu Gln Arg
                675                 680                 685

Ala Gln Val Asn Gln Gln Arg Leu Gln Trp Gln Ile Ala Pro Asn Val
690                 695                 700
```

```
Gly Lys Val Leu Thr Asp Gln Gly Gly Leu Glu Arg Val Val Gln Glu
705                 710                 715                 720

Leu Val Asn Asn Ala Cys Lys Tyr Thr Pro Pro Gly Cys Ser Ile Trp
                725                 730                 735

Val Thr Ala Gln Arg Pro Gly Pro Gln Gln Val Glu Ile Arg Val Ile
            740                 745                 750

Asn Glu Gly Val Glu Ile Ser Pro Ala Glu Gln Glu Arg Ile Phe Glu
        755                 760                 765

Lys Phe Tyr Arg Ile Pro Ser Gly Asp Pro Trp Lys Arg Gly Gly Thr
    770                 775                 780

Gly Leu Gly Leu Ala Leu Val Lys Gln Trp Met Gln Arg Leu Gly Gly
785                 790                 795                 800

Ser Val Ser Val Glu Ser Ser Gln Gly Lys Thr Cys Phe Thr Leu Val
                805                 810                 815

Leu Pro Gln Gly Ser Leu Pro Val Gln Thr Ser Pro Leu Ala His Asn
            820                 825                 830

Cys Ala

<210> SEQ ID NO 6
<211> LENGTH: 421
<212> TYPE: PRT
<213> ORGANISM: Synechococcus OS B'

<400> SEQUENCE: 6

Met Asp Thr Glu Thr Trp Ala Ala Ala Arg Pro Ser Arg Asp Ala
1               5                   10                  15

Leu Ile Asn Arg Ile Thr His Gln Ile Arg Gln Ser Leu Glu Leu Asp
                20                  25                  30

Gln Ile Leu Arg Ala Thr Val Glu Val Arg Ala Phe Leu Gly Thr
            35                  40                  45

Asp Arg Val Lys Val Tyr Arg Phe Asp Pro Glu Gly His Gly Thr Val
        50                  55                  60

Val Ala Glu Ala Arg Gly Gly Glu Arg Leu Pro Ser Leu Leu Gly Leu
65                  70                  75                  80

Thr Phe Pro Ala Gly Asp Ile Pro Glu Glu Ala Arg Arg Leu Phe Arg
                85                  90                  95

Leu Ala Gln Val Arg Val Ile Val Asp Val Glu Ala Gln Ser Arg Ser
            100                 105                 110

Ile Ser Gln Pro Glu Ser Trp Gly Leu Ser Ala Arg Val Pro Leu Gly
        115                 120                 125

Glu Pro Leu Gln Arg Pro Val Asp Pro Cys His Val His Tyr Leu Lys
130                 135                 140

Ser Met Gly Val Ala Ser Ser Leu Val Val Pro Leu Met His His Gln
145                 150                 155                 160

Glu Leu Trp Gly Leu Leu Val Ser His His Ala Glu Pro Arg Pro Tyr
                165                 170                 175

Ser Gln Glu Glu Leu Gln Val Val Gln Leu Leu Ala Asp Gln Val Ser
            180                 185                 190

Ile Ala Ile Ala Gln Ala Glu Leu Leu Glu Gln Ala Arg Gln Lys Ala
        195                 200                 205

Gln Gln Glu Arg Leu Ile Asn Gln Ile Ala Ala Leu Val Tyr Ser Pro
210                 215                 220

Leu His Pro Glu Thr Thr Leu Thr Val Leu Glu Gln Leu Ala Ala
225                 230                 235                 240
```

```
Gly Leu Gln Gly Ile Gly Ala Arg Leu Arg Ile His Phe Met Gly Ala
                245                 250                 255

Asp Thr Leu Cys Cys His Gly Val Gln Pro Pro Ala Ser Tyr Asp Thr
            260                 265                 270

Trp Leu Gln Glu Gln Leu Gly Arg Ala Gly Ala Gly Gly Trp Val
        275                 280                 285

Lys Met Trp Ser Leu Ser His Leu Glu Lys Trp Pro Glu Leu Gln Glu
    290                 295                 300

Gln Met Lys Gln Thr Pro Ile Arg Gly Leu Val Ala Gln Leu Ala
305                 310                 315                 320

Trp Asn Asp Gln Pro Val Gly Trp Leu Ser Val Phe Arg Gly Ala Val
                325                 330                 335

Tyr Gln Glu Thr His Trp Ala Gly Tyr Arg Trp Phe Thr Gln Gly Asp
            340                 345                 350

Pro Arg Gln Glu Leu Pro Leu Ile Ser Phe Ala Ala Trp Arg Glu Leu
        355                 360                 365

Lys Ile Asp Glu Pro Lys Ala Trp Ser Ala Ala Glu Gln Glu Leu Met
    370                 375                 380

Ser Arg Val Gly Val His Leu Ala Leu Ser Ile Thr Gln Asn Gln Leu
385                 390                 395                 400

Tyr Arg Gln Leu Gln Thr Leu Asn Ala Arg Leu Glu Gln Glu Val Gln
                405                 410                 415

Glu Arg Thr Ala Ala
            420

<210> SEQ ID NO 7
<211> LENGTH: 200
<212> TYPE: PRT
<213> ORGANISM: Synechococcus OS B'

<400> SEQUENCE: 7

Met Asp Thr Glu Thr Trp Ala Ala Ala Arg Pro Ser Arg Asp Ala
1               5                   10                  15

Leu Ile Asn Arg Ile Thr His Gln Ile Arg Gln Ser Leu Glu Leu Asp
                20                  25                  30

Gln Ile Leu Arg Ala Thr Val Glu Glu Val Arg Ala Phe Leu Gly Thr
            35                  40                  45

Asp Arg Val Lys Val Tyr Arg Phe Asp Pro Glu Gly His Gly Thr Val
        50                  55                  60

Val Ala Glu Ala Arg Gly Gly Glu Arg Leu Pro Ser Leu Leu Gly Leu
65                  70                  75                  80

Thr Phe Pro Ala Gly Asp Ile Pro Glu Glu Ala Arg Arg Leu Phe Arg
                85                  90                  95

Leu Ala Gln Val Arg Val Ile Val Asp Val Glu Ala Gln Ser Arg Ser
            100                 105                 110

Ile Ser Gln Pro Glu Ser Trp Gly Leu Ser Ala Arg Val Pro Leu Gly
        115                 120                 125

Glu Pro Leu Gln Arg Pro Val Asp Pro Cys His Val His Tyr Leu Lys
    130                 135                 140

Ser Met Gly Val Ala Ser Ser Leu Val Val Pro Leu Met His Gln
145                 150                 155                 160

Glu Leu Trp Gly Leu Leu Val Ser His His Ala Glu Pro Arg Pro Tyr
                165                 170                 175

Ser Gln Glu Glu Leu Gln Val Val Gln Leu Leu Ala Asp Gln Val Ser
            180                 185                 190
```

Ile Ala Ile Ala Gln Ala Glu Leu
        195                 200

<210> SEQ ID NO 8
<211> LENGTH: 154
<212> TYPE: PRT
<213> ORGANISM: Synechococcus OS B'

<400> SEQUENCE: 8

Gly Thr Asp Arg Val Lys Val Tyr Arg Phe Asp Pro Glu Gly His Gly
1               5                   10                  15

Thr Val Val Ala Glu Ala Arg Gly Gly Glu Arg Leu Pro Ser Leu Leu
            20                  25                  30

Gly Leu Thr Phe Pro Ala Gly Asp Ile Pro Glu Glu Ala Arg Arg Leu
        35                  40                  45

Phe Arg Leu Ala Gln Val Arg Val Ile Val Asp Val Glu Ala Gln Ser
    50                  55                  60

Arg Ser Ile Ser Gln Pro Glu Ser Trp Gly Leu Ser Ala Arg Val Pro
65                  70                  75                  80

Leu Gly Glu Pro Leu Gln Arg Pro Val Asp Pro Cys His Val His Tyr
                85                  90                  95

Leu Lys Ser Met Gly Val Ala Ser Ser Leu Val Val Pro Leu Met His
            100                 105                 110

His Gln Glu Leu Trp Gly Leu Val Ser His His Ala Glu Pro Arg
        115                 120                 125

Pro Tyr Ser Gln Glu Glu Leu Gln Val Val Gln Leu Leu Ala Asp Gln
    130                 135                 140

Val Ser Ile Ala Ile Ala Gln Ala Glu Leu
145                 150

<210> SEQ ID NO 9
<211> LENGTH: 29
<212> TYPE: DNA
<213> ORGANISM: Artificial Sequence
<220> FEATURE:
<223> OTHER INFORMATION: Syn-Cph1(PAS-GAF) reaction 1 primer 1

<400> SEQUENCE: 9
catggccacc accgtacaac tcagcgacc                                   29

<210> SEQ ID NO 10
<211> LENGTH: 31
<212> TYPE: DNA
<213> ORGANISM: Artificial Sequence
<220> FEATURE:
<223> OTHER INFORMATION: Syn-Cph1(PAS-GAF) reaction 1 primer 2

<400> SEQUENCE: 10
atcttcctgg gcggaaatgt tgctaaacac c                                31

<210> SEQ ID NO 11
<211> LENGTH: 25
<212> TYPE: DNA
<213> ORGANISM: Artificial Sequence
<220> FEATURE:
<223> OTHER INFORMATION: Syn-Cph1(PAS-GAF) reaction 2 primer 1

<400> SEQUENCE: 11
gccaccaccg tacaactcag cgacc                                       25

```
<210> SEQ ID NO 12
<211> LENGTH: 35
<212> TYPE: DNA
<213> ORGANISM: Artificial Sequence
<220> FEATURE:
<223> OTHER INFORMATION: Syn-Cph1(PAS-GAF) reaction 2 primer 2

<400> SEQUENCE: 12
agctatcttc ctgggcggaa atgttgctaa acacc                                35

<210> SEQ ID NO 13
<211> LENGTH: 29
<212> TYPE: DNA
<213> ORGANISM: Artificial Sequence
<220> FEATURE:
<223> OTHER INFORMATION: SyA-Cph1(GAF) reaction 1 primer 1

<400> SEQUENCE: 13
catggaaacc ttggcccctg cagcctgcg                                       29

<210> SEQ ID NO 14
<211> LENGTH: 30
<212> TYPE: DNA
<213> ORGANISM: Artificial Sequence
<220> FEATURE:
<223> OTHER INFORMATION: SyA-Cph1(GAF) reaction 1 primer 2

<400> SEQUENCE: 14
aattccgcct gggcaatggc aatcgacacc                                      30

<210> SEQ ID NO 15
<211> LENGTH: 28
<212> TYPE: DNA
<213> ORGANISM: Artificial Sequence
<220> FEATURE:
<223> OTHER INFORMATION: SyA-Cph1(GAF) reaction 2 primer 1

<400> SEQUENCE: 15
atggaaacct tggcccctgc agcctgcg                                        28

<210> SEQ ID NO 16
<211> LENGTH: 34
<212> TYPE: DNA
<213> ORGANISM: Artificial Sequence
<220> FEATURE:
<223> OTHER INFORMATION: SyA-Cph1(GAF) reaction 2 primer 2

<400> SEQUENCE: 16
agctaattcc gcctgggcaa tggcaatcga cacc                                 34

<210> SEQ ID NO 17
<211> LENGTH: 27
<212> TYPE: DNA
<213> ORGANISM: Artificial Sequence
<220> FEATURE:
<223> OTHER INFORMATION: SyB-Cph1(GAF) reaction 1 primer 1

<400> SEQUENCE: 17
catggatact gaaacgtggg ctgccgc                                         27

<210> SEQ ID NO 18
<211> LENGTH: 26
<212> TYPE: DNA
<213> ORGANISM: Artificial Sequence
<220> FEATURE:
<223> OTHER INFORMATION: SyB-Cph1(GAF) reaction 1 primer 2
```

<400> SEQUENCE: 18
caattccgcc tgagcaatgg caatgg								26

<210> SEQ ID NO 19
<211> LENGTH: 23
<212> TYPE: DNA
<213> ORGANISM: Artificial Sequence
<220> FEATURE:
<223> OTHER INFORMATION: SyB-Cph1(GAF) reaction 2 primer 1

<400> SEQUENCE: 19
gatactgaaa cgtgggctgc cgc								23

<210> SEQ ID NO 20
<211> LENGTH: 30
<212> TYPE: DNA
<213> ORGANISM: Artificial Sequence
<220> FEATURE:
<223> OTHER INFORMATION: SyB-Cph1(GAF) reaction 2 primer 2

<400> SEQUENCE: 20
agctcaattc cgcctgagca atggcaatgg							30

<210> SEQ ID NO 21
<211> LENGTH: 29
<212> TYPE: DNA
<213> ORGANISM: Artificial Sequence
<220> FEATURE:
<223> OTHER INFORMATION: SyA-Cph1(GAF-PHY) reaction 1 primer 1

<400> SEQUENCE: 21
catggaaacc ttggcccctg cagcctgcg								29

<210> SEQ ID NO 22
<211> LENGTH: 20
<212> TYPE: DNA
<213> ORGANISM: Artificial Sequence
<220> FEATURE:
<223> OTHER INFORMATION: SyA-Cph1(GAF-PHY) reaction 1 primer 2

<400> SEQUENCE: 22
ggccgccgtc cgctcctcta								20

<210> SEQ ID NO 23
<211> LENGTH: 28
<212> TYPE: DNA
<213> ORGANISM: Artificial Sequence
<220> FEATURE:
<223> OTHER INFORMATION: SyA-Cph1(GAF-PHY) reaction 2 primer 1

<400> SEQUENCE: 23
atggaaacct tggcccctgc agcctgcg								28

<210> SEQ ID NO 24
<211> LENGTH: 25
<212> TYPE: DNA
<213> ORGANISM: Artificial Sequence
<220> FEATURE:
<223> OTHER INFORMATION: SyA-Cph1(GAF-PHY) reaction 2 primer 2

<400> SEQUENCE: 24
agctggccgc cgtccgctcc tctac								25

<210> SEQ ID NO 25
<211> LENGTH: 27

```
<212> TYPE: DNA
<213> ORGANISM: Artificial Sequence
<220> FEATURE:
<223> OTHER INFORMATION: SyB-Cph1(GAF-PHY) reaction 1 primer 1

<400> SEQUENCE: 25
catggatact gaaacgtggg ctgccgc                                          27

<210> SEQ ID NO 26
<211> LENGTH: 19
<212> TYPE: DNA
<213> ORGANISM: Artificial Sequence
<220> FEATURE:
<223> OTHER INFORMATION: SyB-Cph1(GAF-PHY) reaction 1 primer 2

<400> SEQUENCE: 26
ggccgccgtc cgctcctgc                                                  19

<210> SEQ ID NO 27
<211> LENGTH: 23
<212> TYPE: DNA
<213> ORGANISM: Artificial Sequence
<220> FEATURE:
<223> OTHER INFORMATION: SyB-Cph1(GAF-PHY) reaction 2 primer 1

<400> SEQUENCE: 27
gatactgaaa cgtgggctgc cgc                                             23

<210> SEQ ID NO 28
<211> LENGTH: 23
<212> TYPE: DNA
<213> ORGANISM: Artificial Sequence
<220> FEATURE:
<223> OTHER INFORMATION: SyB-Cph1(GAF-PHY) reaction 2 primer 2

<400> SEQUENCE: 28
agctggccgc cgtccgctcc tgc                                             23

<210> SEQ ID NO 29
<211> LENGTH: 36
<212> TYPE: DNA
<213> ORGANISM: Artificial Sequence
<220> FEATURE:
<223> OTHER INFORMATION: Syn-Cph1 D207H primer 1

<400> SEQUENCE: 29
ctgcactatc ccgaatcgca tattccccaa cccgcc                               36

<210> SEQ ID NO 30
<211> LENGTH: 36
<212> TYPE: DNA
<213> ORGANISM: Artificial Sequence
<220> FEATURE:
<223> OTHER INFORMATION: Syn-Cph1 D207H primer 2

<400> SEQUENCE: 30
ggcgggttgg ggaatatgcg attcgggata gtgcag                               36

<210> SEQ ID NO 31
<211> LENGTH: 41
<212> TYPE: DNA
<213> ORGANISM: Artificial Sequence
<220> FEATURE:
<223> OTHER INFORMATION: Syn-Cph1 Y176H primer 1

<400> SEQUENCE: 31
```

```
gctttgaccg ggtgatgcta caccgctttg atgaaaataa c                    41

<210> SEQ ID NO 32
<211> LENGTH: 41
<212> TYPE: DNA
<213> ORGANISM: Artificial Sequence
<220> FEATURE:
<223> OTHER INFORMATION: Syn-Cph1 Y176H primer 2

<400> SEQUENCE: 32
gttattttca tcaaagcggt gtagcatcac ccggtcaaag c                    41

<210> SEQ ID NO 33
<211> LENGTH: 36
<212> TYPE: DNA
<213> ORGANISM: Artificial Sequence
<220> FEATURE:
<223> OTHER INFORMATION: SyB-Cph1 D86H primer 1

<400> SEQUENCE: 33 ctgactttc cggcagggca cattcccgag gaggcg                           36

<210> SEQ ID NO 34
<211> LENGTH: 36
<212> TYPE: DNA
<213> ORGANISM: Artificial Sequence
<220> FEATURE:
<223> OTHER INFORMATION: SyB-Cph1 D86H primer 2

<400> SEQUENCE: 34
cgcctcctcg ggaatgtgcc ctgccggaaa agtcag                          36

<210> SEQ ID NO 35
<211> LENGTH: 33
<212> TYPE: DNA
<213> ORGANISM: Artificial Sequence
<220> FEATURE:
<223> OTHER INFORMATION: SyB-Cph1 Y54H primer 1

<400> SEQUENCE: 35
cggatcgggt gaaggtgcac cgcttcgacc cgg                             33

<210> SEQ ID NO 36
<211> LENGTH: 33
<212> TYPE: DNA
<213> ORGANISM: Artificial Sequence
<220> FEATURE:
<223> OTHER INFORMATION: SyB-Cph1 Y54H primer 2

<400> SEQUENCE: 36
ccgggtcgaa gcggtgcacc ttcacccgat ccg                             33

<210> SEQ ID NO 37
<211> LENGTH: 44
<212> TYPE: DNA
<213> ORGANISM: Artificial Sequence
<220> FEATURE:
<223> OTHER INFORMATION: SyB-Cph1 C138A primer 1

<400> SEQUENCE: 37
ctgcagcggc ccgtggatcc cgcccatgtt cactatttga aatc                 44

<210> SEQ ID NO 38
<211> LENGTH: 44
<212> TYPE: DNA
<213> ORGANISM: Artificial Sequence
```

```
<220> FEATURE:
<223> OTHER INFORMATION: SyB-Cph1 C138A primer 2

<400> SEQUENCE: 38
gatttcaaat agtgaacatg ggcgggatcc acgggccgct gcag                    44

<210> SEQ ID NO 39
<211> LENGTH: 31
<212> TYPE: DNA
<213> ORGANISM: Artificial Sequence
<220> FEATURE:
<223> OTHER INFORMATION: Primer

<400> SEQUENCE: 39
agctttgcat catcatcatc atcattgaag c                                 31

<210> SEQ ID NO 40
<211> LENGTH: 31
<212> TYPE: DNA
<213> ORGANISM: Artificial Sequence
<220> FEATURE:
<223> OTHER INFORMATION: Primer

<400> SEQUENCE: 40
agctgcttca atgatgatga tgatgatgca a                                 31

<210> SEQ ID NO 41
<211> LENGTH: 32
<212> TYPE: DNA
<213> ORGANISM: Artificial Sequence
<220> FEATURE:
<223> OTHER INFORMATION: Primer

<400> SEQUENCE: 41
cgtaaggatc catgagccgg gacccgttgc cc                                32

<210> SEQ ID NO 42
<211> LENGTH: 32
<212> TYPE: DNA
<213> ORGANISM: Artificial Sequence
<220> FEATURE:
<223> OTHER INFORMATION: Primer

<400> SEQUENCE: 42
cctgactcga gcgccccggt caatgtgtca cg                                32

<210> SEQ ID NO 43
<211> LENGTH: 12
<212> TYPE: PRT
<213> ORGANISM: Artificial Sequence
<220> FEATURE:
<223> OTHER INFORMATION: "PAS-less" phytochrome consensus amino acid
      sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 43

Arg Ile Thr Xaa Gln Ile Arg Gln Ser Leu Glu Leu
1               5                   10

<210> SEQ ID NO 44
<211> LENGTH: 9
<212> TYPE: PRT
<213> ORGANISM: Artificial Sequence
<220> FEATURE:
```

<223> OTHER INFORMATION: DUF309 domain consensus amino acid sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 44

His Xaa Xaa Xaa Glu Xaa Xaa Xaa Trp
1               5

<210> SEQ ID NO 45
<211> LENGTH: 9
<212> TYPE: PRT
<213> ORGANISM: Artificial Sequence
<220> FEATURE:
<223> OTHER INFORMATION: DUF309 domain consensus amino acid sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 45

His Xaa Xaa Xaa Glu Xaa Xaa Xaa Tyr
1               5

<210> SEQ ID NO 46
<211> LENGTH: 963
<212> TYPE: DNA
<213> ORGANISM: Deinococcus radiodurans

<400> SEQUENCE: 46

```
atgagccggg acccgttgcc cttttttcca ccgctttacc ttggtggccc ggaaattacc      60
accgagaact gcgagcgcga gccgattcat attcccggca gcatccagcc gcacggcgcc     120
ctgctcactg ccgacgggca cagcggcgag gtgctccaga tgagcctcaa cgcggccact     180
tttctgggac aggaacccac agtgctgcgc ggacagaccc tcgccgcact gctgcccgag     240
cagtggcccg cgctgcaagc gggccctgcc ccggctgcc cgacgccct gcaataccgc      300
gcaacgctgg actggcctgc cgccgggcac cttcgctga cggtgcaccg ggtcggcgag     360
ttgctgattc tggaattcga gccgacgag gcctgggaca gcaccgggcc gcacgcgctg      420
cgcaacgcga tgttcgcgct cgaaagtgcc cccaacctgc gggcgctggc cgaggtggcg     480
acccagacgg tccgcgagct gacgggcttt gaccgggtga tgctctacaa atttgccccc     540
gacgccaccg gcgaagtgat tgccgaggcc cgccgtgagg ggctgcacgc ctttctgggc     600
caccgttttc ccgcgtcgga cattccggcg caggcccgcg cgctctacac ccggcacctg     660
ctgcgcctga ccgccgacac ccgcgccgcc gccgtgccgc tcgatcccgt cctcaacccg     720
cagacgaatg cgcccacccc gctgggcggc gccgtgctgc gcgccacctc gcccatgcac     780
atgcagtacc tgcggaacat gggcgtcggg tcgagcctgt cggtgtcggt ggtggtcggc     840
ggccagctct ggggcctgat cgcctgccac caccagacgc cctacgtgtt gccgcccgac     900
ctgcgaacca cgctcgaata cctgggccgc ttgctgagcc tgcaagttca ggtcaaggaa     960
gcg                                                                  963
```

<210> SEQ ID NO 47
<211> LENGTH: 2505
<212> TYPE: DNA
<213> ORGANISM: Synechococcus OS A'

<400> SEQUENCE: 47

```
atggaaacct tggccctgc agcctgcgcc agccgggatg tcctcatcaa ccgcattacc      60
caccagatcc ggcaatccct ggagctggat cagatcctga gggcaacggt ggaggaggtg     120
cgcgccttt tgggcacgga tcgggtcaag gtataccgct tcgacccgga aggccatggg     180
acggtggtgg cggaagcccg acaagccgag cggttgccct ccctcttggg cctatcgttt     240
ccggcggggg atatcccaga gaggcgcgg cagctgtttc gcctggccca ggtgcgggtg     300
atcgtggatg tggaggccca gaccgcttc ctcagccagc cggagtcgct gggccgcttt     360
gcccaggccc ggccttttgcc cctgggcgag gtgccgcagc ggctggtgga tccctgccat     420
gcccactacc tcaagtgcat ggggtggcc tcctccctgg tggtacccct cctgcatcac     480
cagcagttgt gggggctctt ggtctcccac acgccgagc cccgctccta ctctgccgaa     540
gagctgcagg tggtgcagtt ggtggcggat caggtgtcga ttgccattgc caggcggaa     600
ttgctggagc aggcgcggca aaaggcgcag caggaacgtt tgattaacca aattgcggcg     660
ctggtgtact cgccgctcca ccccgagacc accttgacca ctgtgctgga gcagcttacc     720
gccggcctcc aagggatcgg ggcgcggctg cgcatccggt tcctgggcct ggacaccctc     780
tgccaccatg ggatccagcc gccggcaggc tacgacgcct ggctgcagga gcaggtggga     840
aggcccaaga gcaggaaa cggggtgaag acgtggtcgc tttcccagtt ggagaagtgg     900
ccagaactgc aggcccagct gcagcagacg cccattcgcg ggctgctggc ggtgccgctg     960
gtttggaacg agcagctggt gggctggctg agcgtctttc gcggcgccct ctgccaagag    1020
acccactggg ccggctaccg ctggcccgcc aaggggaag gtggggagga tccccgtcaa    1080
gaactgccgt tgatctcctt tgccgcttgg cgggagctga agttgacga gcccaaggcc    1140
tggtcggccg cggagctgga gctagtcggc gcgcgctgcgg tgcacctggc cctgtcgatt    1200
gcgcaaaacc agctctaccg gcagttgcaa gatctcaacg cccgtctgga gcacgaggta    1260
gaggagcgga cggcggccct gcagcgctct ttggccatgg atgccctctt gcagcgggtt    1320
accgaccagg tgcgcagcag cctagacgaa gcccagatcc tgcgggcggt ggtgcaggag    1380
ttggcgctgg ggctgcccat ccaaggctgc gatctctgcc tctacgaggg agcagccggc    1440
caggccaccg tgcgctatga atacaccgcc gccctgccgc cgccggcgg gatcacccta    1500
accctggccg actacccaga tctctaccga caactgcaaa gggggcaggc ggcgcaactg    1560
tgccatctgc cggggcaaag ctggatccca cggcgggaag ggctgacgct tttggtttgc    1620
ccgctgcgga tgaccaggg ggcgttgggc gatctgtggt tggccaaggc ggcagccgag    1680
tgctttgata ccctggagat gcaggtggta cagcaggtag cggatcactg tgccatcgcc    1740
atccgccagg ctcgcctcta ccaggcctcg gtgcaacaaa tcagcgagct ggagcgcctc    1800
aaccgcctca agatgatttt tttaagcacc gtctcccacg agctgcgcac cccatcacc    1860
aacatgaaaa tggccatcca actgctgaaa atggcccgca ccccccaaaa acgggagcaa    1920
tatctgcaaa tcctagagca ggagtgcgag cgcgaggcgg aattgatcaa cgatctgctg    1980
gatctgcagc ggttggagca gggatccaaa ccccttcatc ttgaagaagt gtccctggcc    2040
gcctggctgc ccactgtgct gcagccctt gtgcagcggg ccgaggccaa tcagcaacag    2100
ttgcagtggc agattgaccc gaaggtgggc aaggtggtga cggatcaggc cgccttgacg    2160
```

```
cgggtggtac aggagctggt caacaacgcc tgcaagtaca ccccgcctca gcaccgcatc    2220
acggtgacgg cgcgccgcct cagccctgaa caagtgcaaa ttcgggtggt caacgagggg    2280
gtggagattc cccgcagcga gtgggagcgc atcttcgaga agttctaccg catccccagc    2340
ggggatccct ggaagcgggg cggcaccggc ctggggctgg ctttggttaa gcagtggatg    2400
cagcggctgg ggggctgcgt ctctatagaa agcggccagg gcaagacgtg ctttaccctg    2460
gtgttgccgc aaggatccct gcctgggcag acctcttgca ccgcg                   2505

<210> SEQ ID NO 48
<211> LENGTH: 2502
<212> TYPE: DNA
<213> ORGANISM: Synechococcus OS B'

<400> SEQUENCE: 48
atggatactg aaacgtgggc tgccgcagct cgacccagcc gagatgccct catcaaccgc     60
atcacccacc agattcggca atccctggag ctggatcaga tcctgagggc gacggtggag    120
gaggtgcgcg cctttttggg tacgatcgg gtgaaggtgt accgcttcga cccggaaggg     180
catgggacgg tggtggcgga agcacgaggc ggggagcggc tgccctcgct cttggggctg    240
acttttccgg caggggacat tcccgaggag gcgcggcggt gtttcgcct agctcaggtg     300 cgggtgattg tggatgtaga ggcgcagagc cgttccatca gccagccgga gtcttggggg    360
ttgtctgcta gggttcctct gggcgagccg ctgcagcggc ccgtggatcc ctgccatgtt    420
cactatttga aatccatggg ggtggcctct tccttggtgg ttcccctgat gcatcaccag    480
gagctatggg ggctgttggt ctcccatcat gctgagcctc gtccctactc caagaagag    540 ctgcaggtgg tgcagttgct ggcggatcaa gttccattg ccattgctca ggcggaattg     600
ctggagcaag cgcggcaaaa ggcgcagcag gaacgcctaa tcaaccaaat tgctgccctg    660
gtttattcgc ccctacaccc ggagacgacc ttgaccacgg tgctggagca gcttgctgcc    720
ggtttgcagg gatcggggc acggctgcgg atccacttta tgggcgcaga caccctctgt    780
tgtcatggcg tgcaaccccc ggccagctac gacacctggc tacaggagca gctcggaagg    840 gccgaggag cggggggctg ggtcaagatg tggtcgctct cccacttgga gaaatggccg    900
gagctgcaag agcagatgaa gcagacaccc attcgtggcc tgctggtggc ccagctcgcc    960
tggaatgacc agccggtggg ctggctgagc gtgtttcgcg gggccgtta ccaagaaacc    1020 cactgggcgg gctaccgttg gtttacccag ggggatccca gacaagaact gcctttgatc    1080
tcttttgctg cctggcggga gctgaaaatt gacgagccta aggcttggtc agctgcagag    1140
caagagctga tgagtcgggt cgggtacat ttggccctgt ccattacgca aaatcagctc    1200
taccggcagt tgcaaaccct caacgcccgt ctggagcagg aggtgcagga gcggacggcg    1260
gccctgcagc gatctctggc tatggatgcc ctcttgcagc gggtcaccga ccaggtgcgc    1320
agcagtttgg aggaagccca gatcctgcgg gcagtggtgc aagaattggc tctggggttg    1380
cccattcaag gttgcgatct ctgtctctac gattgggcat ctggccaggc gacggtgcgc    1440
tatgaataca cctctgctct accacctgcc ggtgggatca ccctgacctt ggccgactac    1500
cccgatcttt accggcacct gcaagggggt caagcggtgc aattctgcca cttgcctggg    1560
cagggctgga tccccgtcg ggaagggctg acctgctgg tgtgcccgct gcgggatgac    1620 caagggggtgc tgggggatct ctggctggcg aagccggcag ccaagtgctt tgatgaactg    1680
gaggtgcagg tggtgcagca ggtggcggat cactgcgcca ttgccatccg ccaggcccgc    1740
ctctaccagg cttctgtgca gcaaattggt gagctggagc gcctcaaccg cctcaaagat    1800
```

```
gatttttttga gcaccgtctc ccacgagctg cgcaccccca tcaccaacat gaggatggcc    1860
atccaactgc tgaaaaccgc ccgcgccccc caaaaacgag agcaatatct caagatcttg    1920
gagcaggagt gtgagcggga ggcggaattg gtgaacgacc tgctggatct gcagcggttg    1980
gagcagggat ccaaaacgct ccatctggaa gaagtgccgc tggcaacctg gctgcccagc    2040
gtgctggagc cgtttctaca gcgggcccag gtcaaccagc aacggttgca gtggcagatc    2100
gcgccgaatg tgggcaaggt gctcaccgat caaggtggcc tggagcgggt ggtgcaggag    2160
ctggtcaaca acgcctgcaa gtatactccc ccagggtgca gcatctgggt aacagcgcag    2220
cggcccggcc cgcagcaggt ggaaatccgg gtgatcaacg aggggggtgga aatttcccct    2280 gccgagcagg agcgcatctt cgagaagttc taccgcattc ccagcgggga tccctggaaa    2340
cggggcggca ccggcctggg cctggctttg gtcaagcagt ggatgcagcg gttgggggc    2400 agcgtctcag tggagagctc tcaaggcaaa acctgcttta ccctggtgtt gccgcaggga    2460
tccctgcctg tgcagacctc accoctagcc cacaactgtg cc                       2502
```

What is claimed is:

1. A cell that comprises a DNA molecule having a regulatory element from a gene, other than a gene encoding a *Deinococcus radiodurans* phytochrome, operably linked to a DNA sequence that encodes a polypeptide that is (i) at least 80% identical to the chromophore-binding domain of SEQ ID NO: 1; or (ii) at least 80% identical to the sequence of SEQ ID NO: 2; wherein the polypeptide has increased fluorescent activity over the corresponding wild-type phytochrome domain, wherein the polypeptide comprises a D207H mutation from the phytochrome of *Deinococcus radiodurans*.

2. The cell of claim 1, wherein the cell is selected from the group consisting of a bacterial cell, a yeast cell, a fungal cell, a plant cell, an insect cell, a nematode cell, an animal cell, and a human cell.

3. An isolated polynucleotide comprising a sequence that encodes a polypeptide that is (i) at least 80% identical to the chromophore-binding domain of SEQ ID NO: 1; or (ii) at least 80% identical to the sequence of SEQ ID NO: 2; wherein the polypeptide contains a His rather than an Asp in the *Deinococcus radiodurans* DIP motif, wherein the polypeptide has increased fluorescent activity over the corresponding wild-type phytochrome domain.

4. The polynucleotide of claim 3, wherein the sequence encodes a polypeptide that is at least 80% identical to SEQ ID NO: 2.

5. The polynucleotide of claim 4, wherein the sequence encodes a polypeptide that is at least 95% identical to the chromophore binding domain of SEQ ID NO: 1, at least 95% identical to SEQ ID NO: 2, or a combination thereof.

6. The polynucleotide of claim 4, wherein the increased fluorescent activity comprises an intensity that is at least 75% greater compared with the corresponding wild-type domain.

7. The polynucleotide of claim 3, wherein the increased fluorescent activity comprises an intensity that is at least 75% greater compared with the corresponding wild-type domain.

8. The polynucleotide of claim 3, wherein the increased fluorescent activity comprises an intensity that is at least 200% greater compared with the corresponding wild-type domain.

9. The polynucleotide of claim 3, wherein the polypeptide comprises an Ala rather than an Ile in the *Deinococcus radiodurans* DIP motif.

10. The polynucleotide of claim 3, comprising the sequence encoding a modified phytochrome domain having increased fluorescent activity shifted to the far red.

11. An expression vector comprising the isolated polynucleotide of claim 3 and a regulatory sequence operably linked to the polynucleotide.

12. A cell comprising the polynucleotide of claim 3.

13. The cell of claim 12, wherein the cell is selected from the group consisting of a bacterial cell, a fungal cell, an insect cell, a nematode cell and an animal cell.

14. The cell of claim 13, wherein the cell is a human cell or a yeast cell.

15. The cell of claim 1, wherein the polypeptide further comprises one or more mutations of the phytochrome of *Deinococcus radiodurans* selected from E25A, E27A, I35A, P37A, Y176H, F203A, F203H, F203W, I208A, Y216H, Y216W, R254A, R254K, Y263H, H290N and H290Q.

16. An isolated polynucleotide comprising a sequence that encodes a polypeptide that is (i) at least 80% identical to the chromophore-binding domain of SEQ ID NO: 1; or (ii) at least 80% identical to SEQ ID NO: 2; and with increased fluorescent activity over the corresponding wild-type phytochrome domain, wherein the polypeptide comprises a D207H mutation from the phytochrome of *Deinococcus radiodurans*.

17. The polynucleotide of claim 16, wherein the polypeptide further comprises one or more mutations of the phytochrome of *Deinococcus radiodurans* selected from E25A, E27A, I35A, P37A, Y176H, F203A, F203H, F203W, I208A, Y216H, Y216W, R254A, R254K, Y263H, H290N and H290Q.

* * * * *